United States Patent
Pesach et al.

(10) Patent No.: US 8,622,991 B2
(45) Date of Patent: Jan. 7, 2014

(54) METHOD AND DEVICE FOR DRUG DELIVERY

(75) Inventors: Benny Pesach, Rosh-ha ayin (IL); Gabriel Bitton, Jerusalem (IL); Ram Weiss, Haifa (IL); Ron Nagar, Tel Aviv (IL)

(73) Assignee: Insuline Medical Ltd., Petach-Tikva (IL)

( * ) Notice: Subject to any disclaimer, the term of this patent is extended or adjusted under 35 U.S.C. 154(b) by 739 days.

(21) Appl. No.: 12/450,246

(22) PCT Filed: Mar. 19, 2008

(86) PCT No.: PCT/IB2008/051044
§ 371 (c)(1),
(2), (4) Date: Feb. 19, 2010

(87) PCT Pub. No.: WO2008/114218
PCT Pub. Date: Sep. 25, 2008

(65) Prior Publication Data
US 2010/0152644 A1    Jun. 17, 2010

Related U.S. Application Data

(63) Continuation-in-part of application No. 11/821,230, filed on Jun. 21, 2007.

(60) Provisional application No. 60/895,518, filed on Mar. 19, 2007, provisional application No. 60/895,519, filed on Mar. 19, 2007, provisional application No. 60/912,698, filed on Apr. 19, 2007, provisional application No. 60/940,721, filed on May 30, 2007, provisional application No. 61/008,278, filed on Dec. 18, 2007, provisional application No. 60/956,700, filed on Aug. 19, 2007, provisional application No. 60/970,997, filed on Sep. 10, 2007, provisional application No. 61/008,325, filed on Dec. 18, 2007, provisional application No. 61/008,274, filed on Dec. 18, 2007, provisional application No. 61/008,277, filed on Dec. 18, 2007.

(51) Int. Cl.
*A61M 31/00* (2006.01)
*A61M 5/32* (2006.01)

(52) U.S. Cl.
USPC .............. 604/508; 604/500; 604/513; 604/67; 604/174; 604/113

(58) Field of Classification Search
USPC ............... 604/65, 67, 31, 508, 513, 113, 174, 604/180, 131, 151, 500
See application file for complete search history.

(56) References Cited

U.S. PATENT DOCUMENTS 3,620,209 A    11/1971  Kravitz
3,683,911 A    8/1972  McCormick
(Continued)

FOREIGN PATENT DOCUMENTS

EP    1611848    1/2006
EP    1695664    8/2006
(Continued)

OTHER PUBLICATIONS

Belinda et. al., (1996), Journal of Physiology, 572.3:811-820.
(Continued)

*Primary Examiner* — Emily Schmidt
*Assistant Examiner* — Bradley G Thomas, Jr.
(74) *Attorney, Agent, or Firm* — Mintz Levin Cohn Ferris Glovsky and Popeo, P.C.

(57) ABSTRACT

Systems, devices and methods for delivery of a chemical substance to the body of the patient are provided. Such embodiments may include an infusion catheter configured to be inserted into tissue, a catheter securing element configured to be adhered to the skin of the patient and further configured to secure the infusion catheter to the skin, a drug delivery pump configured to infuse a drug into the infusion catheter for delivery to a drug infused region on the body of the patient, and a treatment element configured to apply a treatment to the drug infused region to improve pharmacodynamics of the drug during a period of delivery of the drug to the patient.

22 Claims, 40 Drawing Sheets

(56) References Cited

U.S. PATENT DOCUMENTS

| | | |
|---|---|---|
| 4,230,105 A | 10/1980 | Harwood |
| H71 H | 6/1986 | Sorenson et al. |
| 4,628,928 A | 12/1986 | Lowell |
| 4,685,911 A | 8/1987 | Konno et al. |
| 4,744,787 A | 5/1988 | Phipps et al. |
| 4,747,819 A | 5/1988 | Phipps et al. |
| 4,771,772 A | 9/1988 | DeWitt |
| 4,898,592 A | 2/1990 | Latzke et al. |
| 4,948,587 A | 8/1990 | Kost et al. |
| 4,963,360 A | 10/1990 | Argaud |
| 4,987,897 A | 1/1991 | Funke |
| 4,998,930 A | 3/1991 | Lundahl |
| 5,047,007 A | 9/1991 | McNichols et al. |
| 5,053,033 A | 10/1991 | Clarke |
| 5,098,429 A | 3/1992 | Sterzer |
| 5,113,859 A | 5/1992 | Funke |
| 5,135,477 A | 8/1992 | Untereker et al. |
| 5,213,568 A | 5/1993 | Lattin et al. |
| 5,243,986 A | 9/1993 | Wurster |
| 5,271,736 A | 12/1993 | Picha |
| 5,306,252 A | 4/1994 | Yutori et al. |
| 5,307,816 A | 5/1994 | Hashimoto et al. |
| 5,324,521 A | 6/1994 | Gertner et al. |
| 5,332,577 A | 7/1994 | Gertner et al. |
| 5,354,324 A | 10/1994 | Gregory |
| 5,378,475 A | 1/1995 | Smith et al. |
| 5,383,873 A | 1/1995 | Hoey et al. |
| 5,411,550 A | 5/1995 | Herweck et al. |
| 5,430,016 A | 7/1995 | Balschmidt et al. |
| 5,498,254 A | 3/1996 | Hoey et al. |
| 5,512,048 A | 4/1996 | Slettenmark |
| 5,523,092 A | 6/1996 | Hanson et al. |
| 5,525,356 A | 6/1996 | Jevne et al. |
| 5,527,292 A | 6/1996 | Adams et al. |
| 5,545,208 A | 8/1996 | Wolff et al. |
| 5,556,421 A | 9/1996 | Prutchi et al. |
| 5,564,439 A | 10/1996 | Picha |
| 5,567,592 A | 10/1996 | Benet et al. |
| 5,571,152 A | 11/1996 | Chen et al. |
| 5,590,657 A | 1/1997 | Cain et al. |
| 5,591,445 A | 1/1997 | Hoey et al. |
| 5,634,468 A | 6/1997 | Platt et al. |
| 5,658,583 A | 8/1997 | Zhang et al. |
| 5,706,807 A | 1/1998 | Picha |
| 5,713,847 A | 2/1998 | Howard, III et al. |
| 5,725,017 A | 3/1998 | Elsberry et al. |
| 5,725,567 A | 3/1998 | Wolff et al. |
| 5,730,125 A | 3/1998 | Prutchi et al. |
| 5,741,211 A | 4/1998 | Renirie et al. |
| 5,798,065 A | 8/1998 | Picha |
| 5,843,051 A | 12/1998 | Adams et al. |
| 5,851,217 A | 12/1998 | Wolff et al. |
| 5,851,231 A | 12/1998 | Wolff et al. |
| 5,871,446 A | 2/1999 | Wilk |
| 5,871,535 A | 2/1999 | Wolff et al. |
| 5,882,332 A | 3/1999 | Wijay |
| 5,919,216 A | 7/1999 | Houben et al. |
| 5,919,479 A | 7/1999 | Zhang et al. |
| 5,997,468 A | 12/1999 | Wolff et al. |
| 6,004,346 A | 12/1999 | Wolff et al. |
| 6,004,927 A | 12/1999 | Benet et al. |
| 6,026,316 A | 2/2000 | Kucharczyk et al. |
| 6,028,054 A | 2/2000 | Benet et al. |
| 6,043,273 A | 3/2000 | Duhaylongsod |
| 6,060,454 A | 5/2000 | Duhaylongsod |
| 6,061,587 A | 5/2000 | Kucharczyk et al. |
| 6,087,394 A | 7/2000 | Duhaylongsod |
| 6,093,167 A | 7/2000 | Houben et al. |
| 6,101,412 A | 8/2000 | Duhaylongsod |
| 6,122,536 A | 9/2000 | Sun et al. |
| 6,125,290 A | 9/2000 | Miesel |
| 6,125,291 A | 9/2000 | Miesel et al. |
| 6,127,117 A | 10/2000 | Morris et al. |
| 6,127,410 A | 10/2000 | Duhaylongsod |
| 6,133,242 A | 10/2000 | Zalewski et al. |
| 6,134,459 A | 10/2000 | Roberts et al. |
| 6,135,978 A | 10/2000 | Houben et al. |
| 6,141,589 A | 10/2000 | Duhaylongsod |
| 6,144,866 A | 11/2000 | Miesel et al. |
| 6,152,898 A | 11/2000 | Olsen |
| 6,156,029 A | 12/2000 | Mueller |
| 6,161,047 A | 12/2000 | King et al. |
| 6,198,952 B1 | 3/2001 | Miesel |
| 6,198,966 B1 | 3/2001 | Heruth |
| 6,210,368 B1 | 4/2001 | Rogers |
| 6,228,050 B1 | 5/2001 | Olsen et al. |
| 6,228,595 B1 | 5/2001 | Morris et al. |
| 6,238,367 B1 | 5/2001 | Christiansen et al. |
| 6,245,347 B1 | 6/2001 | Zhang et al. |
| 6,247,812 B1 | 6/2001 | Miehle et al. |
| 6,254,598 B1 | 7/2001 | Edwards et al. |
| 6,261,280 B1 | 7/2001 | Houben et al. |
| 6,261,595 B1 | 7/2001 | Stanley et al. |
| 6,269,340 B1 | 7/2001 | Ford et al. |
| 6,283,949 B1 | 9/2001 | Roorda |
| 6,284,266 B1 | 9/2001 | Zhang et al. |
| 6,292,702 B1 | 9/2001 | King et al. |
| 6,296,630 B1 | 10/2001 | Altman et al. |
| 6,303,142 B1 | 10/2001 | Zhang et al. |
| 6,305,381 B1 | 10/2001 | Weijand et al. |
| 6,306,431 B1 | 10/2001 | Zhang et al. |
| 6,312,412 B1 | 11/2001 | Saied et al. |
| 6,323,184 B1 | 11/2001 | Zalewski et al. |
| 6,338,850 B1 | 1/2002 | Jevnikar et al. |
| 6,340,472 B1 | 1/2002 | Zhang et al. |
| 6,342,250 B1 | 1/2002 | Masters |
| 6,350,276 B1 | 2/2002 | Knowlton |
| 6,375,628 B1 | 4/2002 | Zadno-Azizi et al. |
| 6,377,846 B1 | 4/2002 | Chornenky et al. |
| 6,379,382 B1 | 4/2002 | Yang |
| 6,385,491 B1 | 5/2002 | Lindemans et al. |
| 6,389,313 B1 | 5/2002 | Marchitto et al. |
| 6,395,015 B1 | 5/2002 | Borst et al. |
| 6,414,018 B1 | 7/2002 | Duhaylongsod |
| 6,416,510 B1 | 7/2002 | Altman et al. |
| 6,425,853 B1 | 7/2002 | Edwards |
| 6,427,088 B1 | 7/2002 | Bowman, IV et al. |
| 6,442,435 B2 | 8/2002 | King et al. |
| 6,447,443 B1 | 9/2002 | Keogh et al. |
| 6,449,507 B1 | 9/2002 | Hill et al. |
| 6,453,195 B1 | 9/2002 | Thompson |
| 6,453,648 B1 | 9/2002 | Zhang et al. |
| 6,456,883 B1 | 9/2002 | Torgerson et al. |
| 6,458,102 B1 | 10/2002 | Mann et al. |
| 6,458,118 B1 | 10/2002 | Lent et al. |
| 6,461,329 B1 * | 10/2002 | Van Antwerp et al. ....... 604/111 |
| 6,465,006 B1 | 10/2002 | Zhang et al. |
| 6,465,709 B1 | 10/2002 | Sun et al. |
| 6,471,675 B1 | 10/2002 | Rogers et al. |
| 6,471,689 B1 | 10/2002 | Joseph et al. |
| 6,482,214 B1 | 11/2002 | Sidor, Jr. et al. |
| 6,485,464 B1 | 11/2002 | Christenson et al. |
| 6,487,446 B1 | 11/2002 | Hill et al. |
| 6,488,959 B2 | 12/2002 | Stanley et al. |
| 6,511,428 B1 | 1/2003 | Azuma et al. |
| 6,512,958 B1 | 1/2003 | Swoyer et al. |
| 6,528,086 B2 | 3/2003 | Zhang |
| 6,532,388 B1 | 3/2003 | Hill et al. |
| 6,537,242 B1 | 3/2003 | Palmer |
| 6,542,350 B1 | 4/2003 | Rogers |
| 6,544,212 B2 | 4/2003 | Galley et al. |
| 6,546,281 B1 | 4/2003 | Zhang et al. |
| 6,551,276 B1 | 4/2003 | Mann et al. |
| 6,551,346 B2 | 4/2003 | Crossley |
| 6,554,798 B1 | 4/2003 | Mann et al. |
| 6,558,345 B1 | 5/2003 | Houben et al. |
| 6,558,382 B2 | 5/2003 | Jahns et al. |
| 6,562,001 B2 | 5/2003 | Lebel et al. |
| 6,564,105 B2 | 5/2003 | Starkweather et al. |
| 6,571,125 B2 | 5/2003 | Thompson |
| 6,572,542 B1 | 6/2003 | Houben et al. |
| 6,572,583 B1 | 6/2003 | Olsen et al. |
| 6,577,899 B2 | 6/2003 | Lebel et al. |
| 6,584,335 B1 | 6/2003 | Haar et al. |

(56) References Cited

U.S. PATENT DOCUMENTS

| | | | |
|---|---|---|---|
| 6,584,360 B2 | 6/2003 | Francischelli et al. |
| 6,585,644 B2 | 7/2003 | Lebel et al. |
| 6,585,707 B2 | 7/2003 | Cabiri et al. |
| 6,592,519 B1 | 7/2003 | Martinez |
| 6,597,946 B2 | 7/2003 | Avrahami et al. |
| 6,605,039 B2 | 8/2003 | Houben et al. |
| 6,613,082 B2 | 9/2003 | Yang |
| 6,613,084 B2 | 9/2003 | Yang |
| 6,613,350 B1 * | 9/2003 | Zhang et al. ............ 424/449 |
| 6,615,083 B2 | 9/2003 | Kupper |
| 6,620,151 B2 | 9/2003 | Blischak et al. |
| 6,622,731 B2 | 9/2003 | Daniel et al. |
| 6,626,867 B1 | 9/2003 | Christenson et al. |
| 6,628,987 B1 | 9/2003 | Hill et al. |
| 6,628,989 B1 | 9/2003 | Penner et al. |
| 6,635,167 B1 | 10/2003 | Batman et al. |
| 6,644,321 B1 | 11/2003 | Behm |
| 6,645,176 B1 | 11/2003 | Christenson et al. |
| 6,647,299 B2 | 11/2003 | Bourget |
| 6,648,821 B2 | 11/2003 | Lebel et al. |
| 6,650,935 B1 | 11/2003 | Watmough |
| 6,659,948 B2 | 12/2003 | Lebel et al. |
| 6,669,663 B1 | 12/2003 | Thompson |
| 6,673,070 B2 | 1/2004 | Edwards et al. |
| 6,673,596 B1 | 1/2004 | Sayler et al. |
| 6,675,049 B2 | 1/2004 | Thompson et al. |
| 6,681,135 B1 | 1/2004 | Davis et al. |
| 6,685,452 B2 | 2/2004 | Christiansen et al. |
| 6,687,546 B2 | 2/2004 | Lebel et al. |
| 6,690,973 B2 | 2/2004 | Hill et al. |
| 6,694,191 B2 | 2/2004 | Starkweather et al. |
| 6,697,667 B1 | 2/2004 | Lee et al. |
| 6,706,038 B2 | 3/2004 | Francischelli et al. |
| 6,711,436 B1 | 3/2004 | Duhaylongsod |
| 6,714,822 B2 | 3/2004 | King et al. |
| 6,716,178 B1 | 4/2004 | Kilpatrick et al. |
| 6,718,208 B2 | 4/2004 | Hill et al. |
| 6,723,087 B2 | 4/2004 | O'Neill et al. |
| 6,726,673 B1 | 4/2004 | Zhang et al. |
| 6,728,574 B2 | 4/2004 | Ujhelyi et al. |
| 6,733,446 B2 | 5/2004 | Lebel et al. |
| 6,733,474 B2 | 5/2004 | Kusleika |
| 6,733,476 B2 | 5/2004 | Christenson et al. |
| 6,733,500 B2 | 5/2004 | Kelley et al. |
| 6,735,471 B2 | 5/2004 | Hill et al. |
| 6,736,789 B1 | 5/2004 | Spickermann |
| 6,736,797 B1 | 5/2004 | Larsen et al. |
| 6,738,671 B2 | 5/2004 | Christophersom et al. |
| 6,740,075 B2 | 5/2004 | Lebel et al. |
| 6,743,204 B2 | 6/2004 | Christenson et al. |
| 6,743,227 B2 | 6/2004 | Seraj et al. |
| 6,744,350 B2 | 6/2004 | Blomquist |
| 6,748,653 B2 | 6/2004 | Lindemans et al. |
| 6,752,155 B2 | 6/2004 | Behm |
| 6,755,849 B1 | 6/2004 | Gowda et al. |
| 6,756,053 B2 | 6/2004 | Zhang et al. |
| 6,758,810 B2 | 7/2004 | Lebel et al. |
| 6,758,828 B2 | 7/2004 | Hammer et al. |
| 6,764,446 B2 | 7/2004 | Wolinsky et al. |
| 6,766,183 B2 | 7/2004 | Walsh et al. |
| 6,780,426 B2 | 8/2004 | Zhang et al. |
| 6,799,149 B2 | 9/2004 | Hartlaub |
| 6,804,558 B2 | 10/2004 | Haller et al. |
| 6,805,667 B2 | 10/2004 | Christopherson et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,823,213 B1 | 11/2004 | Norris et al. |
| 6,827,702 B2 | 12/2004 | Lebel et al. |
| 6,836,687 B2 | 12/2004 | Kelley et al. |
| 6,846,823 B2 | 1/2005 | Landau et al. |
| 6,852,104 B2 | 2/2005 | Blomquist |
| 6,852,694 B2 | 2/2005 | Van Antwerp et al. |
| 6,865,419 B2 | 3/2005 | Mulligan et al. |
| 6,866,678 B2 | 3/2005 | Shenderova et al. |
| 6,872,200 B2 | 3/2005 | Mann et al. |
| 6,873,268 B2 | 3/2005 | Lebel et al. |
| 6,878,529 B2 | 4/2005 | Harrow et al. |
| 6,887,238 B2 | 5/2005 | Jahns et al. |
| 6,904,318 B2 | 6/2005 | Hill et al. |
| 6,913,763 B2 | 7/2005 | Lerner |
| 6,915,157 B2 | 7/2005 | Bennett et al. |
| 6,922,585 B2 | 7/2005 | Zhou et al. |
| 6,923,784 B2 | 8/2005 | Stein |
| 6,925,393 B1 | 8/2005 | Kalatz et al. |
| 6,927,246 B2 | 8/2005 | Noronha et al. |
| 6,928,338 B1 | 8/2005 | Buchser et al. |
| 6,930,602 B2 | 8/2005 | Villaseca et al. |
| 6,936,029 B2 | 8/2005 | Mann et al. |
| 6,950,708 B2 | 9/2005 | Bowman, IV et al. |
| 6,955,661 B1 | 10/2005 | Herweck et al. |
| 6,955,819 B2 | 10/2005 | Zhang et al. |
| 6,958,705 B2 | 10/2005 | Lebel et al. |
| 6,961,448 B2 | 11/2005 | Nichols et al. |
| 6,962,584 B1 | 11/2005 | Stone et al. |
| 6,966,322 B2 | 11/2005 | McVenes et al. |
| 6,969,369 B2 | 11/2005 | Struble |
| 6,974,437 B2 | 12/2005 | Lebel et al. |
| 6,978,174 B2 | 12/2005 | Gelfand et al. |
| 6,979,315 B2 | 12/2005 | Rogers et al. |
| 6,979,326 B2 | 12/2005 | Mann et al. |
| 6,979,351 B2 | 12/2005 | Forsell et al. |
| 6,984,229 B2 | 1/2006 | Neuberger |
| 6,985,768 B2 | 1/2006 | Hemming et al. |
| 6,991,916 B2 | 1/2006 | Benson et al. |
| 6,997,920 B2 | 2/2006 | Mann et al. |
| 7,011,630 B2 | 3/2006 | Desai et al. |
| 7,013,177 B1 | 3/2006 | Whitehurst et al. |
| 7,018,384 B2 | 3/2006 | Skakoon |
| 7,018,568 B2 | 3/2006 | Tierney |
| 7,024,236 B2 | 4/2006 | Ford et al. |
| 7,024,245 B2 | 4/2006 | Lebel et al. |
| 7,024,248 B2 | 4/2006 | Penner et al. |
| 7,025,743 B2 | 4/2006 | Mann et al. |
| 7,025,760 B2 | 4/2006 | Miller et al. |
| 7,027,856 B2 | 4/2006 | Zhou et al. |
| 7,027,871 B2 | 4/2006 | Burnes et al. |
| 7,033,338 B2 | 4/2006 | Vilks et al. |
| 7,041,704 B2 | 5/2006 | Burgard et al. |
| 7,044,082 B1 | 5/2006 | Hewett et al. |
| 7,052,483 B2 | 5/2006 | Wojcik |
| 7,054,782 B2 | 5/2006 | Hartlaub |
| 7,058,447 B2 | 6/2006 | Hill et al. |
| 7,063,684 B2 | 6/2006 | Moberg |
| 7,066,891 B2 | 6/2006 | Stadler et al. |
| 7,066,909 B1 | 6/2006 | Peter et al. |
| 7,069,078 B2 | 6/2006 | Houben |
| 7,072,802 B2 | 7/2006 | Hartlaub |
| 7,074,233 B1 | 7/2006 | Gowda et al. |
| 7,084,116 B2 | 8/2006 | Fraser et al. |
| 7,092,753 B2 | 8/2006 | Darvish et al. |
| 7,094,228 B2 | 8/2006 | Zhang et al. |
| 7,101,857 B2 | 9/2006 | Sung et al. |
| 7,107,086 B2 | 9/2006 | Reihl et al. |
| 7,107,093 B2 | 9/2006 | Burnes |
| 7,108,696 B2 | 9/2006 | Daniel et al. |
| 7,109,878 B2 | 9/2006 | Mann et al. |
| 7,115,606 B2 | 10/2006 | Landau et al. |
| 7,123,968 B1 | 10/2006 | Casscells, III et al. |
| 7,125,407 B2 | 10/2006 | Edwards et al. |
| 7,125,848 B2 | 10/2006 | Fraser et al. |
| 7,133,329 B2 | 11/2006 | Skyggebjerg et al. |
| 7,149,581 B2 | 12/2006 | Goedeke |
| 7,149,773 B2 | 12/2006 | Haller et al. |
| 7,150,975 B2 | 12/2006 | Tamada et al. |
| 7,151,961 B2 | 12/2006 | Whitehurst et al. |
| 7,160,252 B2 | 1/2007 | Cho et al. |
| 7,162,303 B2 | 1/2007 | Levin et al. |
| 7,162,307 B2 | 1/2007 | Patrias |
| 7,163,511 B2 | 1/2007 | Conn et al. |
| 7,164,948 B2 | 1/2007 | Struble et al. |
| 7,167,743 B2 | 1/2007 | Heruth et al. |
| 7,171,263 B2 | 1/2007 | Darvish et al. |

(56) References Cited

U.S. PATENT DOCUMENTS

| | | |
|---|---|---|
| 7,171,274 B2 | 1/2007 | Starkweather et al. |
| 7,179,226 B2 | 2/2007 | Crothall et al. |
| 7,181,505 B2 | 2/2007 | Haller et al. |
| 7,184,828 B2 | 2/2007 | Hill et al. |
| 7,184,829 B2 | 2/2007 | Hill et al. |
| 7,186,247 B2 | 3/2007 | Ujhelyi et al. |
| 7,187,979 B2 | 3/2007 | Haubrich et al. |
| 7,190,997 B1 | 3/2007 | Darvish et al. |
| 7,191,008 B2 | 3/2007 | Schmidt et al. |
| 7,193,521 B2 | 3/2007 | Moberg et al. |
| 7,203,541 B2 | 4/2007 | Sowelam et al. |
| 7,206,632 B2 | 4/2007 | King |
| 7,209,784 B2 | 4/2007 | Schmidt |
| 7,209,790 B2 | 4/2007 | Thompson et al. |
| 7,218,964 B2 | 5/2007 | Hill et al. |
| 2001/0022279 A1 | 9/2001 | Denyer et al. |
| 2001/0047195 A1 | 11/2001 | Crossley |
| 2002/0026141 A1 | 2/2002 | Houben et al. |
| 2002/0032406 A1 | 3/2002 | Kusleika |
| 2002/0038101 A1 | 3/2002 | Avrahami et al. |
| 2002/0040208 A1 | 4/2002 | Flaherty et al. |
| 2002/0068869 A1 | 6/2002 | Brisken et al. |
| 2002/0072743 A1 | 6/2002 | KenKnight et al. |
| 2002/0077673 A1 | 6/2002 | Penner et al. |
| 2002/0082583 A1 | 6/2002 | Lerner |
| 2002/0082665 A1 | 6/2002 | Haller et al. |
| 2002/0102707 A1 | 8/2002 | Harrow et al. |
| 2002/0106410 A1 | 8/2002 | Masters |
| 2002/0133148 A1 | 9/2002 | Daniel et al. |
| 2002/0137014 A1 | 9/2002 | Anderson et al. |
| 2002/0176849 A1 | 11/2002 | Slepian |
| 2002/0177689 A1 | 11/2002 | Benson et al. |
| 2002/0177772 A1 | 11/2002 | Altman et al. |
| 2002/0177782 A1 | 11/2002 | Penner |
| 2002/0183682 A1 | 12/2002 | Darvish et al. |
| 2002/0183686 A1 | 12/2002 | Darvish et al. |
| 2003/0028089 A1* | 2/2003 | Galley et al. ............... 600/365 |
| 2003/0040683 A1 | 2/2003 | Rule et al. |
| 2003/0060753 A1 | 3/2003 | Starkweather et al. |
| 2003/0060765 A1* | 3/2003 | Campbell et al. ............ 604/131 |
| 2003/0069614 A1 | 4/2003 | Bowman et al. |
| 2003/0073609 A1 | 4/2003 | Pinkerton |
| 2003/0100885 A1 | 5/2003 | Pettis et al. |
| 2003/0130616 A1 | 7/2003 | Steil et al. |
| 2003/0144712 A1 | 7/2003 | Streeter |
| 2003/0167033 A1 | 9/2003 | Chen et al. |
| 2003/0171401 A1 | 9/2003 | Johnson et al. |
| 2003/0176933 A1 | 9/2003 | Lebel et al. |
| 2003/0181852 A1 | 9/2003 | Mann et al. |
| 2003/0181894 A1 | 9/2003 | Neuberger |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0208152 A1 | 11/2003 | Avrahami et al. |
| 2003/0212364 A1 | 11/2003 | Mann et al. |
| 2003/0212441 A1 | 11/2003 | Starkweather et al. |
| 2003/0231990 A1 | 12/2003 | Faries et al. |
| 2004/0014131 A1 | 1/2004 | Benson et al. |
| 2004/0024361 A1 | 2/2004 | Fago et al. |
| 2004/0028707 A1 | 2/2004 | Pinkerton |
| 2004/0030282 A1 | 2/2004 | Freyman et al. |
| 2004/0059328 A1 | 3/2004 | Daniel et al. |
| 2004/0062148 A1 | 4/2004 | Skyggebjerg et al. |
| 2004/0063200 A1 | 4/2004 | Chaikof et al. |
| 2004/0064086 A1 | 4/2004 | Gottlieb et al. |
| 2004/0064127 A1 | 4/2004 | Lerner |
| 2004/0064133 A1 | 4/2004 | Miller et al. |
| 2004/0073190 A1 | 4/2004 | Deem et al. |
| 2004/0082639 A1 | 4/2004 | Ho et al. |
| 2004/0085215 A1 | 5/2004 | Moberg et al. |
| 2004/0092885 A1 | 5/2004 | Duchon et al. |
| 2004/0098113 A1 | 5/2004 | Forsell et al. |
| 2004/0111132 A1 | 6/2004 | Shenderova et al. |
| 2004/0127895 A1 | 7/2004 | Flock et al. |
| 2004/0142034 A1 | 7/2004 | Thor et al. |
| 2004/0147872 A1 | 7/2004 | Thompson |
| 2004/0157884 A1 | 8/2004 | Johnson et al. |
| 2004/0171518 A1 | 9/2004 | Van Antwerp et al. |
| 2004/0186533 A1 | 9/2004 | Greenberg et al. |
| 2004/0193090 A1 | 9/2004 | Lebel et al. |
| 2004/0198822 A1 | 10/2004 | Fraser et al. |
| 2004/0202692 A1 | 10/2004 | Shanley et al. |
| 2004/0209869 A1 | 10/2004 | Landau et al. |
| 2004/0209960 A1 | 10/2004 | Burgard et al. |
| 2004/0210267 A1 | 10/2004 | Lebel et al. |
| 2004/0220551 A1 | 11/2004 | Flaherty et al. |
| 2004/0225338 A1 | 11/2004 | Lebel et al. |
| 2004/0230117 A1 | 11/2004 | Tosaya et al. |
| 2004/0236269 A1 | 11/2004 | Marchitto et al. |
| 2004/0248979 A1 | 12/2004 | Brettman et al. |
| 2004/0260239 A1 | 12/2004 | Kusleika |
| 2004/0265353 A1 | 12/2004 | Zhang et al. |
| 2005/0004663 A1 | 1/2005 | Llanos et al. |
| 2005/0008580 A1 | 1/2005 | Gong et al. |
| 2005/0009735 A1 | 1/2005 | Kim et al. |
| 2005/0015055 A1 | 1/2005 | Yang |
| 2005/0020577 A1 | 1/2005 | Landau et al. |
| 2005/0026909 A1 | 2/2005 | Landau et al. |
| 2005/0033148 A1 | 2/2005 | Haueter et al. |
| 2005/0033231 A1 | 2/2005 | Powell |
| 2005/0033370 A1 | 2/2005 | Jelen et al. |
| 2005/0054725 A1 | 3/2005 | Thor et al. |
| 2005/0059938 A1 | 3/2005 | Malisch |
| 2005/0065464 A1 | 3/2005 | Talbot et al. |
| 2005/0065465 A1 | 3/2005 | Lebel et al. |
| 2005/0065556 A1 | 3/2005 | Reghabi et al. |
| 2005/0084477 A1 | 4/2005 | Van Antwerp et al. |
| 2005/0090866 A1 | 4/2005 | Miller et al. |
| 2005/0107353 A1 | 5/2005 | Burgard et al. |
| 2005/0107738 A1 | 5/2005 | Slater et al. |
| 2005/0107743 A1 | 5/2005 | Fangrow |
| 2005/0113798 A1 | 5/2005 | Slater et al. |
| 2005/0124560 A1 | 6/2005 | Sung et al. |
| 2005/0137670 A1 | 6/2005 | Christopherson et al. |
| 2005/0143636 A1 | 6/2005 | Zhang et al. |
| 2005/0148955 A1 | 7/2005 | Chong et al. |
| 2005/0171160 A1 | 8/2005 | Edgar et al. |
| 2005/0171513 A1 | 8/2005 | Mann et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0187140 A1 | 8/2005 | Hunter et al. |
| 2005/0192637 A1 | 9/2005 | Girouard et al. |
| 2005/0196421 A1 | 9/2005 | Hunter et al. |
| 2005/0208095 A1 | 9/2005 | Hunter et al. |
| 2005/0217674 A1 | 10/2005 | Burton et al. |
| 2005/0220836 A1 | 10/2005 | Falotico et al. |
| 2005/0221270 A1 | 10/2005 | Connelly et al. |
| 2005/0222191 A1 | 10/2005 | Falotico et al. |
| 2005/0228049 A1 | 10/2005 | Thor et al. |
| 2005/0229931 A1 | 10/2005 | Denyer et al. |
| 2005/0232964 A1 | 10/2005 | Fennimore |
| 2005/0232965 A1 | 10/2005 | Falotico |
| 2005/0239838 A1 | 10/2005 | Edgar et al. |
| 2005/0239890 A1 | 10/2005 | Fraser et al. |
| 2005/0245840 A1 | 11/2005 | Christopherson et al. |
| 2005/0249775 A1 | 11/2005 | Falotico et al. |
| 2005/0249776 A1 | 11/2005 | Chen et al. |
| 2005/0256165 A1 | 11/2005 | Edgar et al. |
| 2005/0256499 A1 | 11/2005 | Pettis et al. |
| 2005/0267550 A1 | 12/2005 | Hess et al. |
| 2005/0270245 A1 | 12/2005 | Villaseca et al. |
| 2005/0272719 A1 | 12/2005 | Landau et al. |
| 2005/0272806 A1 | 12/2005 | Falotico et al. |
| 2005/0276842 A1 | 12/2005 | Zhang et al. |
| 2005/0282799 A1 | 12/2005 | Landau et al. |
| 2005/0282859 A1 | 12/2005 | Thor |
| 2006/0025663 A1 | 2/2006 | Talbot et al. |
| 2006/0025756 A1 | 2/2006 | Francischelli et al. |
| 2006/0030837 A1 | 2/2006 | McKenna et al. |

(56) References Cited

U.S. PATENT DOCUMENTS

| | | | |
|---|---|---|---|
| 2006/0030838 A1* | 2/2006 | Gonnelli | 604/890.1 |
| 2006/0031094 A1 | 2/2006 | Cohen et al. | |
| 2006/0063754 A1 | 3/2006 | Edgar et al. | |
| 2006/0063755 A1 | 3/2006 | Edgar et al. | |
| 2006/0063928 A1 | 3/2006 | Edgar et al. | |
| 2006/0079858 A1 | 4/2006 | Miller et al. | |
| 2006/0079941 A1 | 4/2006 | Ovsyshcher et al. | |
| 2006/0094705 A1 | 5/2006 | Edgar et al. | |
| 2006/0111704 A1 | 5/2006 | Brenneman et al. | |
| 2006/0122666 A1 | 6/2006 | Nghiem et al. | |
| 2006/0122863 A1 | 6/2006 | Gottesman et al. | |
| 2006/0129050 A1 | 6/2006 | Martinson et al. | |
| 2006/0129225 A1 | 6/2006 | Kopia et al. | |
| 2006/0142819 A1 | 6/2006 | Penner et al. | |
| 2006/0149218 A1 | 7/2006 | Slater et al. | |
| 2006/0149339 A1 | 7/2006 | Burnes et al. | |
| 2006/0173406 A1 | 8/2006 | Hayes et al. | |
| 2006/0173444 A1 | 8/2006 | Choy et al. | |
| 2006/0184092 A1 | 8/2006 | Atanasoska et al. | |
| 2006/0184154 A1 | 8/2006 | Moberg et al. | |
| 2006/0188575 A1 | 8/2006 | Thor et al. | |
| 2006/0247311 A1 | 11/2006 | Fraser et al. | |
| 2006/0253085 A1 | 11/2006 | Geismar et al. | |
| 2006/0264509 A1 | 11/2006 | Fraser et al. | |
| 2006/0264894 A1 | 11/2006 | Moberg et al. | |
| 2006/0270968 A1 | 11/2006 | Greenberg et al. | |
| 2006/0271020 A1 | 11/2006 | Huang et al. | |
| 2006/0271112 A1 | 11/2006 | Martinson et al. | |
| 2006/0272652 A1 | 12/2006 | Stocker et al. | |
| 2006/0276542 A1 | 12/2006 | Fraser et al. | |
| 2006/0293309 A1 | 12/2006 | Thor et al. | |
| 2007/0003549 A1 | 1/2007 | Ignatovich et al. | |
| 2007/0004752 A1 | 1/2007 | Coughlin et al. | |
| 2007/0009956 A1 | 1/2007 | Srinivas et al. | |
| 2007/0016163 A1 | 1/2007 | Santini et al. | |
| 2007/0016170 A1 | 1/2007 | Kovelman | |
| 2007/0026042 A1 | 2/2007 | Narayanan | |
| 2007/0030764 A1 | 2/2007 | Skyggebjerg et al. | |
| 2007/0033074 A1 | 2/2007 | Nitzan et al. | |
| 2007/0038100 A1 | 2/2007 | Nita | |
| 2007/0040449 A1 | 2/2007 | Spurlin et al. | |
| 2007/0048350 A1 | 3/2007 | Falotico et al. | |
| 2007/0051362 A1 | 3/2007 | Sullivan et al. | |
| 2007/0053996 A1 | 3/2007 | Boyden et al. | |
| 2007/0054319 A1 | 3/2007 | Boyden et al. | |
| 2007/0054871 A1 | 3/2007 | Pastore et al. | |
| 2007/0060652 A1 | 3/2007 | Fraser et al. | |
| 2007/0060864 A1 | 3/2007 | Redding | |
| 2007/0060871 A1 | 3/2007 | Istoc et al. | |
| 2007/0083258 A1 | 4/2007 | Falotico et al. | |
| 2007/0087315 A1 | 4/2007 | Stuart et al. | |
| 2007/0088248 A1 | 4/2007 | Glenn et al. | |
| 2007/0093752 A1* | 4/2007 | Zhao et al. | 604/131 |
| 2007/0098753 A1 | 5/2007 | Falotico et al. | |
| 2007/0112298 A1 | 5/2007 | Mueller et al. | |
| 2007/0219480 A1 | 9/2007 | Kamen et al. | |
| 2008/0023593 A1 | 1/2008 | Ritota et al. | |
| 2008/0200897 A1 | 8/2008 | Hoss et al. | |
| 2008/0281297 A1 | 11/2008 | Pesach et al. | |
| 2010/0057003 A1* | 3/2010 | Dos Santos | 604/114 |
| 2010/0106088 A1 | 4/2010 | Yodfat et al. | |
| 2010/0174225 A1 | 7/2010 | Pesach et al. | |
| 2010/0286467 A1 | 11/2010 | Pesach et al. | |
| 2010/0292557 A1 | 11/2010 | Pesach et al. | |
| 2010/0318035 A1 | 12/2010 | Edwards et al. | |
| 2011/0184342 A1 | 7/2011 | Pesach et al. | |
| 2011/0288527 A1 | 11/2011 | Pesach et al. | |

FOREIGN PATENT DOCUMENTS

| | | |
|---|---|---|
| EP | 1752174 A1 | 2/2007 |
| FR | 2795629 | 1/2001 |
| WO | WO-00/18339 | 4/2000 |
| WO | WO-00/23132 | 4/2000 |
| WO | WO-00/32259 | 6/2000 |
| WO | WO-00/74763 | 12/2000 |
| WO | WO-00/78212 A1 | 12/2000 |
| WO | WO-01/01852 | 1/2001 |
| WO | WO-01/47408 | 7/2001 |
| WO | WO-01/93931 | 12/2001 |
| WO | WO-02/068028 | 9/2002 |
| WO | WO-03/055384 | 7/2003 |
| WO | WO-03/086534 | 10/2003 |
| WO | WO-2006/049570 A2 | 5/2006 |
| WO | WO-2006/084464 | 8/2006 |
| WO | WO-2006/091650 A2 | 8/2006 |
| WO | WO-2008/051924 A2 | 5/2008 |
| WO | WO-2008/114218 | 9/2008 |
| WO | WO-2008/114220 | 9/2008 |
| WO | WO-2008/114223 | 9/2008 |
| WO | WO-2008/114224 | 9/2008 |
| WO | WO-2009/081262 | 7/2009 |
| WO | WO-2010/052579 | 5/2010 |

OTHER PUBLICATIONS

Bos et al., Biomaterials (2005), 26:3901-3909.
Clarke et. al., (2005), Diabetes Care, 28:2412-2417.
Facchinetti et. al., (2007), Journal of Diabetes Science and Technology, 1:617-623.
Heinemann, (2002), Diabetes Technology & Therapeutics, 5:673-682.
Koivisto et al. (1980), British Medical Journal, 280:1411-1413.
Koivisto et al., (1978), The New England Journal of Medicine, 298:79-83.
Magerl et. al., (1996), Journal of Physiology, 497:837-848.
Midttun et. al., (1996), Clinical Physiology, 16:259-274.
Rebrin et al., (2000), Diabetes Technology and Therapeutics, 2:461-472.
Shumaker et al., (2006), Lasers in Surgery and Medicine, 38:211-217.
Sindelka et al., (1994), Diabetologia, 37:377-380.
European Search Report for EP1315647 mailed Jul. 26, 2013.

* cited by examiner

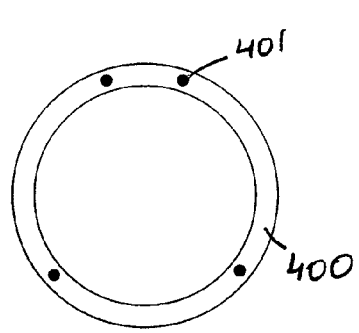
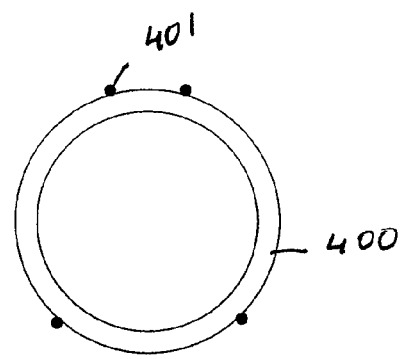
Figure 3
Figure 4
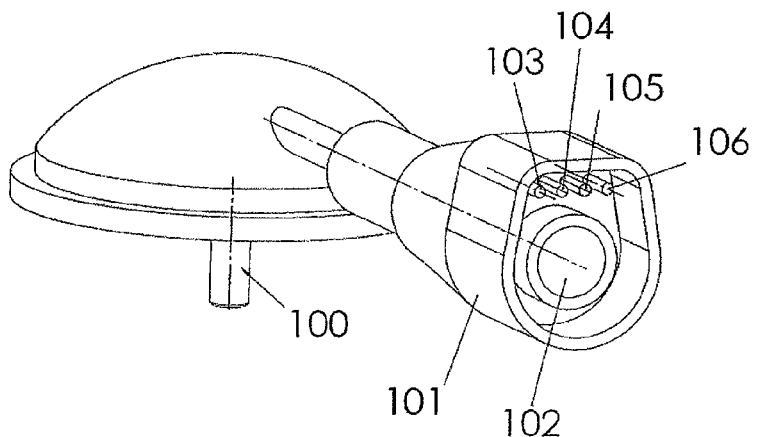
Figure 5

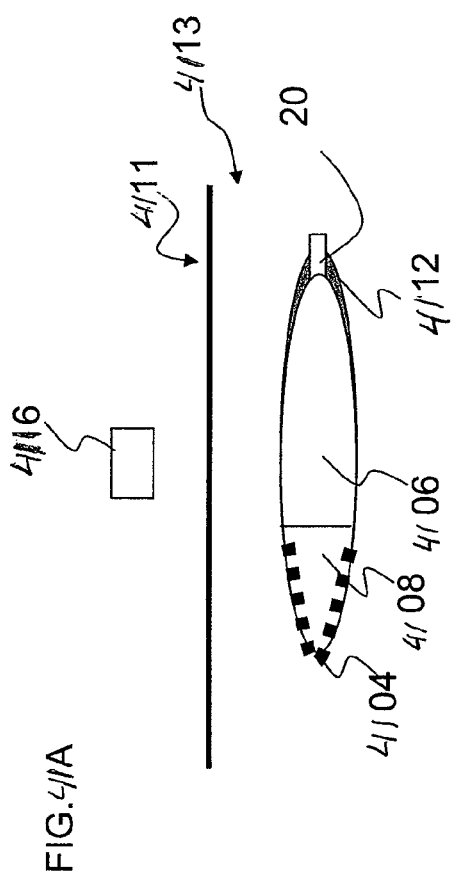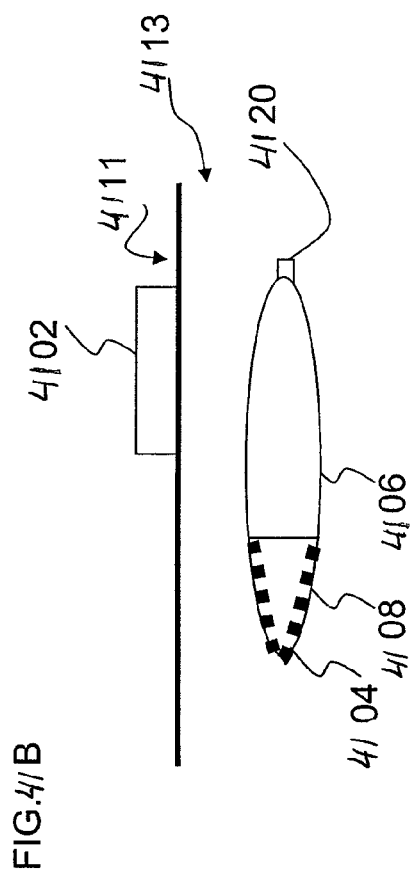
FIG.41A
FIG.41B

METHOD AND DEVICE FOR DRUG DELIVERY

CROSS REFERENCE TO RELATED APPLICATIONS

This application claims priority to, and is a national stage application, filed in accordance with 35 U.S.C. 371, based on the International Patent Application No. PCT/IB2008/051044, to Benny Pesach et al., filed Mar. 19, 2008, and entitled "METHOD AND DEVICE FOR DRUG DELIVERY", which claims priority to U.S. Provisional Patent Application Ser. No. 60/895,518, filed Mar. 19, 2007, U.S. Provisional Patent Application Ser. No. 60/895,519, filed Mar. 19, 2007, U.S. Provisional Patent Application Ser. No. 60/912,698, filed Apr. 19, 2007, U.S. Provisional Patent Application Ser. No. 60/940,721, filed May 30, 2007, U.S. Utility patent application Ser. No. 11/821,230, filed Jun. 21, 2007, U.S. Provisional Patent Application Ser. No. 61/008,278, filed Dec. 18, 2007, U.S. Provisional Patent Application Ser. No. 60/956,700, filed Aug. 19, 2007, U.S. Provisional Patent Application Ser. No. 60/970,997, filed Sep. 10, 2007, U.S. Provisional Patent Application Ser. No. 61/008,325, filed Dec. 18, 2007, U.S. Provisional Patent Application Ser. No. 61/008,274, filed Dec. 18, 2007, and U.S. Provisional Patent Application No. 61/008,277, filed Dec. 18, 2007, and is a continuation-in-part of U.S. Utility patent application Ser. No. 11/821,230, filed Jun. 21, 2007. Each of the foregoing disclosures are incorporated by reference herein in its entirety.

BACKGROUND OF THE INVENTION

1. Field of the Invention

The present invention relates to systems and methods for delivering drugs to a patient. In particular, the present invention relates to systems and methods for subcutaneous infusion of drugs or substances and using energy sources to improve effectiveness of the infused drugs.

2. Background of the Invention

Diabetes is a very serious illness affecting millions of people today. Many diabetic patients require injection of insulin to maintain proper levels of glucose in their blood in order to survive. Such injections of insulin are done using drug delivery systems.

Many medical treatment systems and methods involve drug delivery systems that employ subcutaneous infusions of therapeutic fluids, drugs, proteins, and other compounds. Such delivery systems and methods, especially in the area of insulin delivery, have made use of subcutaneous catheters and continuous subcutaneous insulin infusion (CSII) pumps. In conventional insulin pumps, the pump is configured to be attached to a disposable thin plastic tube or a catheter through which insulin passes into the tissue. The catheter can be inserted transcutaneously, typically on the patient's abdomen, and is changed every two to three days. New types of insulin pumps, such as the OmniPod pump manufactured by Insulet Corporation, do not have an external catheter and, but rather, a catheter port that is embedded into the pump mechanism.

In many instances, the patients require insulin delivery around the clock to keep proper levels of glucose in their blood. Insulin can be delivered at a basal rate or in bolus doses. The basal rate represents insulin that is continuously delivered to the patient. Such continuous delivery of insulin keeps patient's blood glucose in the desired range between meals and over night. The bolus dose is an amount of insulin delivered to the patient matching a dose of carbohydrates consumed by the patient to address increased glucose levels as a result of the ingested food. Some conventional pump mechanisms are configured to react upon command, or by way of an algorithm, to the increase in glucose levels by delivering a bolus dose of insulin that matches the rise in the level of glucose and prevents large glucose excursions. However, many conventional subcutaneous drug delivery systems are incapable of quickly matching or preventing the rise of blood glucose. The delay in such matching is also true in case of the "rapid-acting" insulin. Some of the reasons for this delay include a lag in the absorption of insulin from the injection site and the time it takes for complex insulin molecules to break down into monomers.

Additionally, since blood glucose levels rise immediately following the meal, the delay in matching insulin to the rising levels causes post prandial hyperglycemic events (i.e., when levels of blood glucose are above normal) to occur. Further, occasionally after a certain period of time passes (e.g., 2-3 hours) after a meal, the blood glucose levels drop yet insulin concentrations in the blood rise followed by the peak of the systemic insulin effect and result in causing hypoglycemic events (i.e., when levels of blood glucose are below normal) to occur. Both hyperglycemic and hypoglycemic events are highly undesirable. Additionally, since the local blood perfusion at the insulin infusion region has large variations depending on the ambient temperature and other parameters, it induces large variations to said delay of the peak of time profile of the insulin action. Those variations in the insulin peak action period further increase the variability in the blood glucose level.

Thus, it is desirable to provide a system and a method that provides efficient and timely delivery of the drug to the patient. In particular, it is desirable to provide a system and a method for delivering insulin to the patient that improves effectiveness of insulin in the blood to maintain normal levels of blood glucose and prevent or reduce hyperglycemic and hypoglycemic events.

SUMMARY OF THE INVENTION

Embodiments of the present invention relate to systems, devices and methods for delivery of drugs, substances and/or chemicals (together "drugs" or "substances") to a patient and for improving the effectiveness of such drugs once they are delivered. In some embodiments, of the present invention, a device for improving performance of catheter-based drug delivery devices is provided. The catheter can be an adjunct to a pump or embedded into the pump mechanism. In such embodiments, the device can be applied to the vicinity of the tissue region of the patient into which a drug (e.g., insulin) is delivered, to expose the tissue region to a treatment as heat, cooling, temperature control, mechanical vibrations, suction, massaging, acoustic stimulation (e.g., ultrasound), electromagnetic radiation, electric field, magnetic field, radio frequency irradiation, microwave irradiation, electrical stimulation, or the like, or any combination of the above treatments to improve the drug's pharmacokinetic and for pharmacodynamic profile. The tissue treatment element may stimulate or inhibit tissue by introducing secondary substances for example including but not limited to drugs, medicament, chemical, biologically active bacteria, biologically inactive bacteria or the like or also any combination of the above treatments to improve the drug's pharmacokinetic and/or pharmacodynamic profile.

Such a device, according to some embodiments of the present invention, can also be part of a catheter which has one section inside the tissue and another section that connects to a unit outside the tissue (i.e., a transcutaneous delivery system). As can be understood by one skilled in the art, properties (such as amplitude, phase, frequency, etc.) of the individual excitation source(s), the combination of excitation sources, the relative ratio and timing between the various excitation sources, may be controlled by a processor in order to achieve a desired response of the tissue region next to the catheter. The sources can also be adjusted according to the chemical/physical properties of the infused substance.

In some embodiments, of the present invention, a device for supplying energy to a tissue region (or infused region) can be configured to monitor and control the properties of the excitation sources (such as amplitude, phase, intensity, frequency, etc.). Based on the monitoring, the information can be provided to a controller ("controller", also referred to as a "processing unit") that uses the information to reduce the variability of the drug delivery process. In such embodiments, the device can be configured to monitor properties of the tissue next to the catheter element (e.g., such as temperature). Based on such monitoring, the information can be provided to the controller that utilizes the information to improve the pharmacokinetic and/or pharmacodynamic profile of the drug in the desired direction as well as performance and reduce variability of the drug delivery process.

The device according to some embodiments of the present invention can be configured to either automatically detect the drug delivery through the catheter by the delivery apparatus, get a signal from the drug delivery device, get the signal from a separate button or switch to initiate a protocol of exposing the infused tissue region to the above described treatments or tissue stimulations. The device can then be configured to begin operating by applying a stimulation or a treatment to the tissue. The tissue response to the stimulation enhances the functionality of a drug delivery pump by enhancing the kinetics of molecule transport between the catheter tip placed inside the tissue to the various compartments of the tissue region around it and to the blood system.

In some embodiments, the applied treatment may reduce the variability of the drug absorption in the blood or lymph system and its local and systemic effects. For example, heating the tissue region in the vicinity of the area of drug delivery (i.e., infused region) to a preset regulated temperature during the drug infusion and absorption into the blood may make local blood perfusion at that region more reproducible and the drug absorption process more uniform and reproducible as well. Also, by reducing the delay between the drug delivery into the tissue and absorption into the blood system, the variability of the drug action induced by the delayed profile can be reduced. The temperature of the region adjacent to the infusion region can be regulated for longer periods, but the cost may be the energy source volume and weight. Therefore, for minimization of the energy source size the heating period should be optimized in relation to the period of the drug infusion and absorption into the blood.

In some embodiments, the tissue treatment or stimulation device may be triggered manually by the user. The user may activate the treatment device or devices before or after the pump activation to enhance the tissue response to the delivered drug. In such embodiments, this can be done by pressing a button or a sequence of buttons on the tissue treatment device. In some embodiments, in case of communication between the drug delivery device and the treatment device, the treatment can be triggered manually by pressing a button or a sequence of buttons on the drug delivery device. For example, in case of an insulin pump, the pump may have a special button for triggering a "fast bolus" compared to the other bolus options provided by the pump. The fast insulin bolus mode can be configured to start one of the disclosed treatments in parallel to application of the insulin bolus infusion for a given period of time, such as 30 minutes (for example). This improves or modifies (in an advantageous manner) insulin's pharmacokinetics or pharmacodynamics, tissue blood perfusion and/or absorption in the blood and is highly attractive in conjunction with high glycemic index food. Application of a "fast bolus" may be useful in consumption of high glycemic index food where larger rapid glucose excursions occurs, but also in most of the cases of using insulin boluses for prandial coverage. Application of a "fast bolus" can be initiated by pressing a special sequence of buttons or choosing a bolus mode using the pump display and buttons. In some embodiments, the user may trigger the tissue treatment or stimulation before the application of the bolus to further improve the treatment effect. In some embodiments, the user may trigger the tissue treatment or stimulation together with the infusion of the insulin bolus before the meal to further increase the treatment effect. In some embodiments, the tissue treatment or stimulation may be triggered after the bolus to save battery life.

Some embodiments of the present invention also provide methods for monitoring tissue parameters non-invasively or invasively using the catheter or both invasively and non-invasively, and using the information to control activation of the device of the present invention Some embodiments of the present invention also provide methods for improving or modifying a drug's pharmacokinetic and/or pharmacodynamic profile in order to reduce time to peak action in the blood of the injected material by applying a modulation pattern to the pump. With this modulation, the infusion fluid is slightly pulled in and out of the tissue during or after the drug infusion process. In such embodiments, this method may not require an addition of any other devices to the current infusion pump rather it can be configured to modulate drug flow from the drug delivery element or pump.

In some embodiments, a drug delivery pump may be mechanically or electronically connected to the catheter of the above-noted device embodiments. In such embodiments, the catheter unit includes at least one of the following excitation sources or at least one combination of two such sources from the following: a heat source (e.g., a heat resistor), a suction port activated by a pump (for example), a mechanical vibration source, an ultrasound excitation source, an ultrasound transducer, a light source, an optical fiber, a massaging element, electromagnetic radiation source and/or a combination of at least two of sources of heat, vibrations, suction, ultrasound, light, electromagnetic radiation and massaging.

In some embodiments, a device for drug delivery is provided which includes an infusion catheter for insertion into tissue, a drug delivery device for infusing the drug into and within the infusion catheter, a treatment device for applying a specific treatment or stimulation to the drug infused region in order to improve drug's pharmacokinetic, pharmacodynamic profile and/or to increase blood perfusion in that region during the drug delivery period to improve drug absorption into the blood system.

In some embodiments, a device for drug delivery is provided which includes an infusion catheter for insertion into tissue, a drug delivery device for infusing a drug into the infusion catheter, a treatment device for applying a specific treatment or stimulation to the drug infused region in order to improve, modify and/or stabilize the drug pharmacokinetics, pharmacodynamics, and/or to reduce variations of the drug absorption into the blood system.

In some embodiments, a device for drug delivery is provided and includes an infusion catheter for insertion into tissue, a drug delivery device for infusing a drug into the infusion catheter, a treatment device for applying a specific treatment or stimulation to the drug infused region to improve, modify and/or stabilize the drug's pharmacokinetics, pharmacodynamics and/or to reduce variations of the drug absorption process into the blood system, at least one sensor to measure the effect of the treatment device, and a control unit to control the operation of the treatment device using the information from the at least one sensor.

In some embodiments, a device for drug delivery is provided and includes an infusion catheter for insertion into tissue, a drug delivery device for infusing a drug into the infusion catheter, a sensor for detecting drug infusion through the catheter either directly or indirectly, a treatment device for applying a specific treatment to the drug infused region to improve, modify and/or stabilize the drug pharmacokinetics, pharmacodynamics and/or to reduce variations of the drug absorption process into the blood system, and a control unit for initiating a treatment profile with the treatment device after detection of the drug infusion with the sensor.

In some embodiments, a device for drug delivery is provided that includes an infusion catheter for insertion into tissue, a drug delivery device for infusing a drug into the infusion catheter, a housing for the drug delivery device, a sensor built into the housing to sense the operation of the infusion device upon a drug bolus being delivered by the device, a treatment element for applying a specific treatment to the drug infused region to improve, modify and/or to stabilize the drug pharmacokinetics or pharmacodynamics, an electronic control unit connected to the treatment element for initiating a treatment profile with the treatment element when the drug delivery device starts drug infusion. In some such embodiments, the unit is built into the housing.

In some embodiments, a device for drug delivery is provided that includes a drug delivery device, an infusion catheter for insertion into tissue. The infusion catheter is part of an infusion set including: an infusion catheter, a tube with or without connections that connects the infusion catheter to the drug delivery device, a treatment element for applying a specific treatment to the drug infused region of the tissue to improve, modify and/or stabilize the drug pharmacokinetics or pharmacodynamics, an adhesive element that is used to secure the treatment element and/or the infusion catheter to a position over the tissue, a communication channel between the drug delivery device and the treatment element, a control unit (i.e., a controller/processing unit) that initiates a treatment profile with the treatment element when the drug delivery device starts drug infusion. The elements of the device may be all or part contained in the same housing.

In some embodiments, a device for drug delivery is provided which includes a drug delivery device, and an infusion catheter for insertion into a tissue. The infusion catheter may be part of an infusion set including: an infusion catheter, a tube with or without connections that connects the infusion catheter to the drug delivery device, a treatment element for applying a specific treatment to the drug infused region of the tissue to improve, modify and/or stabilize the drug pharmacokinetics and/or pharmacodynamics, an adhesive element for securing the treatment element and/or the infusion catheter to a position over the tissue, a housing for the drug delivery device, a pickup coil or other sensor built into the housing to sense the operation of the infusion device when a bolus dose is delivered by the device, and a control unit that starts a treatment profile with the treatment element when the drug delivery device starts the drug infusion. The unit is built into the housing.

In some embodiments, a device for drug delivery is provided which includes an infusion catheter for insertion into tissue. The infusion catheter may be part of an infusion set including: an infusion catheter, a tube with or without connections that connects the infusion catheter to the drug delivery device, a treatment element for applying a specific treatment to the drug tissue infused region to improve, modify and/or stabilize the drug pharmacokinetics and/or pharmacodynamics, an adhesive element that is used to secure the treatment element and/or the infusion catheter to a position over the tissue, a housing for the drug delivery device, and a control unit that starts a treatment profile with the treatment element when the drug delivery device starts the drug infusion.

In some such embodiments, the adhesive, the treatment element and the infusion set are disposable while all other components are reusable. In some embodiments, the adhesive, the treatment element, the infusion set and the control unit are disposable while all other components are reusable. In some embodiments, all components including the infusion device and the power source (batteries) are disposable. The above elements of the device in the present invention such as the drug delivery device, the infusion catheter, the treatment device and others may be separate individual elements or elements contained all or part of them in one housing.

Some embodiments of the present invention provide for a device for improving the performance of drug delivery devices by delivering a drug (e.g., insulin) in conjunction with the application of electromagnetic radiation treatment, e.g., from a source of electromagnetic radiation. In some embodiments, the drug delivery device includes a catheter based drug delivery device. Various implementations of the catheter and the drug delivery device are encompassed within the present disclosure. For example and without limitation, the catheter may include an external element to the pump or an element partially or completely embedded into a pump mechanism. The device described herein can be part of the catheter which has one section inserted inside the tissue and another section that connects to a unit outside the tissue.

The electromagnetic radiation treatment is, in some embodiments, applied to a tissue region to which the drug is delivered to expose it to electromagnetic radiation and/or to an effect caused by electromagnetic radiation to improve the drug pharmacokinetics or pharmacodynamics. The effect may include, for example, acoustical stimulation through application of electromagnetic radiation, light based stimulation and the like.

The radiation source properties, or the combination of a radiation source and another stimulation source as described in at least U.S. Provisional Application Nos. 60/912,698, 60/895,519, 60/956,700, 61/008,325, 61/008,277, 60/940, 721, and 61/008,278, the disclosures of which are incorporated herein by reference in their entireties as if fully set forth herein, may be controlled by a controller to achieve a desired response of the tissue region next to the catheter. Such adjustment to the chemical/physical properties of the infused substance may also be made. Furthermore, one or more adjustments may be made according to the properties of each stimulation source (such as amplitude, phase, frequency and the like) as well as the relative ratio and timing between the various stimulation sources.

The present disclosure also provides, in some embodiments, a method for monitoring the properties of the stimulation or the properties of the stimulated tissue region. such monitoring is performed through a monitor which provides data and/or feedback to the above controller. The controller uses the information to reduce the variability of the drug delivery process, for example to improve the pharmacokinetic and/or pharmacodynamic profile of the drug as well as performance and reduce variability of the drug delivery process.

In some embodiments, monitoring may be performed by monitoring the properties of the tissue next to the catheter element (including but not limited to tissue blood perfusion, temperature, concentration of one or more blood components) and/or monitoring the resultant effect of stimulating the tissue, for example, monitoring the back reflected radiation from the tissue.

In some embodiments, drug delivery is performed through a delivery apparatus, which may be any type of delivery apparatus known in the art. In some embodiments, the device receives information regarding drug delivery. Such information may be provided through automatic detection of drug delivery through the catheter by the delivery apparatus and/or by receiving a separate signal from the drug delivery device or from a separate button or switch. Regardless of how detection is performed, detection of drug delivery is used to initiate a protocol of exposing the infused tissue region to the above described radiation treatments or tissue stimulations.

Upon detection, the source of electromagnetic radiation applies electromagnetic radiation to the tissue to be treated. The tissue response to the stimulation enhances the functionality of the drug delivery pump by, for example and without being limited by a single hypothesis, enhancing the kinetics of molecular transport from the catheter tip placed inside the tissue to the various compartments of the tissue region around it and to the blood system. In some embodiments, the applied electromagnetic radiation reduces the variability of the drug absorption in the blood system and its effect.

The present disclosure further describes, in some embodiments, a device for drug delivery including an infusion catheter inserted into the tissue, a drug delivery device that infuses the drug into the infusion catheter, a treatment device that applies radiation to the drug infused region to improve the drug pharmacokinetics or pharmacodynamics stabilization to reduce variations of the drug absorption process into the blood system, at least one sensor to measure the effect of the treatment device, and a control unit to control the operation of the treatment device using the information from the at least one sensor.

The present disclosure further describes, in some embodiments, a device for drug delivery including an infusion catheter inserted into the tissue, a drug delivery device that infuses the drug into the infusion catheter, a sensor that detects the drug infusion through the catheter either directly or indirectly, a treatment device that applies radiation to the drug infused region to improve the drug pharmacokinetics or pharmacodynamics or to reduce variations of the drug absorption process into the blood system, and a control unit that starts a treatment profile with the treatment device after detection of the drug infusion with the sensor. According to some embodiments, the sensor is built into a housing for the drug delivery device to sense the operation of the infusion device when drug bolus is delivered by the device.

Some of the embodiments include a source of electromagnetic radiation for delivering the electromagnetic radiation as described above.

The device may also include a communication channel between the drug delivery device and the treatment element, and a control unit that starts tissue radiation treatment profile with the treatment element when the drug delivery device starts the drug infusion.

The device may further include a housing for the drug delivery device, a pickup coil or other sensor built into the housing to sense the operation of the infusion device when drug bolus is delivered by the device and a control unit that starts a treatment profile with the treatment element when the drug delivery device starts the drug infusion. The control unit is built, in some embodiments, into the housing.

The adhesive, the treatment element and the infusion set may be disposable while at least one or more other components are reusable. In some embodiments, a plurality of the other components are reusable. In some embodiments, all components are reusable. The control unit may be disposable while all other components are reusable. The infusion device and the power source (batteries) may be disposable.

As used in the present application's specification, the term "drug" is defined to include any pharmaceutically active compound including but not limited to compounds that treat diseases, injuries, undesirable symptoms, and improve or maintain health. The terms "targeted area" or "targeted areas", or "target site", as used herein, are defined to include a systemic bloodstream of a human body, areas of a human body which can be reached by a systemic bloodstream including, but not limited to muscles, brain, liver, kidneys, etc., and body tissue regions proximate a location of an administered drug.

The present application is directed to the delivery of a drug (by way of a non-limiting example—insulin) to treat any chronic or acute condition, for example, diabetes, hypoxia, anemia, cholesterol, stroke, heart or the like.

In some embodiments of the present application the drug is injected with a syringe or mechanical pump or another drug dispensing device which is connected to an injection port combined with tissue treatment element, when the drug is need to be injected and disconnected from said injection port. In some embodiments the injection port include a catheter inserted into the tissue, a securing element attached to the skin and a connector for connecting a syringe or another drug dispensing device.

Some embodiments of the present application provide treatments as described before to the tissue vicinity of drug injection site, injected with regular injections, such as with a syringe and a needle.

Some embodiments of the present invention provide automatic regulation of a measurand level in a user body by controlling the amount of infused drug that influence measured level at the user body. For example, there are many attempts to compose an "artificial pancreas" to control blood glucose level, since the development of continuous glucose monitors. In this case, any delay such as delay of the insulin absorption and action time, any variability in this delay and any variability in the residual insulin level in the body induces an error for the control algorithm that will result in less tight glucose regulation. Thus, by applying tissue treatment to the insulin delivery site as described by the methods and devices in the present application a better accuracy and robustness of a control algorithm that uses glucose sensor readings can be achieved.

Some embodiments of the present invention provide for an implantable drug delivery device for the automatic and direct introduction of a drug to a target site, wherein the drug may be introduced to an implanted compartment from an external drug source. The implantable drug delivery device includes a controller, tissue treatment element, delivery member, and a drug storage compartment. The implantable device may further include an external (not implanted) user interface that provides the user with a database, dosage form, dosage timing, and dosage trigger. The user interface may communicate with the controller using communication protocols for example including but not limited to wireless, cellular, optical, RF, IR or the like. The implantable drug delivery device may further include a sensor that may be implanted with the implanted device.

The drug storage compartment, according to some embodiments, is an internal container or storage site that maintains the drug in useable form until it is required for delivery. The drug dosage compartment may contain sufficient quantities of the drug to last for a prolonged period of time, for example requiring replenishment once every 3 months or so. The drug storage compartment may receive the drug from an external source by direct injection into the compartment. The drug storage compartment may receive the drug from an external source through the drug receiving member, for example including a catheter, such that the drug supply may be replenished when needed. The drug storage compartment may be subdivided into a plurality of storage compartments, for example, for different drugs.

In some embodiments, the controller functions to control the level of drug delivered to the target site. An implanted sensor may be coupled to the controller for further control of the drug dosage and delivery time. The sensor may indicate to the controller the level of a measurand. For example, the measurand may be indicative of the glucose level, cholesterol level or the like, at least partially based on which the controller determines the required treatment protocol, for example including but not limited to the drug dosage to be delivered, timing of the drug delivery or the like.

The sensor may, according to some embodiments, be external to the drug delivery member and used externally to measure a measurand for example the blood glucose level. The external sensor is coupled to a processor for example including but not limited to a mobile telephone, PDA or the like that is able to communicate with the controller of the implanted drug delivery device. Sensor data is communicated to the implanted controller using at least one communication protocols for example including but not limited to cellular, wireless, IR, optical, RF or the like communication protocols. For example the sensor data is a measurand that may be indicative of the glucose level, cholesterol level or the like. Based on the communicated sensor data, the controller determines the required treatment protocol for example including but not limited to the drug dosage, timing and tissue treatment required relative to the measured data.

In some embodiments, the controller activates or deactivates the tissue treatment element to bring about a desired stimulatory or inhibitory effect that may maximize or minimize drug delivery to the target site. When the drug storage compartment requires replenishment, the controller may communicate with an external device, for example, including activating an LED, email, SMS or the like using various communication protocols for example including but not limited to wireless, wired, optical, cellular, RF, IR or the like communication protocols.

According to some embodiments, the drug is delivered to the target site using a delivery member for example including but not limited to a catheter, a permeable membrane, a selectively permeable membrane, a plurality of catheters, grafted tissue, blood vessel, or the like. A sensor or tissue treatment element may be incorporated into the delivery member.

The tissue treatment element may be used, according to some embodiments, to stimulate or inhibit tissue and the delivery site to control insulin uptake in the body to reduce the peak rise and fall of glucose levels, in order to prevent insulin starvation (prandial hyperglycemia) at the beginning of the peak and hypoglycemia at the end of the peak. The controller and tissue treatment element function together to regulate the blood glucose cycle. The tissue treatment element may use different methods and devices as described by the present application to stimulate or inhibit tissue leading to increased blood perfusion that improves insulin absorption or similarly to reduce insulin absorption when necessary.

Some embodiments of the present invention provide for a drug delivery device for the direct introduction of a drug to a target site having an implanted portion (internal) and a non implanted portion (external). Different components may be implanted for example including but not limited to a sensor, controller, delivery member, drug production while the user interface, tissue treatment element or drug storage compartment. In some embodiments, the tissue treatment element is not implanted but is external and applies the tissue treatment to the skin above the implanted drug delivery device. The external components may communicate with the internal components using protocols including but not limited to wireless, wired, cellular, optical, IR, RF communication or the like.

An implanted embodiment is capable of producing a drug for example including but not limited to insulin. Insulin production may be achieved by an active process, for example including but not limited to the activity of beta cells, genetically transformed cells, tissues, or the like live cultures or cells able to produce insulin, on demand. The trigger for producing and administrating the correct dose of insulin is the glucose level which may for example be sensed by the beta cells themselves. The tissue or skin treatments or stimulation methods can be used to treat or stimulate a tissue region to which insulin is infused by the insulin producing cells.

In some embodiments, the insulin producing cells may be covered or encapsulated to prevent the immune system from attacking the implanted cells. In some embodiments, the insulin producing cells may be disposed in an implanted closure or housing with additional components. In some embodiments, such as in case of implanted beta cells or other drug producing cells, the tissue treatment element may be used to control tissue conditions that could improve the production of the implanted cells. For example, by improving local perfusion the cell has increased availability of oxygen, glucose and other required building blocks. By improving the local perfusion also the beta cells or other glucose sensing element can react without unwanted delays to fast glucose variations, since the delay of the glucose transport for the blood system to the ISF compartment and to the sensor is reduced when local blood perfusion is increased.

The tissue treatment element, according to some embodiments, is used to stimulate tissue at the delivery site to improve insulin uptake in the body. In some embodiments, the tissue treatment controller and tissue treatment element function together to reduce the drug absorption delays and variations, through a feedback control that may involve the sensor utilized in the drug delivery system of the present invention. The tissue treatment element may use different methods and devices as described by the present applications to stimulate or inhibit tissue, which may lead to increased blood perfusion that improves insulin absorption or similarly to reduce insulin absorption when necessary.

Some embodiments of the present invention provide for an implantable drug delivery device for the automatic and direct introduction of a drug to a target site. The implanted drug delivery device includes tissue treatment element, as well as controller, delivery member, and an intrinsic drug production compartment. The implanted device may also include a sensor for the drug level. The implantable device further includes an external, non-implanted user interface that provides the user with an interface that controls the implanted delivery device. The user interface includes functions related to dosage form, dosage timing, and dosage trigger, which more are provided in relation to a database. The user interface may, for example, be provided in the form of a PDA, personal computer, mobile or cellular telephone or the like.

The controller, according to some embodiments, may initiate glucose production and dosage selection based on the sensed glucose levels. The user interface may allow a user to determine the timing of glucose production, dosage and delivery time. The controller and sensor function in a concerted manner to sense and control the level of drug delivery for example including but not limited to insulin. Such concerted functionality reduces any error to a minimum. the sensor used includes a continuous glucose monitor that provides continuous reading of the blood glucose levels. The controller may control the output of the tissue treatment element based on the sensed data, thereby creating a feedback loop that is able stabilize the insulin absorption into the blood system.

In some embodiments, the drug is delivered to the target site using a delivery member, for example including but not limited to one or more of a catheter, a permeable membrane, a selectively permeable membrane, a plurality of catheters, grafted tissue, blood vessel, or the like. The sensor or tissue treatment element may be incorporated into the delivery member.

In some embodiments, including also implanted drug delivery devices embodiments, of the present invention, the tissue treatment element is used to improve, modify and/or stabilizing the pharmacokinetic and/or pharmacodynamic profile of a drug delivered to the target site using a delivery member, for example including but not limited to a catheter, for a drug that is to be absorbed into the blood or lymphatic system. The devices described in some of the embodiments of the present application apply additional treatment or stimulation to the vicinity of the drug delivery site. The tissue treatment element may be implanted or placed externally to stimulate the required region.

In some of the embodiments of the present invention, including also implanted drug delivery devices embodiments, drug delivery may be undertaken with the use of at least one or more catheter, or a permeable membrane, or a selectively permeable membrane, or the like. At least one or more catheters may further encase a sensor, tissue treatment element, or other component of the drug delivery device of the present invention.

In some of the embodiments of the present application, including also implanted drug delivery devices embodiments, a sensor may be added for controlling the drug delivery. In any one of those embodiments, the sensor may be any state of the art sensor able to monitor and measure a measurand, for example including but not limited to glucose, cholesterol, hormone, protein, urea, carbohydrate, or the like. the sensor is used in conjunction with a controller to regulate a drug delivery protocol in response to the sense measurand levels. An embodiment of the present invention uses a continuous glucose monitor to control insulin levels in the tissue. Some embodiments of the present invention are obtained by automatically controlling the insulin infusion rate using a continuous glucose sensor and a control algorithm, effectively producing an artificial pancreas. This provides a closed loop control of glucose and insulin levels that are closely monitored and controlled to regulate the glucose level and reduce hyperglycemic or hypoglycemic events.

In any of the embodiments of the present invention, any implanted component may be made of biocompatible components. The material including the various components of the drug delivery device are inert and do not react with the implantation site.

In some of the embodiments of the present invention the implanted portion of the device is implanted subcutaneously. Implantation may be carried out in a minimally invasive surgical procedure such as keyhole surgery with local anesthesia. Implantation may be carried out via a subcutaneous injection of the drug delivery device.

In some of the embodiments of the present invention the user interface allows the user to operate and communicate with the implanted device. The user interface may be coupled to an external sensor. The user interface may have an integrated sensor for example including but not limited to a glucose monitor, cholesterol monitor, or the like.

Communication between the user interface and implanted device may be achieved with one or more of various communication protocols including but not limited to wireless, wired, cellular, optical, IR (infrared), RF (radiofrequency), acoustic or the like. The user interface may come in the form of a personal computer, PDA, cellular telephone or communicator, mobile telephone or communicator, or the like. The interface provides the user with one or more options to control the implanted drug delivery device with regard to tissue treatment element, dosage form, dosage timing, and dosage trigger or the like, by accessing a database, allowing the user to control drug delivery parameters.

Some embodiments of the present invention provide a drug delivery device that is able to better control the drug absorption cycle reducing to a minimum extreme situations. This is done, according to some embodiments, by way of better control of the drug delivery and/or by improving tissue absorption of a drug. Specifically, some embodiments enable the foregoing by applying a controllable treatment to the vicinity of the drug infusion site.

The introduction of a tissue treatment element into a drug delivery device has been discussed in various applications by the inventors of the instant application. However the method by which the tissue treatment is carried out may vary widely. Furthermore the type of tissue treatment employed may include at least one or more of nociceptive axon reflex, heat, cold, intermittent temperature change, ultrasound, optical, massage, physical stimulation, vibration, suction, IR, microwave, RF, optical, infusion of one or more additional substances, or the like. These treatments may be applied on the external skin surface, in internal tissue, or subcutaneous tissue in order to bring about an effect.

A tissue treatment protocol may be carried out at the target site or in its vicinity. One tissue treatment protocol may be heating to temperature of about 39.5° C. which is applied for short bursts for a period of 2-60 seconds every few minutes, evoking vasodilatation that improves the drug pharmacokinetics and/or pharmacodynamics in the drug infused tissue region. However, the specific treatment protocol parameters related to tissue type, threshold levels, burst timing, resting period, heat levels, heating power, time required for temperature rise and fall, and so forth, are variable and controllable. Some embodiments, whether as systems or methods of the present invention, provide for a system and/or method that are customized for an individual and feature a user specific treatment protocol.

Heat (and the heating process) may be applied to the vicinity of the drug infused tissue region. In some cases, such as for the infusion of some types of insulin and/or other proteins to the tissue heating to a temperature above some limiting level, such as for example 37° C., the heating is applied only to the vicinity of the drug infused tissue and not to the drug infused tissue region itself. This limitation of the heating area and/or volume prevents heating the drug above a limiting temperature that can denature or modify the drug itself. Heating the drug infused region vicinity induces a vasodilatation response also in the drug infused tissue region as was shown by W. Magerl et. al., Journal of Physiology, 497.3, pp 837-848 (1996), which discloses that heating the skin can induce vasodilatation in human at a distance of even 30 mm also due to activation of the nociceptive axon reflex. Heat may be applied according to many methods and devices described herein and/or in the applications incorporated herein by reference, including but not limited to one or more of direct heating through thermal energy, which can be generated electrically, such as using a resistor, or chemically, such as using exothermic reaction, and/or applying other forms of energy, including but not limited to ultrasound, optical radiation, electromagnetic radiation, microwave, RF (radio frequency) energy and so forth.

The human neural response to thermal stimulation includes several mechanisms such as the Nociceptive Axon Reflex that induce vasodilatation among other effects. The neural thermal response may vary widely between individuals. Therefore, in some embodiments, the system and method of the present invention feature a customized, calibrated, individualized tissue treatment that may be adjusted in one or more aspects to a specific individual to provide optimal drug delivery for an individual through the application of optimized tissue treatment.

The neural thermal stimulation protocol may be calibrated for individual patient to optimize the stimulation protocol according to their own nociceptive axon reflex activation threshold. For example, W. Margerl et. al. discloses that the vasodilatation evoking temperature after 64 seconds of heating can vary between 37-43° C. for different subjects, therefore individualized control of tissue heating may improve the efficiency, the accuracy and/or the repeatability of a drug delivery system with the required control of a tissue treatment element. Calibration can be achieved relative to a specific tissue targeted site. They also showed that in some cases short periods of heating can also evoke vasodilatation for a period of few minutes. Therefore it may be possible to control the pharmacokinetic and/or pharmacodynamic properties of a drug delivered to a tissue region, with the introduction of heat to evoke vasodilatation, eventually leading to improved drug uptake. However, heat can also be problematic as it may affect or even degrade the function of the drug itself. Thus heating for short time intervals with one to few minutes pause between them may induce less excessive heat to the tissue and prevent heating the infused drug itself, in cases heating the drug is unwanted effect, or can reduce the system power consumption.

A method for calibrating the treatment device is to initiate tissue stimulation gradually in the first instant of use of the treatment device and measure the treatment effect on the tissue, such as vasodilatation, using a specific sensor, including, for example (but not limited) a Laser Doppler Flowmetry (LDF) that is connected to the processor unit that controls the treatment device. The controller unit determines what level of tissue treatment to apply, to optimize the treatment effect without causing any adverse effects. For example, in the case where the tissue treatment employed is applying heat having the desired effect of increasing vasodilatation, the tissue treatment element may gradually heat the tissue until a predefined safety limit and measure the local tissue vasodilatation. The level of blood perfusion and vasodilatation can be measured by Laser Doppler Flowmetry (LDF) or by other sensors accepted or known in the art. Another option for measuring the blood perfusion is using an optical sensor for measuring tissue absorption and/or scattering, for example at the wavelength range of about 700 to about 1000 nm, which relates to the hemoglobin concentration at the probed tissue region. The processing unit may use the sensor information to determine the threshold temperature that evokes the neural response which induces the required vasodilatation level.

The calibration process may be carried out with an individual to determine the limits of the vasodilatation neural response and also the level of discomfort the individual is willing to endure. The process also determines the temperature threshold that is safe. For example, the various parameters, may include (but not limited to) burst timing, timing and length of resting period, heat levels, temperature, or current type. These parameters may be changed in order to personalize the treatment protocol relative to the user.

Another method for calibrating the treatment device may be to initiate application of tissue stimulation gradually. For example, the first time that the treatment device is used for an individual, tissue stimulation is applied gradually and then the treatment effect on the tissue is measured, by, for example, vasodilatation, using a specific sensor as described above until the required level of induced vasodilatation is achieved or the maximal safety temperature is reached. The processing unit uses this information regarding the baseline for the individually adjusted treatment level to determine the future tissue treatment levels for that specific patient.

In some embodiments, the controller may have access to various treatment protocols and historical data (which may be locally stored in a memory connected to the controller) relative to the different situation sensed by at least one or more sensor. The controller may also employ learning algorithms, including, for example (but not limited to), artificial intelligence methods to adjust or adapt the treatment protocols to be more specific or tailored to the drug delivery needs and of the user.

In some embodiments, the automated calibration process may be repeated periodically, for example every 6-12 hours, to compensate for changes that might have an influence on the temperature threshold of the neural thermal response, such as the axon reflex response of the individual. Any of the parameters, including but not limited to one or more of burst timing, timing and length of resting periods, heat levels, temperature or current type (for example) may be adjusted accordingly.

In some embodiments, the calibration process is repeated every time (or shortly before) the drug delivery or the tissue treatment element is operated. For example, the calibration process may be repeated during insulin bolus injection to ensure an appropriate induced vasodilatation response.

In some embodiments, event related calibration may be used to prevent or reduce the occurrence of gradually appearing variations in the neural response, such as axon reflex, due to variations of factors that influence the neural response, for example including but not limited to levels of nitric oxide and/or noradrenaline at the target tissue site.

In some embodiments, when tissue treatment, such as heating, is applied to the treatment area, a treatment parameter, for example temperature, may gradually be adjusted by the device's controller while measuring the desired tissue parameters such as vasodilatation, which may use Laser Doppler Flowmetry (LDF), to create a feedback calibration loop. Once vasodilatation reaches an intended value, the amount or rate of tissue treatment is stabilized to maintain that level of dilatation over a period of time.

In some embodiments, the calibration process is repeated also during the tissue treatment or stimulation. In this case, the treatment, such as heating, after initiation as previously described, is then regulated to maintain the desired tissue parameter(s), such as vasodilatation level, stabilized to a target level, more during the entire treatment. Stabilizing the desired tissue parameter, such as vasodilatation level, stabilizes also the absorption of drug in the blood and improves the consistency and reproducibility of the pharmacokinetics and pharmacodynamics. Controlling the tissue treatment level according to the desired tissue parameter(s), such as the vasodilatation level for example, may also reduce the power consumption of the treatment device according to some embodiments.

For example, in case of heating, since a short period of heating to a certain temperature above the threshold temperature initiates the axon reflex response and vasodilatation, there may not be a need to keep the temperature high for a long period, because of the lag effect of the axon reflex. Reduction of the temperature also reduces power consumption.

In some embodiments, calibration processes are repeated also during the treatment. In such a case, the treatment, such as drug administration, is started. The stimulatory effect is then calibrated with regard to the effect of drug administration, so that the level of drug (for example) may and be used to calibrate the desired amount of stimulation.

In some embodiments, the neural response that induces vasodilatation is stimulated by applying a mechanical force to the vicinity of the drug infused region, including but not limited to one or more of pressure, massage, vibration, suction and/or other known in the art mechanical stimulation. These tissue treatments or stimulation are known to stimulate the nociceptive axon reflex as well. Among the advantages of mechanical stimulation is that mechanical stimulation does not damage the drug, whereas for example heating above 37° C. might damage insulin. The calibration of the applied mechanical force may be performed by using one of the procedures described above.

In some embodiments, the neural response that induces vasodilatation may be additionally stimulated by infusion of one or more additional substances which may include any known peripheral vasodilator, such as tolazine, naftidrofuryl or suloctidil, to the vicinity of the drug infused region. In some embodiments, the additional substance infused into the vicinity of the measured tissue region modifies the drug pharmacokinetic and/or local blood perfusion with or without the creation of a chemical or other reaction between the drug and said one or more substances. This effect may be additive or synergistic to the above described forms of stimulation. For instance, nitroprusside, which induces vasodilatation, can improve blood perfusion in the drug infused tissue region. Another example is capsaicin that stimulates a neural response through the VR1 receptor and produces a similar response to thermal stimulation. The calibration of the level of the applied additional one or more substances may be performed by using one of the procedures described above. In some embodiments, the neural response that induces vasodilatation may be additionally stimulated by applying electrical current (which is known to increase tissue blood flow) to the vicinity of the drug infused region. The calibration of the level of the applied electrical current may be performed by using one of the procedures described above.

In some embodiments, the neural response that induces vasodilatation may be stimulated through a combination of the above suggested stimulation types. For example, by combining low temperature heat (for example below 37° C.) and mechanical stimulation, a better neural response may be achieved without damaging the drug molecule because of excessive heat. Another non-limiting example involves combining low temperature heat (for example below 37° C.) and infusion of an additional substance for obtaining a neural response without damaging the drug molecule because of excessive heat. Another non-limiting example involves combining application of a low level of thermal stimulation (for example below 37° C.) and application of electrical current to increase tissue blood perfusion more efficiently, without damaging the drug molecule because of excessive heat.

In some embodiments, the induced neural response, such as the nociceptive axon reflex, may also induce widening of the capillary pores and increasing the capillary wall permeability. This effect is also significant for improving the absorption of said drag through the capillary wall.

In any of the embodiments of the present invention, the tissue treatment element may be used to treat a tissue region to which insulin is infused during basal or bolus insulin delivery. One possible effect of the tissue treatment is improving the efficiency of absorption of the insulin into the blood and/or lymphatic systems, thereby reducing the amount of the insulin needed to create the desired metabolic effect. Without being limited by a single hypothesis, the undesired adverse effects of the excess insulin levels, such as excess weight gain, may be reduced.

Another effect of the tissue treatment according to some embodiments is improving and reducing the amounts and the duration that the insulin remains at the tissue infused region, since it is absorbed faster in the blood and/or lymphatic systems. Without being limited by a single hypothesis, the undesired local adverse effects of the excess insulin levels, such as the lipohypertrophy or local irritation may be reduced. Also, another possible benefit to using the tissue treatment element of the present invention is the induced increase in local blood perfusion, which reduces the local inflammation effects seen in current infusion sets. Another possible benefit to treating the tissue target area is the reduction of the short and long term local effects of insulin on the insulin infusion site, therefore the tissue treatment element may (and) lengthen the duration of using the same delivery site and may increase the longevity of the functionality of the infusion set.

In some the embodiments of the present invention, the stimulation protocol, may be determined by the controller, depending on the drug delivery mode used. For example, tissue stimulation methods may be activated for a drug delivery protocol of elective or preprogrammed boluses for brief periods to provide a boost to insulin absorption. In some embodiments, tissue and/or skin treatment methods may form a part of all or some of the elements of complex pre programmed boluses, including but not limited to split wave, square root and other bolus patterns. The stimulation may be activated for the initial phase of a standard bolus protocol, specifically for pre-programmed components of a split bolus or at intervals of interest of the square bolus. Stimulation may also be activated by a pre-programmed duty cycle independent of the bolus type. Moreover, the intermittent activation can be synchronized with individual bolus delivery components of the basal rate.

Unless otherwise defined, all technical and scientific terms used herein have the same meaning as commonly understood by one of ordinary skill in the art to which this invention belongs. The materials, methods, and examples provided herein are illustrative only and not intended to be limiting.

Although the foregoing has been described with respect to drug delivery of insulin for the treatment of diabetes, this is a non limiting example of the present invention. Any additional chronic or acute condition may be treated with the drug delivery device of the present invention, for example including but not limited to hypoxia, anemia, cholesterol, stroke, heart or the like.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "processing unit" or "computer" or "computer network", it should be noted that any device featuring a data processor and/or the ability to execute one or more instructions may be described as a computer, including but not limited to a PC (personal computer), a server, a minicomputer, a cellular telephone, a smart phone, a PDA (personal data assistant), a pager. Any two or more of such devices in communication with each other, and/or any computer in communication with any other computer, may include a "computer network".

BRIEF DESCRIPTION OF THE DRAWINGS

FIG. 3 illustrates an exemplary catheter for drug delivery combined with electric wires embedded into the catheter tube, according to some embodiments of the present invention.

FIG. 5 illustrates an exemplary connector between a catheter for drug delivery and the drug delivery pump, where the connector connects the tube for the drug delivery as well as electric wires, according to some embodiments of the present invention.

FIGS. 41A-D are schematic diagrams of an exemplary embodiment of the implanted drug delivery device, of FIGS. 40A-D, according to the present invention.

DETAILED DESCRIPTION OF THE INVENTION

Method and System for Drug Delivery

Figure 1:
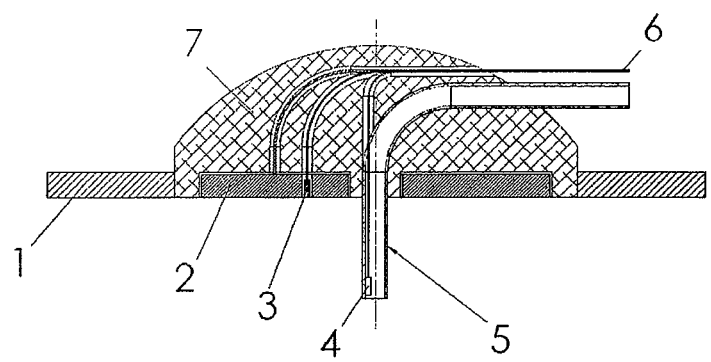
FIG. 1 illustrates an exemplary catheter for drug delivery combined with a heating element attached to the skin around the catheter, according to some embodiments of the present invention.

The present invention relates to devices for improving, modifying and/or stabilizing pharmacokinetic and/or pharmacodynamic profile of a drug infused into the tissue by a catheter and absorbed into the blood or lymphatic system. The devices described in some of the embodiments of the present application apply additional treatment or stimulation to the vicinity of the drug delivery site. The treatment can be one or combination of the following tissue treatment treatments modalities: heating, modifying temperature, massaging, mechanical vibration, acoustic vibration, ultrasound, suction, infusion of an additional substance or chemical, applying a low electric field, applying a low magnetic field, light irradiation, infrared ("RF") irradiation, microwave ("MW") irradiation, etc. In some embodiments, the device has a catheter for insertion within the tissue to infuse a substance into the infused tissue region. The infused tissue region (i.e., the infused region) can be one of the skin layers or the subcutaneous tissue or deeper tissue elements within any organ or viscera.

The catheter may also have a securing mechanical part that adheres to the skin and secures the catheter into its location and prevent it from being pulled out accidentally. The proximal end of the catheter may be connected to a drug delivery device which controls the infusion profile of the drug. In some embodiments, the drug delivery device also controls the additional treatment applied to the infused tissue region. In those embodiments, there is a communication channel between the drug delivery device and the treatment device. The communication can be either wired or wireless. Portions of the treatment device can be disposed inside the drug delivery device or outside of it. In some embodiments, the drug delivery device is a drug delivery pump, such as an insulin pump.

In some embodiments, the present invention is a device controlled by a pump that infuses a drug into a tissue region, which applies an additional treatment to the vicinity of the drug delivery site. In some embodiments, the pump's electronic processing unit operates based on a predetermined protocol or algorithm, any additional inputs and/or a drug-infusion profile of the applied treatment. In some embodiments, the pump's electronic processing unit communicates with the treatment device processing unit, which operates based on a predetermined protocol or algorithm and according to a drug infusion profile of the applied treatment. In some embodiments, the device regularly queries the pump's status using the pump's built-in communication capability. Based on the received data, the device operates in accordance with a predetermined protocol or algorithm of the applied treatment.

In some embodiments, the devices are neither controlled by the pump nor have any communications with the drug delivery pump. Instead, the devices detect the drug-delivery profile through the catheter and apply the treatment according to a predetermined protocol or algorithm. In such embodiments, the treatment device includes a sensor that can detect the drug infusion flow inside the catheter and deliver the information to the device processing unit, which operates based on a predetermined protocol or algorithm and on an infusion profile of the applied treatment. The drug flow can be detected by any conventional sensors, such as an optical sensor that detects the drug flow in a transparent catheter, a laser Doppler sensor, an ultrasonic Doppler sensor, a pressure sensor, a conductivity sensor, an inductance sensor that can measure changes in the flow rate of the infusion fluid under induced magnetic field. In some embodiments, the drug flow sensor detects not only the existence of a drug infusion flow, but also the infusion rate and uses that information in the treatment algorithm. In some embodiments, the drug infusion sensor detects the electromagnetic or acoustic emission of the drug delivery pump motor or electronics. In some embodiments, the device senses some additional parameters of the tissue and uses that information as well in the treatment algorithm.

In some embodiments, tissue treatment controls the temperature of the tissue region into which the drug is delivered. In some embodiments, temperature control can be to set a profile of temperature rise in a known rate, temperature stabilization at a known period and ending the profile by returning to the natural tissue temperature. This profile can be induced by a heater that heats the drug infused tissue region. Other temperature profiles for treatment or excitation of the drug infused tissue region are possible as well. For example, a cooling profile for decreasing blood perfusion or to induce a specific pharmacokinetic and/or pharmacodynamic profile for the drug or heating for short time intervals to further improve drug pharmacokinetics or pharmacodynamics. In some embodiments, the temperature profile can be applied to a larger region than the drug infused tissue region. Doing so may improve blood perfusion also in the vicinity of the drug infused tissue region and by way of a further increase drug absorption rate into the circulation by increasing the available absorption volume. In some embodiments, the temperature profile can be applied to a region smaller than the drug infused tissue region to save battery life.

A device for heating the tissue region into which the drug is delivered according to some embodiments of the present invention is illustrated in FIG. 1. In this embodiment, the infusion catheter is combined with a heating element attached to the skin around the catheter. The treatment device is a flat circular structure 7 with an opening in its center for the catheter tube 5 for entering the subcutaneous tissue. The other end of the catheter is connected to the drug delivery pump. In the illustrated embodiments, the treatment device includes a heating element 2, which may include a printed circuit board having the heating elements (e.g., resistors) provided thereon (as can be understood by one skilled in the art, other heating element types may be used). In some embodiments, the printed circuit board includes a temperature sensor 3. In some embodiments, a cooling element may be included in the case where more demanding temperature profiles are used.

The heating element can include a controller that controls the heating element (e.g., on/off or increased/decreased power) in order to stabilize the skin temperature to the required temperature according to the algorithm. In some embodiments, the temperature can be between 32-40° C. in order not to irritate the skin on the one hand and to have a sufficient effect on the tissue on the other hand. Temperature stabilization algorithms are well know in the art and can be executed by relatively simple controllers/processing units or ASICs. Skin or tissue damage depends on the applied temperature and the heat exposure time, so for a short period of few minutes even higher temperatures up to range of 42° C. can be used.

In some cases lower heating temperatures may be required. For instance, Novolog (aspart) insulin can be exposed to maximal limiting temperature of 37° C. (FDA document NDA 20-986/S-024, "NovoLog Insulin aspart (rDNA) Injection", Jul. 26, 2004). In such an embodiment, the skin temperature can be slightly higher as long as the immediate vicinity of the insulin infusion site is below 37° C. For this case, there is advantage in the heating configuration by the present invention and shown in FIG. 1, since the device warms the tissue and not the insulin, so minimal temperature modification is affecting the injected insulin per se while maximal heat stimulation is applied to the tissue, in order to increase local blood perfusion. Also as shown in FIG. 1, the heating element 2 is not in contact with insulin infusion catheter 5. For this reason, the present invention suggests also thermal isolation 7 between insulin catheter 5 and heating element 2, such that the insulin is not overheated and minimally exposed to high temperatures.

In some embodiments, an additional or alternate temperature sensor 4 is located inside the catheter tube 5. This temperature sensor allows better control of the temperature of the drug infused tissue region. Specifically, first, the insulin limiting temperature inside the tissue can be avoided even though higher temperatures can be used at the skin to get optimal stimulation of the blood perfusion in the region. Also, by regulating the temperature inside the drug infused region to a fixed optimal temperature, a better stabilization of the drug chemical processes, pharmacokinetics, absorption into the blood system and/or pharmacodynamics can be achieved. The local temperature variations in the drug infused region induced by ambient temperature variations as well as other factors induce variations in the blood absorption rate of the drug and induces larger variability of the drug pharmacokinetics and pharmacodynamics. As mentioned before, in the case of insulin delivery, it is important to reduce the variability of the temporal profile of the insulin absorption into the blood and tighter local temperature control can be advantageous improve the glucose level regulation of diabetic patients.

In some embodiments, the heating element 2 and one or two of the temperature sensors 3 and 4 are connected to the drug delivery pump through cable 6. In this embodiment, the drug delivery pump may include the power source and the controller of the treatment process.

In some embodiments, element 7 covering heating element 2 is thermally isolating. Specifically, element 7 reduces the heat dissipation to the environment in case of heating the tissue. As mentioned earlier, element 7 can also thermally isolate the drug in catheter 5 from being exposed to the increased temperature of the heater(s). In case of cooling of the drug infused tissue region, element 7 reduces heat transfer from the environment to the cooled tissue region. It can also ease the thermal stabilization of the infused tissue region, in case of changing environments and ambient temperatures.

In some embodiments, the heating device as shown in FIG. 1 is attached to the tissue with an adhesive layer (tape) 1. The adhesive layer can also cover the heating element. In some embodiments, the adhesive layer may be a thermal conducting adhesive or a thin adhesive layer. The adhesive layer may be provided covered with a laminate (not shown in FIG. 1) that is peeled off by the user before insertion of the catheter and attachment of the heating device. Typically, for catheter insertion, the device is supplied with a sterile needle inside the catheter (not shown in the figure) that is pulled out after insertion of the catheter to the required tissue region.

In some embodiments, the heating device shown in FIG. 1 includes an adhesive thermally conducting layer in contact with the skin, an electrically isolating layer with temperature sensors, a heating layer, a thermally isolating layer and an adhesive layer for attaching heating device 2 to additional thermal isolation 7 if needed. All layers can be manufactured using printing techniques and mass production methods.

Figure 2:
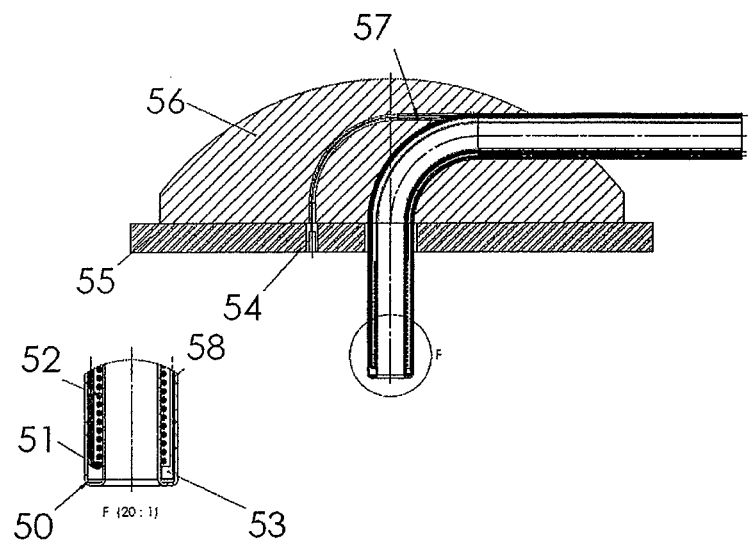
FIG. 2 illustrates an exemplary catheter for drug delivery combined with a heating element embedded into the catheter tube, according to some embodiments of the present invention.

Another device for heating the tissue region into which the drug is delivered is illustrated in FIG. 2. In this embodiment, the infusion catheter contains a heating element 52 in a distal part 50, which is close to the infused tissue region. The heating element can be made of a conductive wire with high enough resistance and good strength and durability. For instance, tungsten wires or deposition of thin copper strip are commonly used for this purpose. Heating element 52 may be embedded into the catheter tube during the manufacturing of the tube, using methods known in the art. For example, this can be done by wrapping the wire coil on a thin wall tube and then covering it with a second polymeric layer. The other side of the heating wire coil 51 is directed up in the tube as well. In some embodiments, the heating wire can be shaped in other forms such as a single loop or zigzag or whatever can be efficiently manufactured to provide the required heat for the infused tissue region. An advantage of heating inside the tissue is a smaller volume of tissue around the drug infused region is heated and hence requires less electric power. Also, the heated volume, usually in the subcutaneous tissue, is better isolated from the skin temperature which may vary with the ambient temperature. However, in this case, the catheter temperature can be limited to a temperature that will not alter the properties of the infused drug in case of drugs that are more sensitive to temperature increase then insulin. In the external heating configuration shown in FIG. 1, the spatial temperature distribution may be such that the skin temperature and tissue regions around but not close to the catheter tip are at higher temperature without causing any damage to temperature sensitive drugs. In the external heating configuration, the drug exposure to the higher temperatures may be more limited, although the high temperature still affects a portion of the drug infused tissue region or the tissue regions around the drug infused tissue regions.

In some embodiments, temperature sensor 53 is located inside the catheter tube as well. This sensor monitors the infused tissue region temperature. This temperature sensor allows better control of the temperature of the infused tissue region. By better stabilization of the drug chemical breakdown and dissolution processes or pharmacokinetics or absorption kinetics into the blood system an improved and more reproducible pharmacodynamic profile can be achieved. In this device, the controller can be either in the treatment device or in the drug delivery pump and controls the heating current to stabilize the infused tissue region temperature to the required temperatures and durations according to the algorithm.

In some embodiments, device element 56 that supports the catheter attachment to the body is thermally isolating to further reduce the power requirements of the heating element and by thus, battery weight. The heating device as shown in FIG. 2, is attached to the tissue with adhesive layer 55. The adhesive layer can come covered with a laminate (not shown in FIG. 2) that is peeled off by the user before insertion of the catheter and attachment of the heating device. In some embodiments, another temperature sensor 54 may be in contact with the skin to improve the temperature stabilization algorithm. In some embodiments, only skin temperature is used in conjunction with the catheter heating element. In some embodiments, heating elements provided internally and externally of the tissue may be used.

The other side of the catheter is connected to the drug delivery pump. In some embodiments, in this configuration as well as in other configurations detailed in the subject disclosure, all wires that connect the treatment device and the drug delivery pump may be embedded in the catheter tube connected to pump as shown in the tube cross section at FIG. 3. In some embodiments, the wires are attached to the outer side of the tube as shown in the cross-section illustrated in FIG. 4. Embedding or attaching the wires to the tube enables the device to be more comfortable for the user (e.g., to be worn and handled).

Figure 4C:
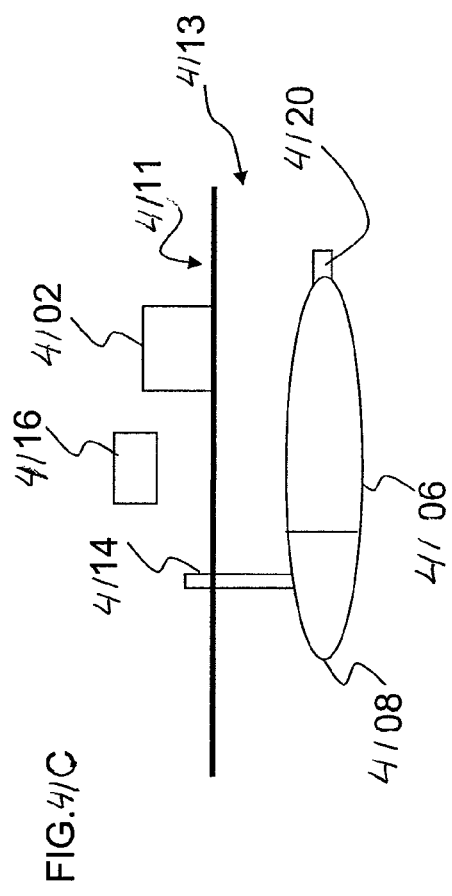
FIG. 4 illustrates an exemplary catheter for drug delivery combined with electric wires attached to the catheter tube, according to some embodiments of the present invention.
Figure 4D:
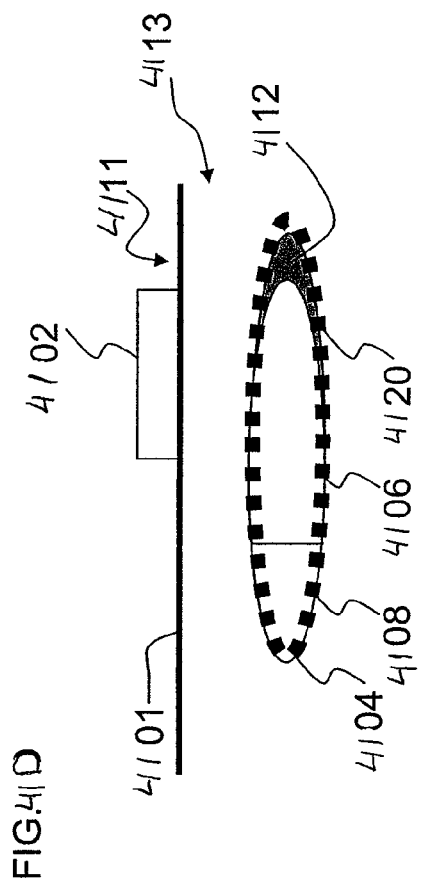

The wires shown in FIGS. 3 and 4 are preferable connected to the drug delivery pump. In some embodiments, two connectors may be used for connection of the disposable catheter and treatment device to the drug delivery pump. The first connector connects the catheter tube to the pump as currently established, for instance, in many current commercial insulin pumps. A second connector may be used to connect the wires used by the treatment device for communication between the pump unit and the treatment device unit or power supply or connecting sensors used for sensing of tissue parameters and/or infusion parameters to the pump unit. The wire connector can be one of the known connectors for connecting electrical wires. In case of using two separate connectors for the electrical wires and the infusion tube, the wires can also be separated from the tube.

In some embodiments, as shown in FIG. 5, the tube connector 102 and the electrical wires connectors 103-106 can be combined into a single housing 101. The single connector housing option is more comfortable for the user to handle, i.e., to assemble and disassemble the catheter and the treatment device from the pump unit. The connector housing can also include a known prior art clip or locking mechanism that enables disconnection of the connector only when the locking mechanism is pressed or opened. Such locking mechanism can reduce also the chance of leakage of the infusion fluid from the connector.

In FIG. 5, four wires are used for controlling the treatment device by the pump unit and for connecting a sensor that measures the treatment level or effect in order to stabilize the treatment effect to the required level. In other cases of treatments, sensors and device configurations, a different number of wires may be connected through the connector.

In some embodiments, a similar connector can also be used on the treatment device's side. These embodiments may be more comfortable for the user in case of an infusion catheter and a drug delivery pump used for longer periods such as 2-3 days. For some time periods, the drug delivery pump can be detached from the user's body leaving a minimal weight and length of tubing in contact with the user's body. These embodiments can be useful and more comfortable for taking a shower. In such a case, the tubing and wires can include either a connector on both ends, a connector on the treatment device end only or a connector on the drug delivery pump device end only. In case of having a connector on the treatment device side, another alternative includes having a disposable tube connecting the treatment device and the drug delivery pump, where a reusable electrical cable is attached to the drug delivery pump and includes a connector for connecting to the treatment device. In some embodiments, the tube and wires may be disposable as with the catheter or its securing device, for instance, as the tube and catheter of common insulin infusion sets are designed.

Figure 6:
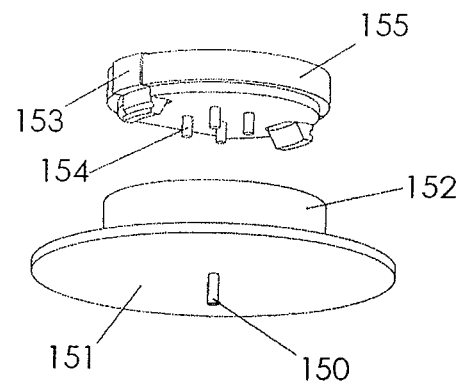
FIG. 6 illustrates an exemplary device for treatment of a tissue region combined with an infusion catheter made of disposable part and reusable part, according to some embodiments of the present invention.

In some embodiments, the treatment device can be made of two parts, one being disposable and one being reusable, as shown in FIG. 6. The disposable part includes the catheter 150 that is inserted into the tissue and the insertion mechanism (not shown in the figure). In some embodiments, the treatment device can also include the skin attachment part 151 and an adaptor mechanism 152 to connect the two parts. In some embodiments, the treatment device can include all or a portion of the treatment element such as the heating element (in the case of heat treatment or other elements for other tissue treatments or excitation methods of the present invention). In some embodiments, the treatment device may include one or more sensors.

The reusable part 155 may include all or a portion of the treatment element. It may include a processing unit, one or more sensors and a power source. The power source can be a rechargeable battery. As shown in FIG. 6, two parts are attached with a mechanical locking mechanism 153 and four pins 154 for electrical connections. In case of rechargeable battery, the user may have two alternating reusable units 155 whereas one is attached to the treatment device and one stays charging. When the battery in the treatment device is empty, damaged or the user is instructed (based on a specific battery schedule), the user switches between the two reusable units. The charger unit has the same mechanical and electrical connection as the disposable part 152 that easily fits the reusable unit 155.

In some embodiments, the reusable part communicates via a communication channel with the drug delivery pump, using wired, wireless, wireline or any other connection. In some embodiments, the treatment device has no communication with the drug delivery pump. For example, only the catheter tube, which is not shown in the FIG. 6, can be connected to the drug delivery pump.

Consequently, in the case of an insulin pump, this device can be used with many of the continuous subcutaneous insulin infusion pumps presently on the market and for those in development, for similar purposes. The treatment device identifies by itself the infusion of an insulin bolus and starts the treatment protocol accordingly. The beginning of insulin infusion can be identified as described earlier by a sensor in the treatment device such as an optical sensor on the transparent tube, a laser Doppler sensor, an ultrasonic Doppler sensor, a pressure sensor connected to the tube, or a conductivity sensor in the tube, under applied magnetic field, or a temperature sensor of the infusion fluid in the tube. Alternatively, the treatment device can identify the pump motor electromagnetic emission or acoustic emission to detect the bolus period. The sensors that require contact with the infusion fluid, such as the conductivity sensor, are located in the disposable part 152. The other sensors may be either in the disposable part or in the reusable part with a respective known in the art mechanical structure that allow them to measure the required infusion fluid parameter or parameters.

In some embodiments, a separate unit which is attached to the insulin pump detects the delivery of an insulin bolus and transmits the information to the treatment unit to start treatment, either with wired or wireless communication. The separate unit may sense the electromagnetic or acoustic emission of the pump motor or read the pump buttons when pressed or read the pump display or pump other indicators or have an additional button disposed on the pump for manual operation of the tissue treatment device. In some embodiments, the reusable unit may have at least one user input (e.g., a button) for the user to use (e.g., press) when the user desires the treatment to start.

In some embodiments, the reusable part or the disposable part is connected with an electrical cable to a third unit that may include the power source, the control unit or other electronic parts of the device. In some embodiments, a single part disposable treatment device is electrically connected to the third unit.

Figure 7:
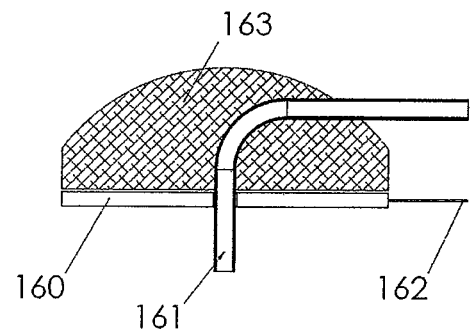
FIG. 7 illustrates an exemplary device for treatment of a tissue region combined with an infusion catheter made of disposable part and reusable part, according to some embodiments of the present invention.

An alternate embodiment of the present invention is illustrated in FIG. 7, where the reusable part is shaped as a thin disk 160 inserted between the disposable part 163 and the skin. Thin disk 160 can be a heater with a temperature sensor used to aid in stabilizing the temperature of the skin around the catheter insertion area. In some embodiments, the temperature sensor can be part of a thermostat that automatically regulates the heating temperature by connecting and disconnecting the heater element power lines, or other self regulating heaters, such as PTC thermistors, and or increasing or decreasing the power supplied to the heater.

In some embodiments, the thin heater can be manufactured by printing technologies. In some embodiments, the thin heater can be of thickness of 0.1-0.5 mm. In some embodiments, a thicker heater with thickness of 0.5-2 mm may be used. Also, a thin disk can be more flexible and more comfortable for the user. Before insertion into the tissue, the reusable disk 160 can be adhered or attached to the disposable part 163 such that the treatment element of the reusable device is adhered to the skin above the drug infused tissue region. In some embodiments, a special mechanical jig is used for attaching reusable disk 160 to disposable part 163. In some embodiments, an inserter, such as inserters used for insulin infusion sets, is used for entering both units to the tissue. The thin heater disk 160 and the catheter securing element 163 can be disposable. In some embodiments, thin heater disk 160 can fit several conventional catheter securing elements, including insulin conventional infusion sets.

The reusable treatment disk is connected to the drug delivery pump or to a third unit using a cable 162. The reusable treatment disk can perform many treatments or stimulations discussed in the present application, such as heating, massaging, vibrating, acoustic excitation, optical radiation, RF radiation, MW radiation, applying electrical field etc. In some embodiments, disposable part 163 can be wider than reusable part 160 such that the rims of the disposable part are used for attaching or securing the treatment device to the skin.

Figure 8:
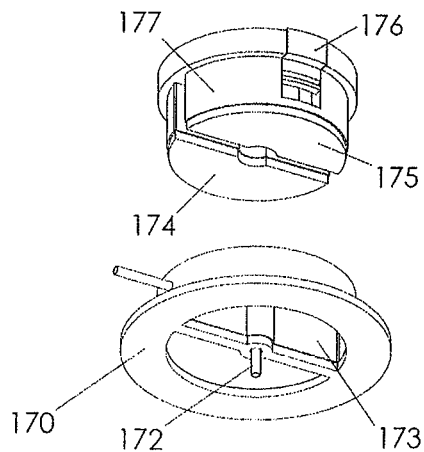
FIG. 8 illustrates an exemplary device for treatment of a tissue region combined with an infusion catheter made of disposable part and reusable part, according to some embodiments of the present invention.

FIG. 8 illustrates an alternate embodiment in which the disposable part 173 includes only the catheter tube 172, the insertion mechanism and the skin adhering element 170. Before insertion of the catheter into the tissue, the disposable part 173 can be attached to the reusable part 177 such that treatment elements 174 and 175 of the reusable part gets in contact with the skin when the treatment device is attached to the user's skin. In some embodiments, the disposable part 173 can be attached to the reusable part 177 with a locking mechanism 176. The reusable part 177 can be wired or wirelessly connected to the drug delivery pump or a third unit. Alternatively, it may not be connected to the drug delivery pump and thus, may include a power source, as described above. The reusable treatment part can perform treatments discussed above.

Figure 9:
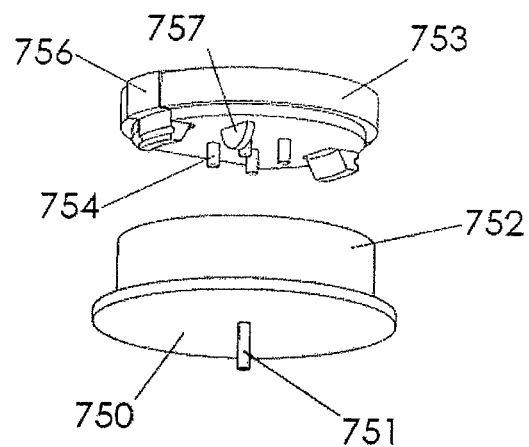
FIG. 9 illustrates an exemplary device for treatment of a tissue region combined with an infusion catheter made of disposable part and reusable part, according to some embodiments of the present invention.

FIG. 9 illustrates another embodiment in which the disposable part 752 includes the catheter tube 751, the insertion mechanism, the skin adhering element 750 the drug container and passive parts of the drug pump. In this embodiment, the reusable part includes a processing unit, a pump motor and may include some of the sensors, as described in shown in FIG. 6. The power source can be either in the reusable part or the disposable part. In case of using a rechargeable battery, the battery can be located in the reusable part, as discussed in FIG. 6. In some embodiments, the disposable battery is located in the disposable unit. Prior to insertion of the catheter into the tissue, the disposable part 752 may be attached to the reusable part 753 such that schematic electrical connection pins 754 fit the disposable part electrical connection pins and such that mechanical pump operating mechanism 757 in the reusable part fits the passive parts of the drug pump in the disposable unit. The pump mechanism can be one of the many known in the art pumping mechanisms. For instance, in case of a peristaltic pump, the mechanical pump operating mechanism 757 in the reusable part can be part of the pressure wheel of the peristaltic pump that presses a tube in the disposable part.

Alternately, a mechanical pump operating mechanism 757 in the reusable part can be a cog-wheel that rotates a matching pump cog wheel in the disposable part or moves a linear slider, such that the disposable unit includes only low cost parts. In some embodiments, some of the more expensive parts of the drug delivery pump can be included in the reusable unit. In some embodiments, the disposable part 752 is attached to the reusable part 753 with a locking mechanism 756. The reusable part 753 can be wirelessly or wired connected to the drug delivery pump or to a third unit or not connected and contain the power source as described before. The reusable treatment part can perform treatments discussed above.

Figure 10:
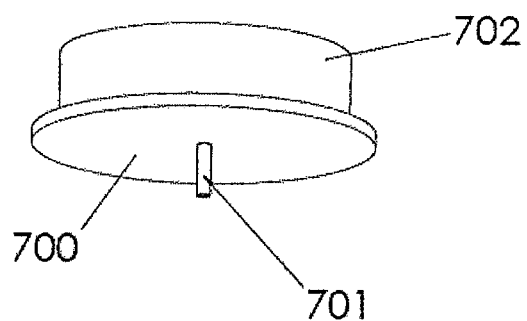
FIG. 10 illustrates an exemplary device for treatment of a tissue region combined with an infusion catheter and drug delivery pump, according to some embodiments of the present invention.

FIG. 10 illustrates an embodiment of the present invention, in which there is a single disposable unit 702 including the drug delivery pump, the treatment device, the catheter tube 701, the insertion mechanism, the skin adhering element 700 and the power source. The single unit pump and treatment device can perform the above described treatments. In some embodiments, in case of a single unit with a heat treatment that can be accomplished either by direct heating or by indirect heating such as a byproduct of radiation, the drug reservoir is thermally insulated from the heating element or from the heated regions. This is useful in the case of the insulin delivery because of insulin's sensitivity to high temperatures. In some embodiments, the drug reservoir has in also a temperature sensor to verify that the drug temperature is not exceeding the limiting temperature. The same thermal insulation of the drug reservoir can be used in embodiments described above with reference to FIGS. 6-9.

The devices schematically shown in FIGS. 6-10 are examples of different combinations of disposable and reusable units that provide insulin delivery with treatment or excitation of the drug infused tissue region. As can be understood by one skilled in the art, other embodiments ranging from fully disposable units to fully reusable units (except the catheter that normally will be disposable) are also possible whereas each of the device components can be provided in the disposable or reusable units according to its way of implementation and its production cost.

In some embodiments, the third unit can be attached externally to the drug delivery device to improve user's comfort. In such a case, electrical wires can be attached to the catheter tube at a large portion of the catheter length and be separated only near the drug delivery device such that the drug catheter is connected to the drug delivery device and the wires are connected to the third unit. The third unit can include also power source and controller. When the drug delivery starts (e.g., drug bolus delivery), the third unit can detect operation of the drug-delivery device either actively by direct communication between the two units or by passively sensing some signals induced by drug delivery device when operated as described before, such as using the electromagnetic emission of the drug delivery device. In some embodiments, the third unit can be disposed in a bag, a pouch, a case, or a belt adaptor containing the drug delivery pump such as devices used for carrying insulin pumps. In such a case, the tube is connected to the insulin pump, while the wires are connected to the carrying device. The carrying device can also include a switch for manual start of the treatment or indicators for indicating that the treatment is applied or indicators that the battery power is adequate, too low or indicators that a problem occurred with the treatment, such as wire disconnection, etc. The switch or indicators, or a portion thereof, can be disposed also on the reusable unit or disposable unit or on the drug delivery pump.

In some embodiments, the devices by the present invention can have short range RF or IR communication with a data management and control unit, such as a Personal Digital Assistant ("PDA") computer, to a personal cellular phone or to an application specific data managing device that supports managing drug therapy. In case of insulin delivery, a data managing device can obtain glucose readings either from a glucose sensor manually, through data communication or by reading glucose sensing strips. The data managing device can get the information about previously consumed carbohydrates and other food or drinks. The data managing device can also retain patient history and relevant parameters, such as weight, BMI, insulin resistance etc.

The data managing device can also calculate the optimal required amount of insulin and the optimal tissue treatment or excitation profile. This information can be sent wirelessly to the drug delivery pump and to the treatment device, for optimal drug delivery. The treatment device may transmit tissue parameters measured by sensors disposed thereon to the data management unit (which may also be or include the control unit; "data management and control unit") as additional information for the therapy calculation or history for future statistics and data analysis. In some embodiments, the data management and control unit may only recommend to the user an optimal drug dosage, an optimal treatment and/or an excitation profile to be applied to the infused tissue region and the patient can approve the treatment before it starts. In some embodiments, the data management and control unit may recommend the user an optimal drug dosage only and the patient may approve the dosage before it starts and decide on best treatment or excitation to be applied to the infused tissue region. In some embodiments, the data management and control unit can be part of the drug delivery pump. In some embodiments, the data management and control unit can include a switch for manual start of the treatment, indicators for indicating that the treatment is applied, indicators that the battery power is adequate, too low or indicators for determining if a problem occurred with the treatment, such as wire disconnection, etc.

Figure 11:
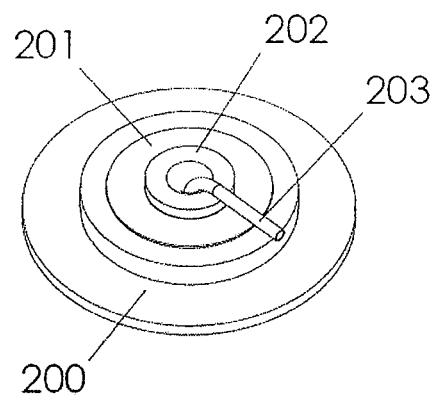
FIG. 11 illustrates an exemplary catheter for drug delivery combined with a mechanical vibrating element attached to the skin around the catheter, according to some embodiments of the present invention.
Figure 12:
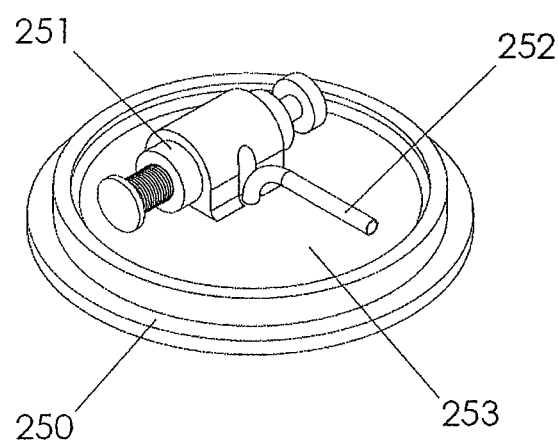
FIG. 12 illustrates an exemplary catheter for drug delivery combined with a mechanical vibrating element attached to the skin around the catheter, according to some embodiments of the present invention.

In some embodiments, tissue treatment or stimulation can include (either alone or in combination with other stimulation) vibrating the tissue region into which the drug is delivered. Two examples of such treatments devices are shown in FIGS. 11-12. The vibrating treatment device with open cover, shown in FIG. 11, includes an electric motor 202 that rotates a disk 201 with asymmetric load. Rotating this disk causes the treatment device to vibrate in a circular vibration mode. By adhering the treatment device to the skin with an adhesive layer, the treatment device vibrates the tissue underneath the treatment device and the catheter tip. This vibration can have a frequency of about 1-50 Hz, which is commonly used for massaging tissue, an typically includes 60-300 rpm. As can be understood by one skilled in the art, other frequencies, or rotational velocities can be used as well. In some embodiments, the motor axis can be horizontal with the rotating disk vertical to the skin surface. In this case, the vibrations are vertical to the skin surface in addition to horizontal.

The vibrating treatment device with open cover, as shown in FIG. 12, includes an electromagnet 251 that pulls a ferromagnetic rod with two weights at either end thereof. A spring returns the rod to his initial location after the electromagnet is turned off. Thus, by applying a periodical signal to the electromagnet, the rod with its weights will vibrate at the periodic signal frequency and induce vibrations to the tissue underneath. To improve vibration efficiency, the rod, weights mass and the spring force can be designed to have a mechanical resonance frequency at the required frequency for massaging the infused tissue.

When the resonance frequency is applied to the electromagnet a larger amplitude vibrations is induced. By adhering the treatment device to the skin with an adhesive layer, the treatment device vibrates the tissue underneath the treatment device and the catheter tip. In some embodiments, the vibration axis can be designed to vibrate to other directions, such as vertical or perpendicular to the skin surface. In some embodiments, the vibration device can vibrate mainly the catheter tip either horizontally or vertically using vibration mechanisms that induce excitation of the tissue near the catheter tip.

Figure 13:
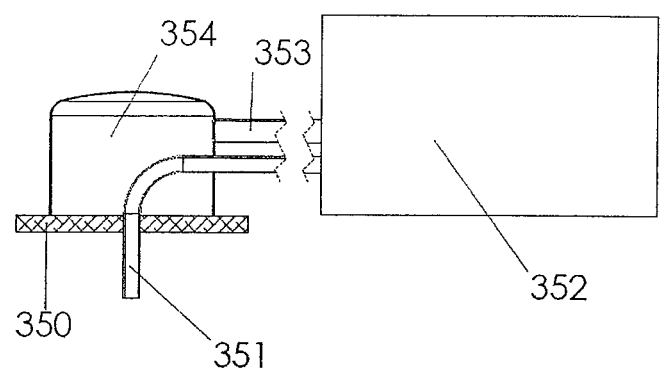
FIG. 13 illustrates an exemplary catheter for drug delivery combined with a massaging element that massages the skin around the catheter, using air cushion controlled by the drug delivery pump, according to some embodiments of the present invention.

An alternate embodiment of tissue massaging is illustrated in FIG. 13. This embodiment can massage with lower frequency and larger amplitude as compared to the vibrating embodiments. The treatment device (which in this embodiment may be disposable) includes a catheter tip 351 for inserting into tissue (as before), located in the middle of a chamber 354 with rigid wall all around except of the skin side, which also includes a flexible membrane 350. The flexible membrane is adhered to the skin as before with an adhesive layer, as part of the catheter insertion process described before, to secure the catheter in its position. Chamber 354 may be connected with additional tube 353 to the drug delivery pump 352. The tissue massaging is established by pumping air in and out of chamber 354 through tube 353 via an additional pump in the drug delivery pump unit, according to a treatment or massaging protocol. In this case, the control of the treatment protocol is accomplished by the drug delivery pump unit and the disposable unit can be relatively simple and low cost. When the air is pumped out of chamber 354, flexible membrane 350 curves into the chamber pulling the tissue adhered to it. When the air is pumped into the chamber, the flexible membrane curves out and pushes the tissue. This process is done periodically according to a typical frequency of about 0.01-10 Hz. Other frequencies are possible as well. In some embodiments, the chamber is filled with an incompressible fluid, such as water, and appropriate pump cause the fluid to flow in and out.

In an alternate embodiment, the flexible membrane can include a rigid surface which includes a plurality of openings and a flexible membrane covering the openings to improve adhesion to the skin, and to spatially modulate the skin massage. In yet another alternate embodiment, the flexible membrane outer surface can have small features (bumps) extending out of the surface to improve massaging effect to the tissue. In some embodiments, tube 353 can be connected to a third unit that controls and applies the massage treatment as described before.

Figure 14:
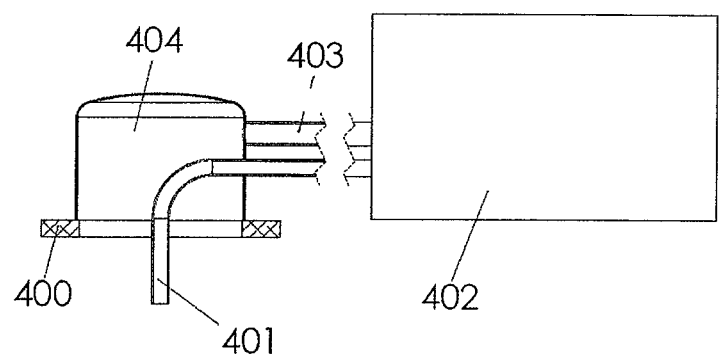
FIG. 14 illustrates an exemplary catheter for drug delivery combined with a suction element that affects the skin around the catheter, according to some embodiments of the present invention.

Another embodiment of a treatment device is a suction device that provides suction of the tissue around the infusion catheter, as shown in FIG. 14. Suction of a tissue region is known to improve blood perfusion in that tissue region. The treatment device (which is disposable) includes a catheter tip 401 for insertion into the tissue (as before), located in the middle of a chamber 404 with rigid wall all around except of the skin side, where an opening is included. The chamber walls are adhered to the skin with a circular adhesive layer 400 that seals the chamber rim to the skin. The adhesive layer is attached to the skin during the catheter-insertion process to secure the catheter in its position. Chamber 404 is connected with an additional tube 403 to the drug delivery pump 402. The skin suction is accomplished by pumping the air out of chamber 404 through tube 403 via an additional pump provided in the drug delivery pump unit. In this case, the control of the treatment protocol is accomplished by the drug delivery pump unit and the disposable unit can be made simple and low cost. The suction is done according to a predetermined treatment protocol, for example—a suction of 1 minute in duration can be applied after an insulin bolus injection to improve insulin absorption into the blood system. Another example is applying vacuum in chamber 404 for 30 seconds and then releasing the vacuum for additional 30 seconds. This process can be repeated several times in order to increase blood perfusion in the tissue region underneath the treatment device. In some embodiments, the chamber opening to the tissue can be made of a rigid surface with few openings to increase adhesion area to the skin and to spatially modulate the skin suction. In some embodiments, tube 403 can be connected to a third unit that controls and applies the suction treatment as described before.

In some embodiments, in order to modify the delivered-drug's pharmacokinetic and/or pharmacodynamic profile, a small modulation of the infusion process through the infusion catheter is induced. In other words, the infusion fluid is slightly pulled in and out of the tissue during or after the drug infusion process. This action induces an increased flow of interstitial fluid ("ISF") around the catheter tip because of the variable induced pressure fields. The increased ISF flow increases the drug diffusion distance and reduces the time constant of the drug absorption into the blood system. The flow modulation can be done by the drug delivery pump by reversing the pump direction for short periods and small amount of pumped fluids. Also, the drug delivery pump can keep moving the infusion fluid in the catheter slightly in and out after the end of drug bolus infusion.

Figure 15:
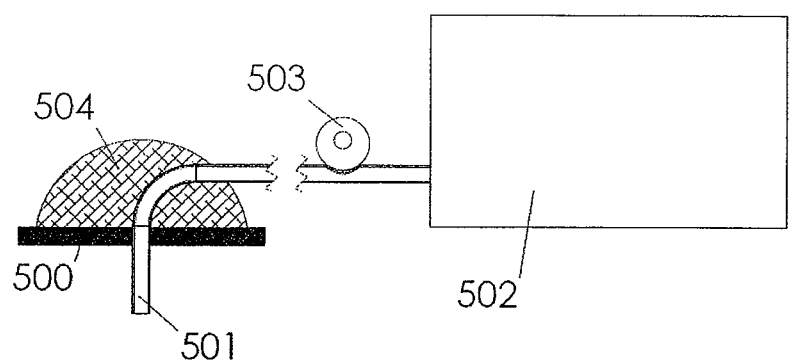
FIG. 15 illustrates an exemplary catheter for drug delivery with additional pumping element that move the infusion fluid in and out of the catheter, according to some embodiments of the present invention.
Figure 16:
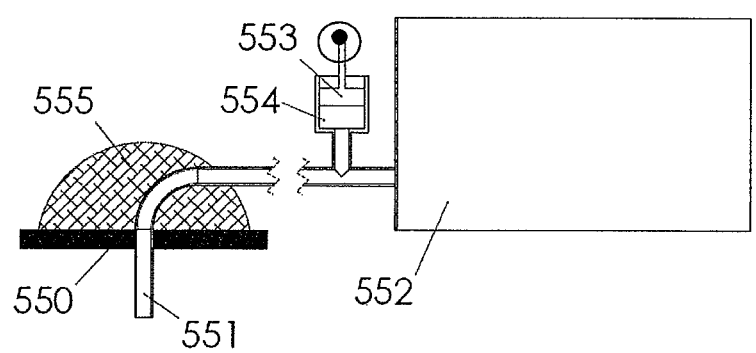
FIG. 16 illustrates an exemplary catheter for drug delivery with additional pumping element that move the infusion fluid in and out of the catheter, according to some embodiments of the present invention.

FIGS. 15-16 illustrate two exemplary embodiments of methods to implement the above tissue treatment as an additive component to existing drug delivery pumps, without reversing the drug delivery pump direction. These embodiments include modulating the flow of the infusion fluid in the infusion catheter tube by two different modalities. In FIG. 15, a wheel 503 is provided having its rotating axis off the wheel center. Thus, when the axis is rotating, one side of the wheel applies pressure to the proximal side of catheter tube 501 and pushes the infusion fluid forward. The other side of the wheel 503 releases the catheter tube 501 and retracts the infusion fluid a slightly backwards. In FIG. 16, the fluid modulation is done by a piston 553 connected to the catheter tube 551 and moves up and down to induce in and out flow to the infusion fluid in the catheter tube 551. In some embodiments, a proper air removal procedure and means should be used when the catheter is connected to the drug delivery pump 552 and before insertion ( ). In both embodiments, the modulation mechanism can be attached to the drug delivery pump, provided therein, in the disposable part or in a third unit connected to the infusion tube.

Figure 17:
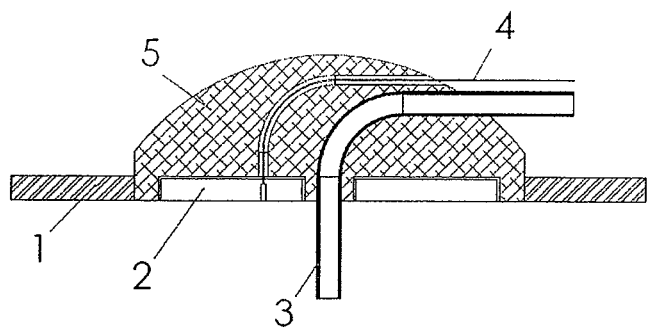
FIG. 17 illustrates an exemplary catheter for drug delivery with an acoustic excitation of the skin close to the catheter, according to some embodiments of the present invention.

In some embodiments, the tissue treatment device can include an acoustic excitation element to stimulate the vicinity of the tissue region into which the drug is delivered, as illustrated in FIG. 17. In these embodiments, the infusion catheter is combined with the acoustic excitation element 2 attached to the skin around the catheter. The treatment device may include a flat circular structure 5 with a center opening for the catheter tube 3 that enters the subcutaneous tissue. The other side of the catheter may be connected to the drug delivery pump. The acoustic excitation element can be made of piezoelectric materials such as PZT or PVDF. The acoustic excitation can include low or high acoustical frequencies or higher frequencies in the ultrasonic region.

The acoustic excitation device is attached to the tissue with an adhesive layer. The adhesive layer can be either on the outer ring area 1 or cover also the acoustic excitation element with an acoustic conducting adhesive, such as adhesive hydrogels. The acoustic excitation element can also be covered with an acoustic conducting layer such as acoustic hydrogel or liquid. The adhesive layer may be provided covered with a laminate (not shown in FIG. 17) that can be peeled off by the user before insertion of the catheter and attachment of the acoustic excitation device. Usually, for the catheter insertion, the device is supplied with a sterile needle inside the catheter (not shown in FIG. 17) that is pulled out after insertion of the catheter. The acoustic excitation element can be either connected to the drug delivery pump using cable 4 or to a third unit or to an electronics disposed as part of the acoustic excitation treatment device, as described earlier.

Figure 18:
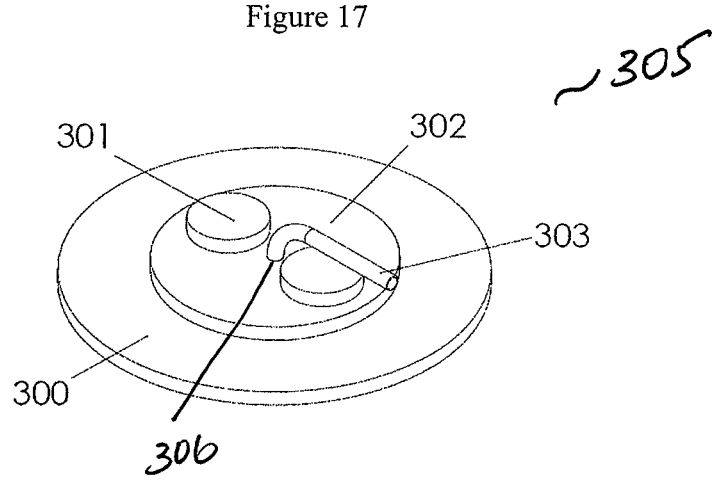
FIG. 18 illustrates an exemplary catheter for drug delivery combined with an optical radiation source irradiating the skin close to the catheter, according to some embodiments of the present invention.

In some embodiments, the tissue treatment device can use optical radiation to stimulate the tissue region, as illustrated in FIG. 18. In these embodiments, the infusion catheter is combined with an optical radiation element 301 attached to the skin around the catheter. The treatment device may be a flat circular structure 302 with a central opening for the catheter tube 303 that enters the subcutaneous tissue. The other end of the catheter 303 is connected to the drug delivery pump. The optical radiation element can be made of known in the art light sources, such as LEDs, laser diodes, lamps, etc. The optical radiation can be in the visible or NIR or MIR regions. The light source may emit pulsed light or CW light and the pulsed light source may further emit pulses that are appropriate to generate photoacoustic or thermoacoustic signals on the catheter and/or in the tissue region close to the catheter. The optical radiation device is attached to the tissue with adhesive layer.

The adhesive layer can be provided on the outer ring area 301 or cover the optical radiation element with an optically transparent in the relevant optical wavelengths adhesive. The adhesive layer is covered with a laminate (not shown in FIG. 18) that is peeled off by the user before insertion of the catheter and attachment of the optical radiation device. Usually, for catheter insertion, the device is supplied with a sterile needle inside the catheter (not shown in the figure) that is pulled out after insertion of the catheter. In some embodiments, the light source can be disposed in the drug delivery device and delivered with an optical fiber or several fibers to the optical radiation treatment device. The optical radiation source can be either connected to the drug delivery pump using a cable, connected to a third unit or to an electronics disposed as part of the optical radiation treatment device, as described earlier.

Figure 19:
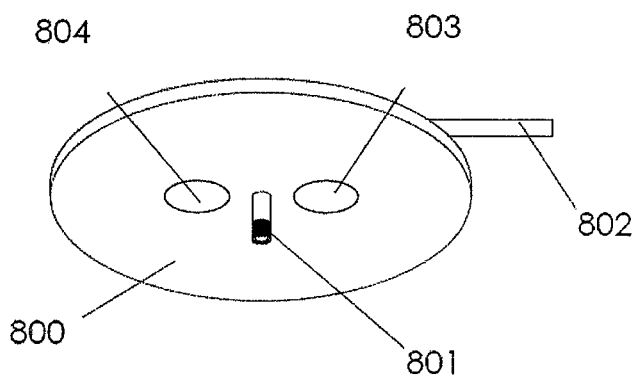
FIG. 19 illustrates an exemplary catheter for drug delivery combined with an optical radiation source irradiating the skin close to the catheter, according to some embodiments of the present invention.

In an alternate embodiment, optical radiation tissue excitation device, as illustrated in FIG. 19, coats the catheter tip with an optical absorption coating 801 that absorbs the wavelength or some of the wavelengths of the optical radiation. The treatment device can be similar to the optical radiation treatment device described before. In this embodiment, the treatment device can be a flat circular structure 800 with a central opening for catheter tube 801 to enter the subcutaneous tissue. The other end of the catheter 802 is connected to the drug delivery pump. The treatment device may also includes optical irradiation elements schematically shown by 803 and 804. The optical irradiation elements can be made of known in the art light sources, such as LEDs, laser diodes, lamps, etc. The light source may emit pulsed light or CW light and the pulsed light source may further emit pulses that are appropriate to generate photoacoustic or thermoacoustic signals on the catheter tip 801.

The optical irradiation wavelength can be either in the visible region or in the NIR. In some embodiments, using wavelengths range of 700-1000 nm provides relatively low absorption of the optical radiation in the tissue. Consequently, a larger portion of the illuminated radiation can be scattered in the tissue and absorbed in the catheter tip. The tip-absorbed optical radiation can induce a local hit around the catheter tip and efficiently heats the infused tissue region, as discussed above in FIG. 2. Using shorter wavelengths in the visible region, but also in the 700-1000 nm region, can increase the portion of the radiation absorbed by the hemoglobin and consequently can heat more blood or hemoglobin reach regions in the irradiated tissue region. Using longer wavelengths in the NIR, MIR or FIR regions can increase the portion of the radiation absorbed by the water in the tissue and consequently can heat more of the water to reach regions in the irradiated tissue region. Also, in case of using light pulses to create photoacoustic excitation, the portion of excitation induced at the catheter tip, hemoglobin regions or water regions, such excitation can be according to the absorbed radiation distribution and the photoacoustic coefficient of each region. The produced photoacoustic signal can be measured using an acoustic sensor disposed skin attachment structure 800 and can be used for monitoring the energy absorbed in each of those regions or catheter tip 801.

In some embodiments, some of the wavelengths of the above mentioned regions can be used for better control of the heated or stimulated region of interest. In some embodiments, at least one of the wavelengths is absorbed by a catheter tip coating and at least one wavelength is not absorbed by the coating to better control of the heated or stimulated region. The algorithm to control tissue excitation can obtain information from tissue temperature sensors (disclosed above), acoustic sensor, optical sensor, the drug delivery profile and additional drug or tissue parameters. The algorithm can control wavelengths to regulate the drug absorption into the blood system.

In some embodiments, a device similar to the one illustrated in FIGS. 2 and 18 can irradiate the drug infused tissue region, externally or internally, respectively, with radio frequency (RF) radiation or microwave (MW) radiation. Another embodiment can apply an electric field to the drug infused tissue region using, for instance, 2 electrodes similar to items 301 shown in FIG. 18, to apply the field to the skin or using electrodes disposed on the external side of the catheter tip inserted into the tissue. Also, the same device can be used to apply high or low frequency fields and even DC field. To improve the electrical contact the adhesive layer can be a conducting hydrogel or other known in the art materials to attach electrodes.

In some embodiments, an additional substance can be infused into the vicinity of the drug infused region, such that the additional substance modifies the drug pharmacokinetic and/or pharmacodynamic profile with or without the creation of a chemical or other reaction between the two substances. Specifically, the additional drug may influence either or both of the drug infused tissue region or improving the drug's pharmacokinetics and/or pharmacodynamics profiles. This effect is not necessarily due to a chemical reaction between the drug and the additional substance. In some embodiments, the additional substance improves local blood's perfusion in the vicinity of the drug infused region and accordingly, reduces the absorption time constant of the drug into the blood system. This effect may be additive or synergistic to the above described forms of stimulation. For instance, nitroprusside, which induces vasodilatation, can improve blood's perfusion in the drug infused tissue and improve the drug absorption into the blood system.

Figure 20:
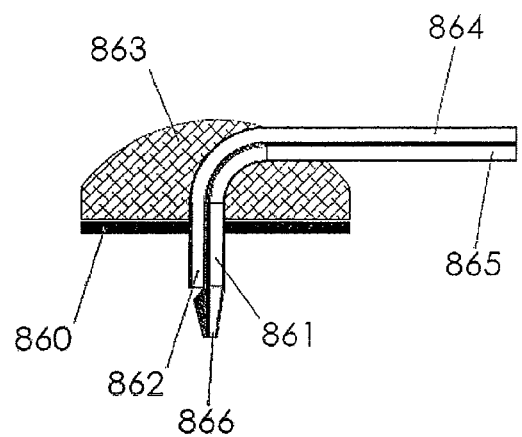
FIG. 20 illustrates an exemplary double lumen catheter for drug delivery, according to some embodiments of the present invention.

The additional substance can be infused into the drug infused region either through the same catheter or through an additional catheter, which can be attached or separated from the drug infusing catheter. In some embodiments, the catheter can be a double-lumen catheter with 2 openings inside the same tissue region or at two separate tissue regions, as shown in FIG. 20. Openings 866 and 862 of the two lumens 865 and 864, respectively, can be at different depths in the tissue. In the illustrated embodiment, the double lumen catheter is secured to the skin with a circular element 863 and an adhesive layer 860. In some embodiments, the catheter can include an additional treatment element, as discussed above, such that the combination of the additional substance and the treatment provides the desired tissue stimulation or treatment. In an embodiment of a single-lumen catheter, the additional substance can be either mixed with the drug and delivered, pumped, infused, or injected together into the catheter tube. Alternatively, the additional drug can come from a different container with a separate pump or drug delivery device and mixed in the catheter tube according to the flow rates of the drug and the additional substance using an infusion algorithm of the two substances. In some embodiments, the two containers can be either disposed in the same housing, attached to each other or separated. Similarly, in case of double lumen tube, one lumen may be connected to the drug delivery device and the second lumen may be connected to the additional substance delivery device. In some embodiments, a combination of the above treatment methods and/or devices can be placed into a single device to improve its operation and efficacy.

In some embodiments, the catheter can be drawn at a 90° penetration angle. As can be understood, other angles are possible. Smaller angles can improve attachment of the catheter, but insertion at such angles may be more irritating to the patient.

In some embodiments, a sensor can be added to the treatment device configuration. Alternatively, it can be added to general infusion sets, such as insulin infusion sets, and can be used to aid in detecting if the catheter securing element is lifted or starting to peel off the skin. The sensor can be provided in the catheter securing element so that it is in direct contact with the skin, indirect contact through the adhesive layer or other layers attached to the skin. The sensor can measure pressure or skin conductivity, impedance, and/or back-reflected optical or acoustic signal from the skin. A change of the contact level between the sensor and the skin will induce an electronic signal to either the treatment device or drug delivery device. Then, the device can either inform the user to fix the attachment of the securing element to the skin or to reinsert the catheter into the tissue in case it is detached or to pause or stop the drug delivery or the treatment till the catheter positioning is fixed.

In some embodiments, the treatment device can be secured to the patient using a strap or a belt that holds the treatment device into its position. The strap can be placed around any part of the patient's body, depending on the location of the drug infused region and the patient's comfort. Using such a strap can reduce the chances of the catheter to be pulled out in more demanding situations, such as jogging. For example, the strap can be placed around the abdomen, leg, thigh, arm etc.

In some embodiments, the strap can have a compartment, a pocket or an adaptor for holding the drug delivery device. In embodiments using a third unit that supports the treatment device, the third unit can be attached to the strap or even be embedded into the strap. The third unit can be embedded into the strap or belt, and may be connected to the catheter disposable unit by electrical wires using a connector at the wire end. In some embodiments, the drug delivery pump can be attached to the strap and connected to the catheter disposable unit with a tube for drug delivery. In some embodiments, the disposable unit can be attached to the strap to further reduce chances of the catheter being pulled in more demanding situations.

The power source can be a thin battery, such as the batteries manufactured by Power Paper Ltd. The electronics can be implemented on a flexible printed circuit known in the art to provide the required flexibility for the patient's comfort.

Figure 21:
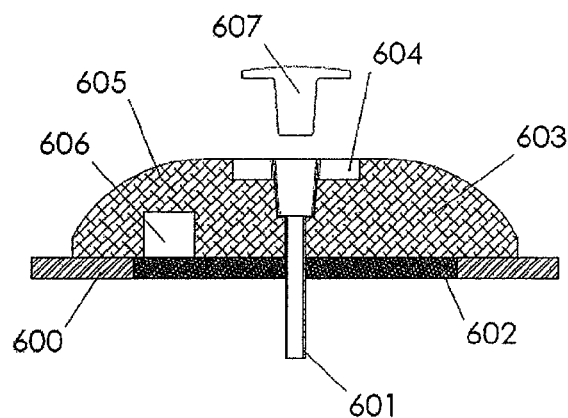
FIG. 21 illustrates an exemplary catheter for drug delivery combined with a port for syringe insertion, according to some embodiments of the present invention.

As can be understood by one skilled in the art, the above methods and devices for exciting the tissue are not limited to drug-delivery pumps and can be used with manual delivery of a drug, such as connecting a syringe (instead of a pump) to the proximal part of the catheter. In these embodiments, the catheter proximal part can end in a connector or a port that fits the syringe tip. Accordingly, the distal part of the catheter is inserted into the tissue as before. In some embodiments, the proximal part of the catheter tube is short, such as it is embedded into the treatment device, as shown in FIG. 21. In this case, treatment hardware, which includes treatment element 602, processor 606, power source and the abovementioned elements for tissue treatment or excitation, are disposed in the disposable catheter unit 603, which includes the adhesive layer 600 for skin attachment and the catheter distal tip 601. The syringe device can be either a regular syringe, an automatic syringe or other automated subcutaneous drug delivery devices that can provide a known volume of drug and can be connected to the catheter port for the drug delivery.

In some embodiments, the catheter unit with syringe port can be divided into disposable part and reusable part. In some embodiments, the syringe port comes with a plug 607 that covers the syringe port when not in use. In this case, there is no drug delivery unit in the system, the treatment device can detect infusion of the drug and start the treatment accordingly. The drug infusion can be detected using the above mentioned methods, such as flow detection, pressure detection, conductivity detection or temperature detection. In some embodiments, a mechanical pressure sensor 604, shown in FIG. 20, can detect the insertion of the syringe into the port automatically, manually via a switch on the treatment device or wirelessly by a remote control. The injection detection sensor can be also an optical or RF vicinity sensor that detects a unique RF transmission from the syringe unit or a unique optical pattern or signal. The injection sensor can also get some information from the injection device by either RF communication or optical reader such as barcode reader. The information can include the drug type and dose. In some embodiments, the treatment device includes a processing unit 606 that can get that information and fit the treatment algorithm accordingly, as described before. The same treatment device with syringe port can be used for several injections according to each treatment profile and duration, battery capacity and other parameters.

Figure 22:
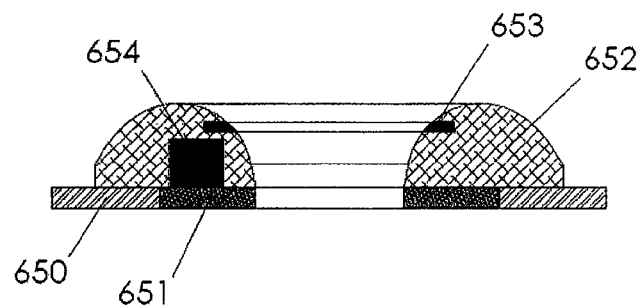
FIG. 22 illustrates an exemplary device for excitation of the skin and a tissue region underneath to which a drug is injected, according to some embodiments of the present invention.

In some embodiments, tissue or skin treatments or stimulation methods can be used to treat or excite a tissue region to which a drug is injected. In this case, as shown in FIG. 22, the excitation device 652 is attached to the skin and has a circular opening for direct drug delivery with a syringe and a needle. This option can fit injection devices without a needle, such as jet injectors or tissue perforation technologies or alternatively micro-needles injection devices. Also, the injection syringe can have many forms for drug injection in addition to the standard syringe, such as automatic syringes etc. An advantage of the device is that it is attached to the tissue prior to the drug injection. The device stimulates the injected tissue region after the drug delivery process in order to improve the drug absorption into the blood system. The excitation profile and duration is accomplished according to an algorithm that fits the drug and possibly the patient, as described earlier.

The detection of the injection can be done automatically by injection sensor 653, manually via a switch on the treatment device, or wirelessly by a remote control. The injection detection sensor can be an optical sensor or an RF vicinity sensor. The injection sensor can receive information from the injection device by either RF communication or optical reader such as barcode reader. The information can include the drug type and dose. In some embodiments, the treatment device includes a controller or processing unit 654 that can get that information and fit the treatment algorithm accordingly. The treatment element 651, as shown in FIG. 22, is placed around the injection area and the adhesive part 650, which attaches the device to the skin around it. In some embodiments, other shapes are possible, such as many of the shapes described before.

The same treatment device can be used for several injections according to each treatment profile and duration battery capacity and other parameters. Before injection, the skin in the device opening can be cleaned with cleaning fluid or pad such as alcohol pad through the device opening to prevent infections. In some embodiments, treatment device can have a U-shape to facilitate skin cleaning or other shapes.

In some embodiments for drug injection, tissue or skin treatments device is attached to the skin after drug injection. In some embodiments said tissue or skin treatment device is single use with a single use energy source. In some embodiments said tissue or skin treatment device is reusable use a rechargeable power source. In some embodiments said tissue or skin treatment device is combined of disposable and reusable elements. In some embodiments said tissue or skin treatment device is activated and starts tissue treatment automatically when applied to the skin.

Figure 23:
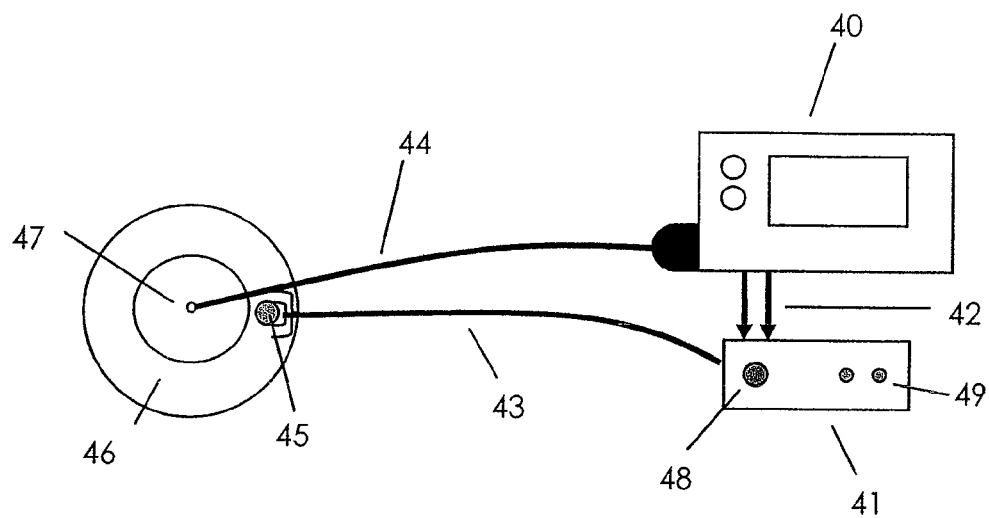
FIG. 23 illustrates an exemplary device for improving insulin pharmacodynamics, according to some embodiments of the present invention.

The following example demonstrates a device that improves the functionality of existing pump-based insulin-delivery systems. Such system, shown in FIG. 23, includes an insulin pump 40 and an infusion-set 44 which delivers the pumped insulin into the tissue. The infusion set includes a tube 44 and a catheter 47, which is inserted into the subcutaneous tissue. The device has two components: i) a flat heater 46, which is attached to skin around the insertion point of the catheter, and ii) a controller unit 41, which is disposed into the casing of the insulin pump unit. The controller unit has a switch/button 48 for manual operation and two indicators 49 for "treatment is on" and for battery status. The two components are connected by wires 43.

The controller monitors the activity of the insulin pump using an electronic sensing element and it also controls the activity of the heating element. The controller monitors the electromagnetic emission from the pump. During a bolus mode, the pump emits a well defined series of electromagnetic pulses at constant rate, shown as arrows 42. For example during a bolus dose, the paradigm 722 insulin pump from Minimed emits specific pattern of electromagnetic pulses for each 0.1 unit of injected insulin at a rate of 0.1 unit per second. Counting those electromagnetic pulses enables one to determine the amount of injected insulin in the bolus initiate the operation of the heating element and adjust its parameters, such as the duration and heating temperature, accordingly. The temperature of the heater is controlled by the controller using a temperature sensor 45 located on the heating element. In this example the temperature of the heating element did not exceed 39° C. to avoid damage to the infused insulin.

In some embodiments, the heating device can be operated manually. In this case, the controller controls the activity of the treatment element. Once a user injects a bolus of insulin using the insulin pump, the user also activates a switch/button 48 located on the controller to initiate the heating-element operation for a predetermined duration. The temperature of the heater is controlled by the controller using a temperature sensor located within the treatment element (heating element). In this example the temperature of the heating element does not exceed 39° C. to avoid damage to the infused insulin.

The flat heating element used in this example has several layers. The upper layer is a polyethylene layer which seals the element. Below that layer, there is an etched circuit, below which there is a copper layer for heat distribution and mechanical support. Below that layer, there is another sealing polyethylene layer, below which there is an adhesive tape from 3M® which is bio-compatible. The heater has a thickness of less than 0.2 mm and his diameter is 3 cm. Thin electric wires of length of 60 cm with small connectors at both ends connected the heater to the controller unit. The power used for the heating can be 2 Watts. The heating was turned on and off by the controller to stabilize the skin temperature at 39° C. The heat duration was set to 30 minutes, after which the temperature regulation was stopped.

In general, the attachment and operation of the insulin delivery system with the heater is very similar to the operation of the insulin delivery system without the heater. The described device includes a case into which the insulin pump is inserted. The case contains also an electronic circuit and batteries to operate the controller and heater. Accordingly, the patient first connects the infusion set tube to the insulin pump. Then, the patient connects the electric wires connector to the electric connector on the heater. The patient then attaches the heater to the center of the catheter securing element using the adhesive tape of the catheter securing element. The insulin catheter is then inserted to the subcutaneous tissue either manually or using the catheter spring inserter. The mechanism of the catheter insertion is the same as usual using the same insertion module and following the same steps. The heater can be attached to the catheter securing element before insertion. The patient can connect the infusion set tube to the catheter. The patient connects the wires coming from the heater to a designated connector on the controller. The operation of the bolus is either automatic or manual as described before.

Figure 24:
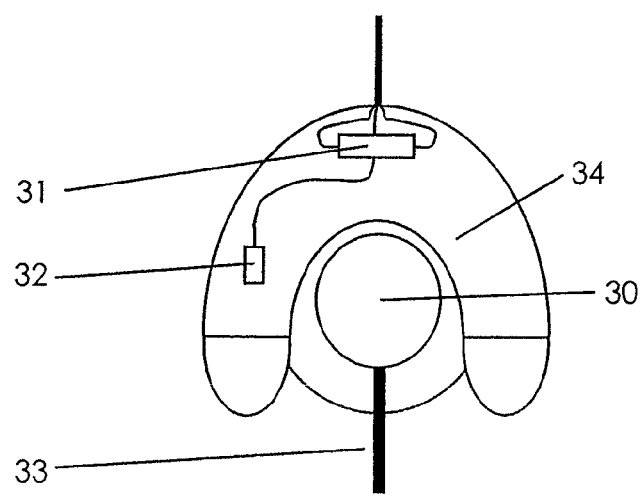
FIG. 24 illustrates an infusion catheter for insulin delivery with U shaped heater, according to some embodiments of the present invention

Another heater structure is shown in FIG. 24. In this case, the heater 34 is U shaped and attached to the skin around the insulin infusion set 30. The advantages of this configuration are that the heater can be an independent unit that fits many of the commercial infusion sets and also the thermal insulation between the insulin and the heater is kept. The U shaped heater can be thin or thicker and be built in many ways known in the art. The U shaped heater shown in FIG. 24 is made of heat conducting metal and has a resistor 31 for heating and a temperature sensor 32 for controlling the temperature.

Figure 25:
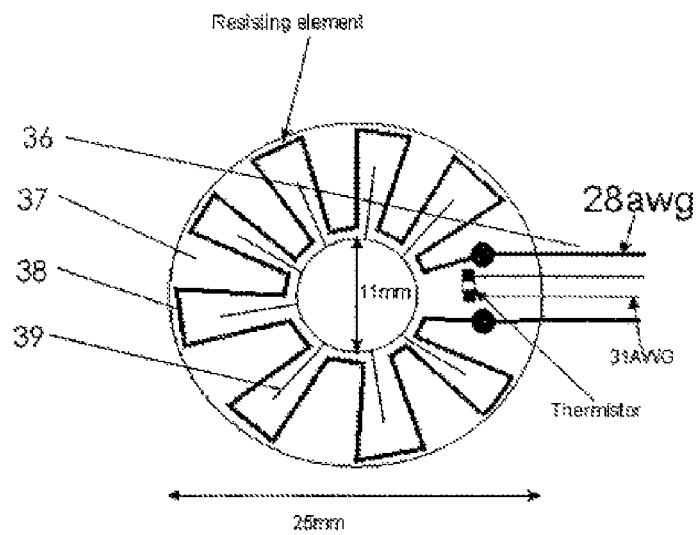
FIG. 25 illustrates an infusion catheter for insulin delivery with circular thin heater, according to some embodiments of the present invention

Another heater structure is shown in FIG. 25. In this case, the heater 37 is circular and attached to the insulin infusion set around the catheter prior to insertion into the body, as described above. The shape of the cuts 39 enable attachment of the heater to the infusion set prior to removing the catheter cover, although the catheter cover diameter may be larger then the central opening. It is important to remove the catheter cover or cup as the last operation before insertion of the catheter to the tissue because of safety and sterility issues. However, having the cuts 39 of the heater enable using a heater with an optimized central opening diameter without the limitations of the catheter cover. This is important in order to optimally heat the drug infused tissue vicinity on one hand and keep the thermal insulation between the insulin in the catheter and the heater on the other hand. The heater can be an independent unit that fits many of the commercial infusion sets. The heater includes also a temperature sensor for controlling the temperature. The thickness of this heater may be about 0.2 mm.

To demonstrate the improvement of the insulin pharmacodynamics of the device described in this example, a euglycemic glucose clamp study was performed, using the following protocol. An insulin dependent diabetic volunteer treated with an insulin pump arrived after an overnight fast prior to taking a morning bolus with the pump. The subject lied down in supine position. The subject's blood glucose level was stabilized at 100 mg/dl. A bolus of insulin was given using the subject's insulin pump (0.15 U/kg). The pump was halted from the end of the bolus administration. A 20% dextrose drip was adjusted to keep the blood glucose level at about 100 mg/dl. Frequent blood sampling (every 5-10 min) was used for adjusting Glucose Infusion Rate (GIR) as required for tight control of the euglycemic glucose level.

Figure 26A:
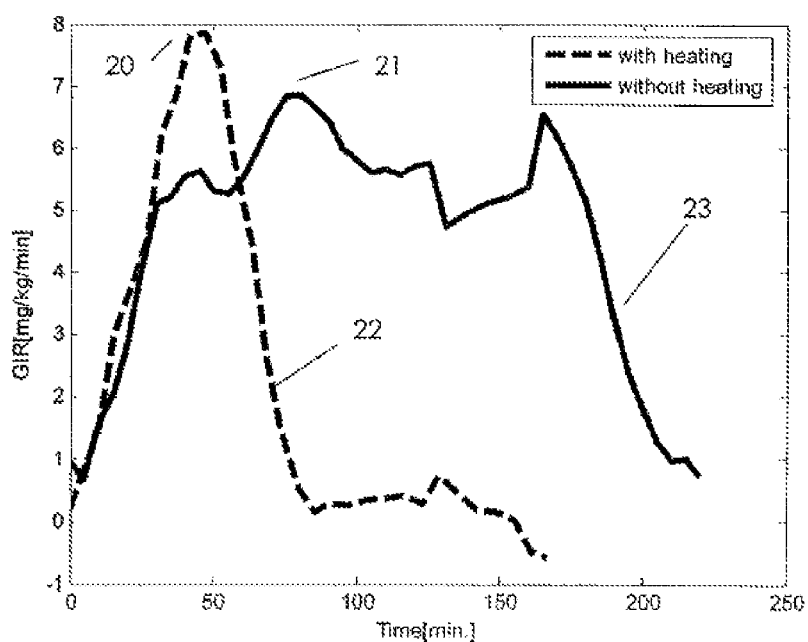
FIG. 26*a* illustrates an example of a graph of the insulin effect with and without treatment, according to some embodiments of the present invention.

The above described procedure was performed in the same subjects under the same conditions with and without using the heating device. A typical result is shown in FIG. 26*a*. The two graphs show the GIR in glucose milligrams per minutes per subject's kg vs. time. The solid line shows the GIR without the heating treatment, while the dashed line shows the GIR on the same subject with heating. It can seen that the time to peak action was significantly shorten from 75 min without heating 21 to 50 min with heating 20. Also the GIR decrease, which is an indication for insulin clearance out of the circulation and cessation of it's systemic effects was much faster with heating 22 then without heating 23. Both of those parameters are important for better control of the glucose level since the delay of the peak action may cause glucose rise immediately following meals and the residual insulin level in the tissue and in the blood may induces late hypoglycemia and promote an error in the estimation of the effect of the next insulin bolus. Those two parameters (the delay to insulin peak action and the residual insulin level), which are important for tight glucose level regulation are very important also when automatically controlling the subcutaneous insulin infusion rate using a continuous glucose sensor and a control algorithm. There are many attempts to compose such an "artificial pancreas" since the development of continuous glucose monitors. In this case, any delay such as the current delays of the insulin absorption and action time, any variability in this delay and any variability in the residual insulin level in the body induces an error for the control algorithm that will result in less tight glucose regulation. Thus, another use of the methods and devices by the present invention is to combine them with a glucose sensor, insulin delivery device and a control algorithm to provide a better accuracy and robustness of a closed loop glucose level control system.

Figure 26B:
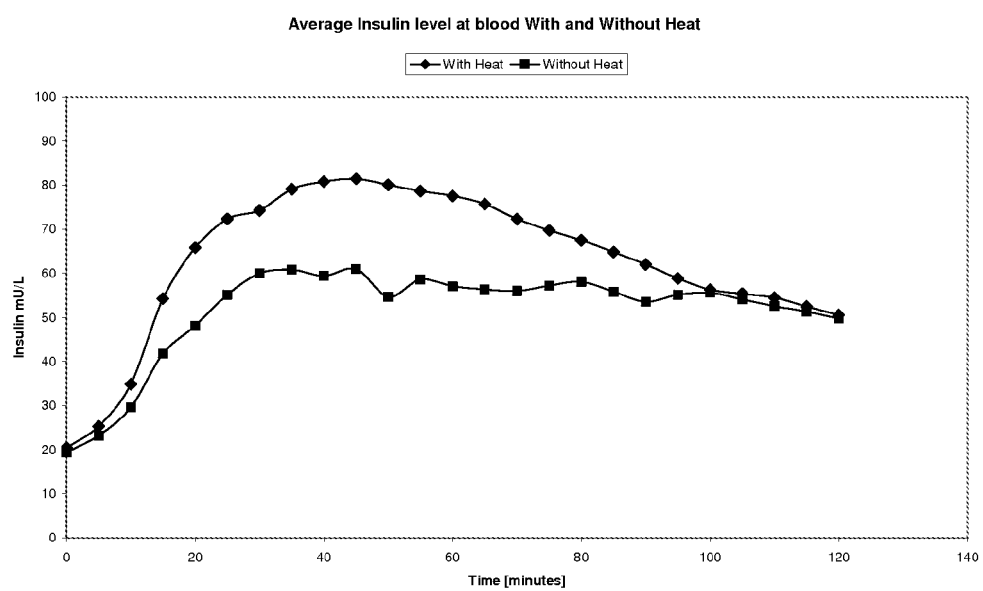
FIG. 26*b* illustrates an example of a graph of the insulin pharmacokinetics with and without treatment, according to some embodiments of the present invention.

The same protocol and meal tolerance test protocol, in which diabetic patients had liquid meal and used the same dose of insulin bolus (0.15 U/kg) using their insulin pump, again with and without heating the infused region using the same device. The insulin blood concentration was measured on blood samples using insulin immunoassay kit of DRG. The pharmacokinetics results or the profile insulin concentration in the blood after bolus infusion from both experiments is shown in FIG. 26*b*. The graphs are the average of 11 subjects that had bolus of insulin 0.15 U/kg with and without the heating device. The graph shows clearly that the blood insulin concentration for the same amount of infused insulin is significantly higher at the initial 2 hours when using said heating device. The 1 hour area under the curve improvement or the amount of absorbed insulin in the blood is more then 30%. This improvement in the insulin pharmacokinetics leads to improvement in the insulin pharmacodynamics, such as shown in FIG. 26*a*, reducing the time to onset of action, reducing the time to peak action and the other effects described before.

Medical and/or Cosmetic Devices for Drug Delivery

Some embodiments of the present invention relate to a method and device for improving the performance of implantable devices or of devices placed on the skin. Combination of radiation sources and/or heat and or mechanical vibrations and or suction is applied to the tissue automatically by attaching the device of the present invention next to an implantable device, a percutaneous catheter, or a device placed on the skin serving either as a sensor, a catheter or a module that secret to the tissue (the first device). The device of the present invention can also be part of the catheter which has one section inside the tissue and another section that connects to a unit outside the tissue. The individual excitation source properties, or the combination of excitation sources as well as the properties of each excitation source (such as amplitude, phase, frequency) as well as the relative ratio and timing between the various excitation sources may be automatically controlled by a processor in order to achieve a desired response from the tissue next to the device. Activation of the first device automatically triggers the operation of the device of the present invention or the device of the present invention detects operation of the first device and starts to operate by applying excitation to the tissue, or the device of the present invention operated at predetermined times for a predetermined length of time. The tissue response to the excitation enhances the functionality of the first device. This enhancement may be induced but not limited by altering the kinetics of molecules transport between the first device and the tissue. Or the tissue response to the excitation enhances the kinetics of molecules transport between the catheter tip placed inside the tissue and the tissue around it.

The excitation or excitation-detection device will be referred to as the second device. The first device and the second device may be placed either inside the tissue, or on the skin or the second device may be placed outside the tissue while the first device is inside the tissue. The first device may be mechanically or electronically, or mechanically and electronically connected to the second device or the second device may be placed on the surface of the tissue above the first device or the second device may be a section of the first device.

The second device includes at least one of the following excitation sources or at least one combination of two from the following excitation sources: at least one heat source (like a heat resistor) or at least one suction port activated by a pump or at least one mechanical vibration source or at least one ultrasound transmitter or at least one ultrasound transducer, or at least one electrical electrode or at least one light or laser light emitting source, or at least one optical fiber, or at least one electromagnet or permanent magnet or a combination of more then two of heat, vibrations, suction, ultrasound, light, electronic electrode, magnet. The light source may emit pulsed light or CW light and the pulsed light source may further emit pulses that are appropriate to generate photoacoustic or thermoacoustic signals on the first device and/or in the tissue surrounding the first device.

The combination of excitations generated by the second device reacts with the region of tissue surrounding the first device and the reaction enhances the functionality of the first device. Or the tissue response to the excitation or combination of excitations enhances the kinetics of molecules transport between a catheter tip placed inside the tissue and the region of tissue around it.

The second device includes at least two parts wherein one part is used to fix the second part on its position relative to the tissue. One part may further be disposable while the other part that contains the electronics is reusable. However, it is clear to those skilled in the art that the device may be made in one part or in more than one part and that the electronics, the controller, the power supply and field generating modules may all be housed in one case or in more than one case. The power supply may also be a battery or the device may be connected to a power line.

Some embodiments relate to a percutaneous catheter that is used together with insulin pump to deliver insulin subcutaneously this part is referred to as the "the first device". The second device is placed on the tissue surface above the catheter and the stimulation from second device reduces bio-foiling of the catheter. The second device may function independently from the first device or it may communicate (in wire and/or wireless modes) to the first device. The second device may also use the power source of the first device.

In some embodiments, the percutaneos catheter—"the first device" emits low RF field generated between the wire and an external electrode or between electrodes on the wire "the second device". This field alters the tissue response to the foreign body and allows better functionality of the catheter.

In some embodiments, an indwelling or implantable device—"the first device" is made in structure and material composition to enhance the mechanical vibrations caused by the second device. Such enhancement can be achieved by making the body of the first device to resonate with the radiation field generated by the second device which can be of ultrasound waves. The material of the first device can be made to absorb light radiation and emit ultrasound wave by the photoacoustic or thermoacoustic effect. An electrode formed along the first device can interact with an applied electromagnetic field or magnetic field generated by the second device.

In some embodiments, the percutaneous catheter is a catheter that is used together with insulin pump to deliver insulin subcutaneously—"the first device". The second device, placed on the surface of the tissue excites the tissue with light or heat or mechanical vibrations or suction or Electrical current or Ultrasound or RF frequencies or a combination of at least two from heat, vibrations, suction, ultrasound, light, electronic electrode, magnet, RF frequencies that causes a reaction to occur in tissue next to the catheter. This reaction stimulates the tissue reduces bio-foiling and improves the dynamics of insulin transfer tissue.

In some embodiments, the percutaneous catheter is a catheter that is used together with insulin pump to deliver insulin subcutaneously—"the first device". The second device, placed on the surface of the tissue irradiates the tissue with light that causes photoacoustic or thermoacoustic reaction to occur on the percutaneous catheter. This reaction stimulates the tissue reduces bio-foiling and improves the dynamics of insulin transfer to the tissue.

In some embodiments, the first device is an adhesive pad containing adhesive to the skin and matching layer. The matching layer may be liquefied gel or solidified gel. The composition of the said gel may include molecules other then water. The second device includes a power source and exciting source. The power source may be a battery. The battery may be replaceable or embedded in the device. The exciting source may be detachable from the device or embedded in it. The battery provides power to the exciting source. The exciting source is a combination of light or laser light illumination and ultrasonic source. The excitation from the second device is used to enhance the transport kinetics of molecules present in the gel to the tissue. The first and second devices may be mechanically configured in two cases or in one case.

Figure 48:
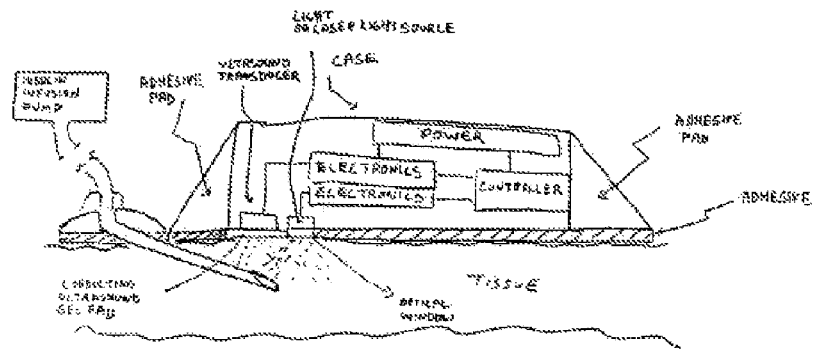
FIG. 48 illustrates an exemplary drug delivery device, wherein the first device or the first part is an indwelling catheter of an infusion pump inserted to the tissue or to a blood vessel, according to some embodiments of the present invention.

FIG. 48 illustrates an exemplary drug delivery device, wherein the first device or the first part is an indwelling catheter of an infusion pump inserted to the tissue, according to some embodiments of the present invention. The second device or the second part combines ultrasound transducer with light or laser light source in one case. The case further includes electronic driving circuits, controller and power source. The case is positioned over the skin above the catheter of the first device by an adhesive tape with mechanical attachments to hold the case on the tape.

Figure 49:
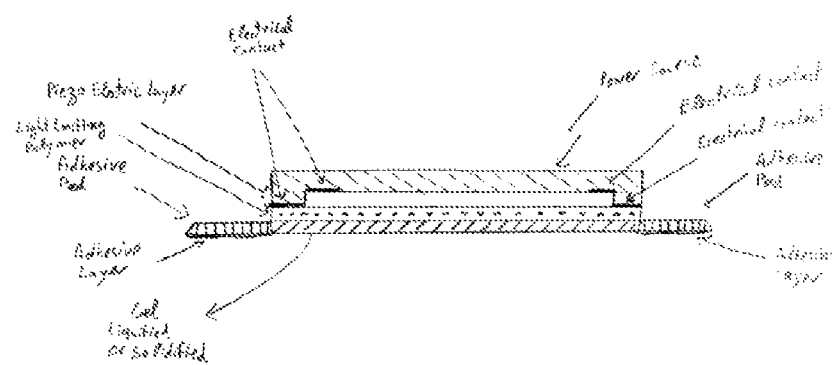
FIG. 49 illustrates an exemplary drug delivery device, wherein an attachment to the skin includes a power source, exciting source, adhesive to the skin and matching layer between the exciting source and the skin, according to some embodiments of the present invention.

FIG. 49 illustrates an exemplary drug delivery device, wherein an attachment to the skin includes a power source, exciting source, adhesive to the skin and matching layer between the exciting source and the skin, according to some embodiments of the present invention. The matching layer may be liquefied gel or solidified gel. The composition of the said gel may include molecules other then water. The power source may be a battery. The battery may be replaceable or embedded in the attachment. The exciting source may be detachable from the attachment or embedded in it. The battery provides power to the exciting source. The battery can be made by ink deposition on a polymer material—Power Paper Ltd., Petch Tikva, Israel www.powerpaper.com. The exciting source is a combination of light or laser light illumination and ultrasonic waves source. The exciting source ultrasonic part can be made from a thin layer piezoelectric material put on a layer of light emitting polymer such as poly phenyl vinylene (PPV). The thin piezoelectric material layer can also be made of Polyvinylidene Fluoride (PVDF). If the layer of piezoelectric polymer can be made to pass the light emitted by the layer of light emitting polymer then the layer of light emitting polymer can be on top of the piezoelectric material layer.

Method and System for Drug Delivery with Tissue Irradiation

Some embodiments of the present invention relate to apparatuses, methods and devices to improve and stabilize the pharmacokinetics and pharmacodynamics of a drug infused into the tissue by a catheter and absorbed into the blood system. The apparatus and devices described herein apply additional treatment or stimulation to the region of tissue where the drug is infused. The additional treatment includes electromagnetic radiation, which as described herein more includes light irradiation of the tissue.

According to some embodiments, there is provided a device for improving the performance of catheter based drug delivery devices, whether the catheter is an external element to the pump or an element embedded into a pump mechanism, which also combines electromagnetic radiation treatment, for example, from a source of electromagnetic radiation. Application of the electromagnetic radiation treatment may be performed, in some embodiments, substantially at the same time as the drug infusion operations are performed. The device described herein can also be part of the catheter which has one section inside the tissue and another section that connects to a unit outside the tissue.

The electromagnetic radiation treatment is applied to a tissue region to which the drug is delivered to expose it to electromagnetic radiation and/or to an effect caused by electromagnetic radiation to improve the drug pharmacokinetics or pharmacodynamics. The effect may include, but is not limited to, heating, acoustical stimulation, light based stimulation and the like.

The present disclosure radiation treatment of a region of a tissue by any type of electromagnetic radiation in conjunction with the infusion of the drug into a body of a patient, including optical radiation, to cause different type of treatment effects (or stimulation).

For example, the described herein is the use of optical radiation to treat the skin so as to achieve improvement of pharmacokinetics and/or some other pharmaceutically related parameter for the administration of a drug through a pump system, for example through infusion. Treatment of tissues with optical radiation according to the present disclosure may be performed with light at a variety of wavelengths from infrared to low ultraviolet or shorter than ultraviolet wavelengths. Furthermore, a variety of instruments may be used for providing such light, including, but not limited to, lasers, such as laser diodes, including single elements or laser diode bars or arrays, VECSELs, or solid state lasers, fiber lasers, other types of lasers, LEDs, mercury arc lamps, xenon arc lamps, other types of lamps and the like. The light source may emit pulsed light or continuous wave light, or a combination thereof. If pulsed light is emitted, then, in some embodiments, one or more characteristics of the pulses are determined according to one or more pharmaceutical requirements of the drug being administered.

The instruments may emit a broad spectrum light and/or a narrow spectrum light. If the instruments emit a broader spectrum light than is required, one or more filters may be employed to reduce the spectrum of light treating the tissue. Radiation devices used to irradiate the tissue may also include mirrors, lenses, fiber optics and other like components to focus the light in a specific region or regions.

In circumstances where the radiation unit generates light to be applied to the tissue, the light may include wavelengths in the range of from about 300 to about 3,000 nm. The light may be a broad spectrum light, including a majority of such wavelengths. In some embodiments, generated light includes radiation in the near infrared wavelengths and/or shorter wavelengths of light and/or longer wavelengths of light. For example, for near infrared light, the wavelengths include the wavelength range from about 700 to about 1000 nm. For light having longer wavelengths, the wavelengths are at the infrared region. Higher frequency electromagnetic radiation, such as electromagnetic waves in the Tera Hertz range (corresponding to waves in the millimeter range, microwaves or RF (radio frequency) are also possible.

In some embodiments, low frequency RF energy is applied at a level (e.g., power level) which is non-ablative. For example, radiofrequency energy in the range of 50 to 2,000 kHz may be selected so as to be non-ablative for the subject. RF energy may be applied as a plurality of pulses. In some embodiments, a single or multiple electrodes may be used. The electrodes may contact the skin and may, in some implementations penetrate the skin. In some embodiments, a catheter is used for drug delivery with at least one electrode being incorporated in the catheter. Each electrode may be constructed from one or more conductive metals, including, but not limited to, platinum, iridium, gold, silver, stainless steel, Nitinol, or an alloy of these metals.

In some embodiments, the device includes a catheter inserted into the tissue to infuse a substance into that tissue region. The tissue region can be one of the skin layers or the subcutaneous tissue or deeper tissue elements within any organ or viscera.

The catheter may have also a securing mechanical part or device that adheres to the skin and secures the catheter into its location to prevent it from being pulled out accidentally. The proximal end of the catheter may be connected to a drug delivery device which controls the infusion profile of the drug. The drug delivery device controls also the additional treatment (e.g., irradiation) applied to the infused tissue area. The drug delivery device and the treatment module (e.g., the radiation unit) may be in communication with other to communicate data based upon which operations of the drug delivery device and the radiation unit may be performed. The communication may be either wired or wireless. Parts of the treatment device may be disposed inside the drug delivery device or outside of it. The drug delivery device may include a drug delivery pump, such as an insulin pump.

The pump may include an electronic processing unit to determine, according, for example, to a predetermined protocol, implemented procedure, any additional inputs and drug infusion profile when and to what extent electromagnetic radiation should be applied. The pump electronic processing unit may, in some embodiments, communicate with a processing unit of the treatment module. The processing unit of the treatment module determines according to a predetermined protocol, a procedure, and according to drug infusion profile when and to which extent the electromagnetic radiation should be applied. The pump electronic processing unit and/or the treatment device processing unit regularly query the status of the pump by, for example, using built-in communication capability of the pump. The received data is then used to determine the electromagnetic radiation treatment parameter(s).

Sensors in communication with the source of electromagnetic radiation may detect the drug being delivered into the patient's body through the catheter. In response to the detected drug delivery, the treatment module applies a treatment (e.g., radiation) according to a predetermined protocol or procedure. In some embodiments, the treatment module includes a sensor that can detect the drug infusion flow inside the catheter and deliver the information to the device processing unit, which then determines the electromagnetic radiation treatment parameter(s). The drug flow may be detected, for example, optical sensors that detect the drug flow through the catheter (e.g., in circumstances in which a transparent or translucent catheter is used), a laser Doppler sensor, an ultrasonic Doppler sensor, a pressure sensor, a conductivity sensor and/or an inductance sensor that can measure changes in the flow rate of the infusion fluid, under induced magnetic field (for example). The drug flow sensor may detect not only the existence of a drug infusion flow, but also the infusion rate, and uses the information to determine, at least in part, the treatment procedure. The drug infusion sensor may detect the electromagnetic or acoustic emission of the drug delivery pump motor or electronics. In some embodiments, the devices detect additional parameters pertaining to the tissue and use that information as well to determine or control the treatment procedure (e.g., compute parameters germane to the treatment procedure).

Referring to FIG. 18, the light source can be disposed in a third unit (not shown) and the generated light can be delivered with an optical fiber, or several fibers, to the optical radiation element 301. The third unit can be attached externally to the drug delivery device to improve the user's comfort. Under these circumstances, the fiber or fibers can be disposed proximate to the catheter tube 303, for example, the optical fiber(s) can be attached to the outer shell defining the catheter tube 303 and extend along the tube. The optical fiber(s) and the tube 303 could then be separated at around the drug delivery device such that the drug catheter tube 303 would be extended and be coupled to the drug delivery device (not shown), and the fiber or fibers would be connected to a third unit that includes at least one light source. The third unit may also include a power source and a controller (not shown). When drug delivery starts, e.g., during a drug bolus delivery, the occurrence of the drug delivery operation can be communicated to the third unit, either actively by direct communication between the drug delivery device and the third unit, or passively through a signals generated by a sensor detecting the occurrence and/or commencement of the drug delivery operation e.g., electromagnetic emission by the drug delivery device.

The optical radiation element 301 can be disposed in a catheter securing unit such as shell (not shown) encasing the catheter tube 303. One effect caused by the electromagnetic radiation is heating of the radiated tissue region. The application of electromagnetic radiation may be used to control the temperature of the tissue region into which the drug is delivered. Temperature control can be used for setting a profile of temperature rise at a known rate, followed by temperature stabilization for a pre-determined time period and concluding by returning to the tissue to its regular temperature. This profile can be applied by, for example, illuminating the drug infused tissue region with electromagnetic radiation. The temperature profile can be applied to a larger region than the drug infused tissue region to circumvent light scattering in the tissue. Doing so may improve blood perfusion in the vicinity of the drug infused tissue area, thus further increasing drug absorption rate into the blood system through increase of the available absorption volume. The temperature profile can be applied to a region smaller than the drug infused tissue region, thus enabling conservation of energy (e.g., in circumstances in which a battery with a limited energy capacity is used).

Figure 27:
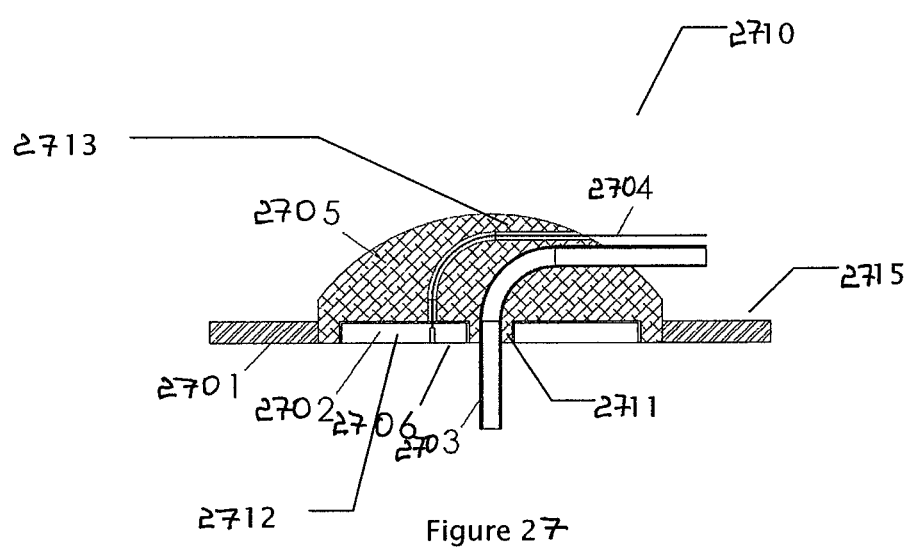
FIG. 27 schematically describes a catheter for drug delivery combined with a radiation element attached to the skin around the catheter.

Another exemplary device to perform irradiation of radiation at the area of a tissue into which the drug is delivered is schematically shown in FIG. 27. As shown, a treatment device 2710 includes an infusion catheter 2703 and at least one radiation source element 2702 attached to the skin (not shown) in an area around the catheter 2703. The treatment device 2710 further includes a circular structure 2705 with a hole 2711 in its center for the catheter tube 2703 that is subcutaneously inserted into the skin tissue. The other side of the catheter 2703 is connected to the drug delivery pump (not shown). Radiation source element 2702 may include one or more light sources 2712.

As further shown, a temperature sensor 2706 is disposed in contact with illuminated skin region to regulate the skin temperature to the required temperature according to a temperature control procedure or temperature profile. Regulation of the tissue temperature may be based on measured temperature values detected at a sensor 2706. The temperature sensor 6 is connected to a controller unit 2713 disposed in the catheter 2703 or in the drug delivery device (not shown) and/or in an third unit (not shown). In some embodiments, the temperature is between 32-40° C. This temperature range has been found to have sufficient effect on the tissue while not causing damage or injury to the tissue. Temperature stabilization profiles/procedures may be executed using controllers and/or ASICs. A skin cooling system may be used, as described, for example in U.S. Pat. No. 5,344,418, the content of which is hereby incorporated by reference in its entirety. The skin or tissue damage depends on the applied temperature and the heat exposure time. For an exposure period that is relatively short e.g., a few minutes, even higher temperatures, for example, temperatures of up to of 42° C. may be used. Under some circumstances, lower temperatures may be required. For example, Novolog Insulin requires maximal temperature of 37° C. in the insulin infused tissue region. However, under those circumstances, the skin temperature can be slightly higher than that, as the insulin infused tissue region could have a lower controlled temperature.

An additionally and/or alternatively, a temperature sensor (not shown) is located inside the catheter tube 2703. This temperature sensor enables more direct control of the temperature of the drug infused tissue region, in turn enabling potentially better stabilization of the drug chemical processes or pharmacokinetics or absorption into the blood system or pharmacodynamics that can be achieved. In situations in which the drug delivered is insulin, it is important to reduce the variability of the temporal profile of the insulin absorption into the blood and to more closely regulate temperature control.

The at least one radiation source element 2702 and one or two of temperature sensors may be connected to the drug delivery pump through a cable 2704. Under these circumstances, the drug delivery pump includes the power source and the controller of the treatment process (not shown).

A circular structure 2705 that covers at least one radiation source element 2702 may be thermally isolating such that the flat circular structure 2705 reduces the heat dissipation to the environment in Use of the circular covering structure 2705 also facilitates the thermal regulation (e.g., stabilization) of the infused tissue area in situations in which the environments and/or ambient temperature undergo changes.

The at least one radiation source element 2702 generates radiation to treat the drug infused tissue area as described herein. In some embodiments, the tissue from any heat produced in the course of generating the actual radiation applied to the tissue. For example, if the radiation includes light, then the transformation of electrical energy into light energy, whether by radiation source resistance or non-radiative transitions. Under these circumstances, the combination of generated heating and radiation is applied to the tissue to better and/or more efficiently produce the desired effect.

In some embodiments, the device 2710 as shown in FIG. 27 is attached to the skin with an adhesive tape 2715. The adhesive layer 2701 of the tape 2715 can also cover the at least one radiation source element 2702, for example, with a transparent adhesive. The adhesive tape 2715 is initially covered with a laminate (not shown) that is peeled off by the user before insertion of the catheter 2703 and the radiation source element 2702. Generally, to facilitate catheter insertion the device is supplied with a sterile needle disposed inside the catheter 2703 (not shown) that is removed after insertion of the catheter 2703 into the required tissue area. The adhesive layer of tape 2715 may partially absorb the electromagnetic radiation to increase the outer layer of the skin heating, which may be required for certain heating depth distribution for optimization of heating profile and/or the heating efficiency.

Figure 28:
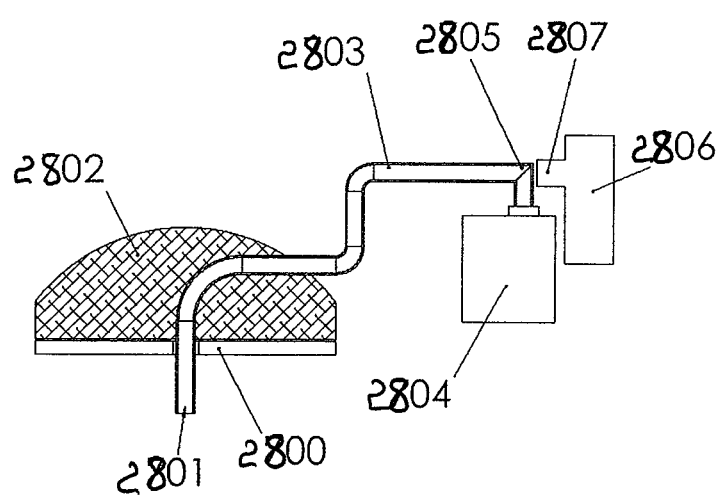
FIG. 28 schematically describes a catheter for drug delivery combined with a radiation source that guides the light through the catheter tube.

Referring to FIG. 28, another exemplary treatment device is shown. The treatment device includes a catheter tube 2803 configured to direct electromagnetic radiation through the tube and to illuminate radiation emitted at the tube end 2801 at the drug infused tissue region (not shown) As shown, the light from the at least one radiation source 2806 is coupled into tube 2803 near the drug delivery device 2804 through a light coupler 2807. The radiation source may be part of the drug delivery device 2804. Alternatively, a radiation source 2806 can be housed in a separate third unit as shown, that is attached to the drug delivery device 2804. To facilitate light coupling into the tube 2803, the radiation source 2806 may be attached to the tube 2803 at the light coupler 2805, and be otherwise disposed so as to be substantially aligned with the longitudinal axis of the tube, while the drug flowing from drug delivery device 2804 is enters the tube 2803 from the side. Generated light is thus directed through the length of tube 2803 until it decoupled at the tube end 2801 located proximate to the drug infused region. The decoupled radiation is subsequently absorbed by the tissue region. The generated light is directed through any bend in the tube 2803

The catheter tip 2801 may be secured to the skin using catheter securing device 2802 with an adhesive layer 2800. In some embodiments, the securing device 2802 also includes at least one temperature sensor on the skin, the catheter, or at the drug infused tissue region to facilitate temperature regulation of the tissue. The temperature of the drug infused tissue region may be monitored non-invasively through the catheter, for example, by measuring the tissue IR emittance or by implementing other procedures for optical non-invasive temperature monitoring.

Figure 29:
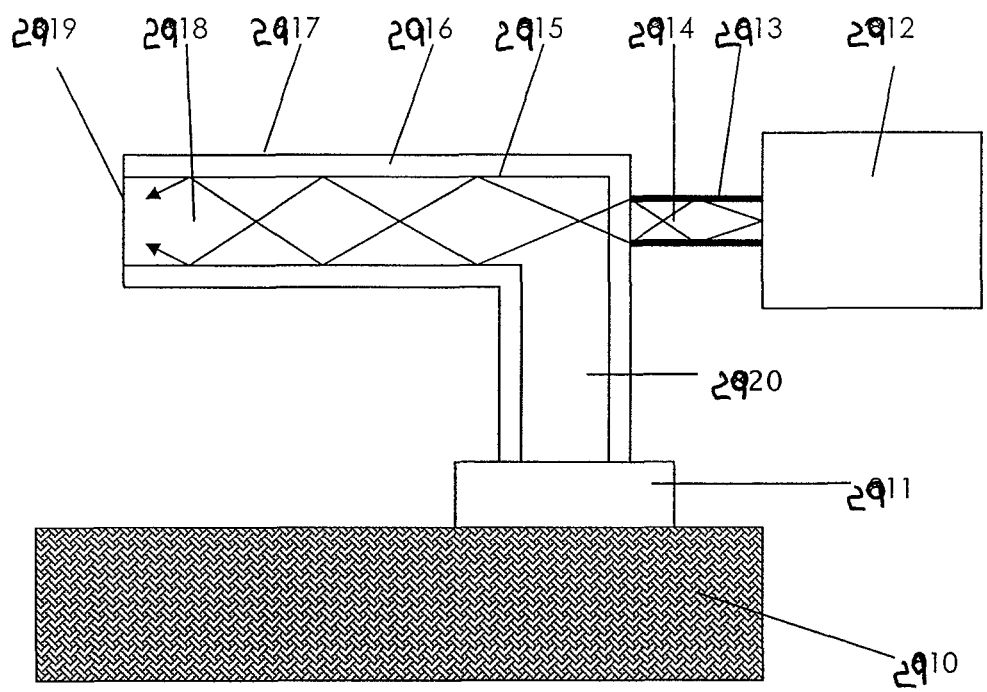
FIG. 29 schematically describes a drug delivery device combined with a radiation source that guides the light through the catheter tube.

Referring to FIG. 29, an exemplary device to couple and direct light through a tube that also carries a drug is shown. In some embodiments, the light is guided inside the drug delivery tube 2919 by the tube walls 2916. The material of tube walls 2916 is selected based on the type of light being guided and to provide acceptable light compensation performance for any light scattering that occurs. The drug is delivered by a drug delivery device 2910 through a tube connector 2911. At least one light source is shown schematically by box 2912. Generated light rays 2914, shown schematically by the bouncing line pattern is directed and/or controlled using optical device (e.g., lenses, couplers, etc.) or the waveguide 2913 to provide appropriate coupling efficiency into drug tube 2919. The difference between the refraction index of the drug 2918 and the tube wall 2916 enable the light rays 2914 to propagate through the tube To achieve efficient guidance of the light, the core material in the waveguide (which in these circumstance will include the drug material 2918) is required to have a higher index of refraction than the walls 2916 (the walls of the waveguide are referred to as the "cladding"). For example, in some embodiments, a drug is administered which, when diluted in water, has an optical index of refraction of approximately 1.33. If, under these circumstances, the tube wall 2916 is made from a polymer having an index of refraction of approximately 1.4-1.5, then light guidance will not be efficient (because the waveguide's wall have an index of refraction higher than that of the medium constituting the core). However, the efficiency of light guidance can be significantly improved by choosing polymers having a lower index of refraction for the tube wall 2916 and/or coating the inner side of the tube 2915 (i.e., the surfaces of the tube wall 2916) with a thin layer of light reflecting coating 2920 that includes, for example, one or more metals such as aluminum, silver, gold, etc. The reflecting coating can be coated by a protection layer made of polymer or other biocompatible materials. Under these circumstances, the light will be guided through the resultant coated tube with very small loss. The external surfaces 2917 of the tube walls 2916 may also be coated with a reflective coating.

The light wavelength is selected to have a very low absorption rate by water. Suitable light waves are those having wavelengths in the range of 300-1300 nm. The inner coating 2920 can be also of a polymer having a low index of refraction, to achieve better guidance of the light.

Figure 30:
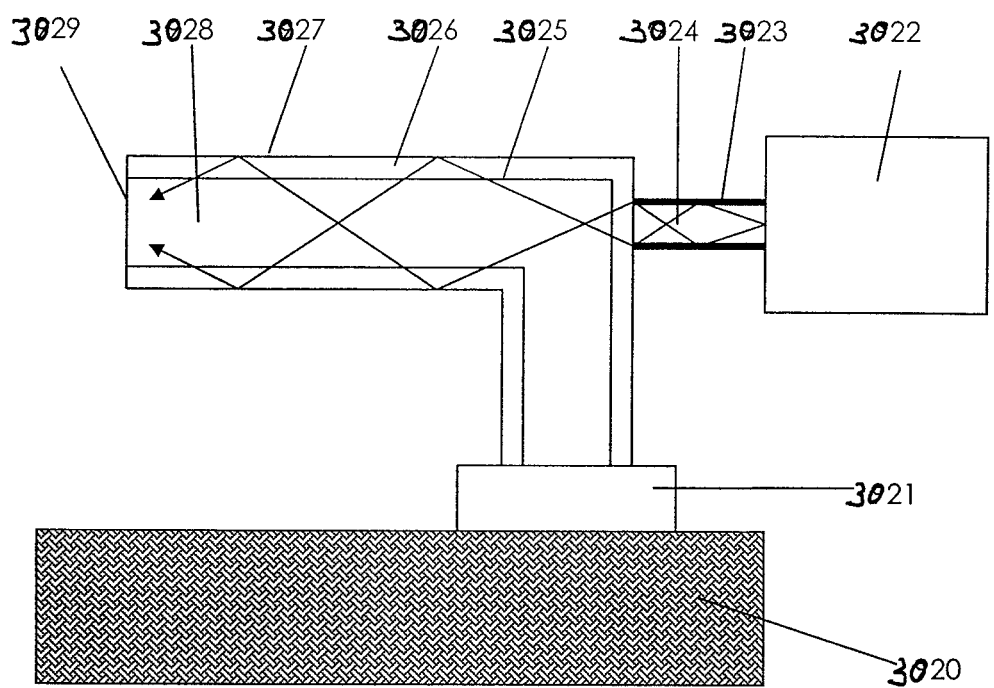
FIG. 30 schematically describes a drug delivery device combined with a radiation source that guides the light through the catheter tube.

Referring to FIG. 30, showing another exemplary treatment device in which the drug delivery tube also functions as a waveguide, the outer side of the drug delivery tube 3029 can be coated with a reflecting coating 3027. A drug delivery device 3020, a tube connector 3021 and a light source 3022 may be similar to the respective components/modules shown in FIG. 29. The optical shaping coupling element 3023 is configured to optimize the coupling efficiency for light (shown schematically as the bouncing ray lines) 3024. Under these circumstances, the light 3024 is guided through the drug solution 3028 (constituting the waveguide's medium core) and the transparent wall of the tube 3026. The reflecting coating may also be covered by a protection layer. Such a waveguide implementation can also be used without coating the outer surfaces of the tube 3026 with the reflecting coating 3027 because the index of refraction of air (1) is smaller than the index of refraction of the polymer tube 3026. However, any object touching the tube, for example, the abdomen of the patient could induce light leakage. In some embodiments, the tube wall 3026 is made of two layers with different indices of refraction such that the outer layer has smaller index of refraction and serves as cladding for the optical waveguide Similar to the arrangement shown in FIG. 29, the walls 3026 may also be coated with a reflective coating 3025.

Figure 31:
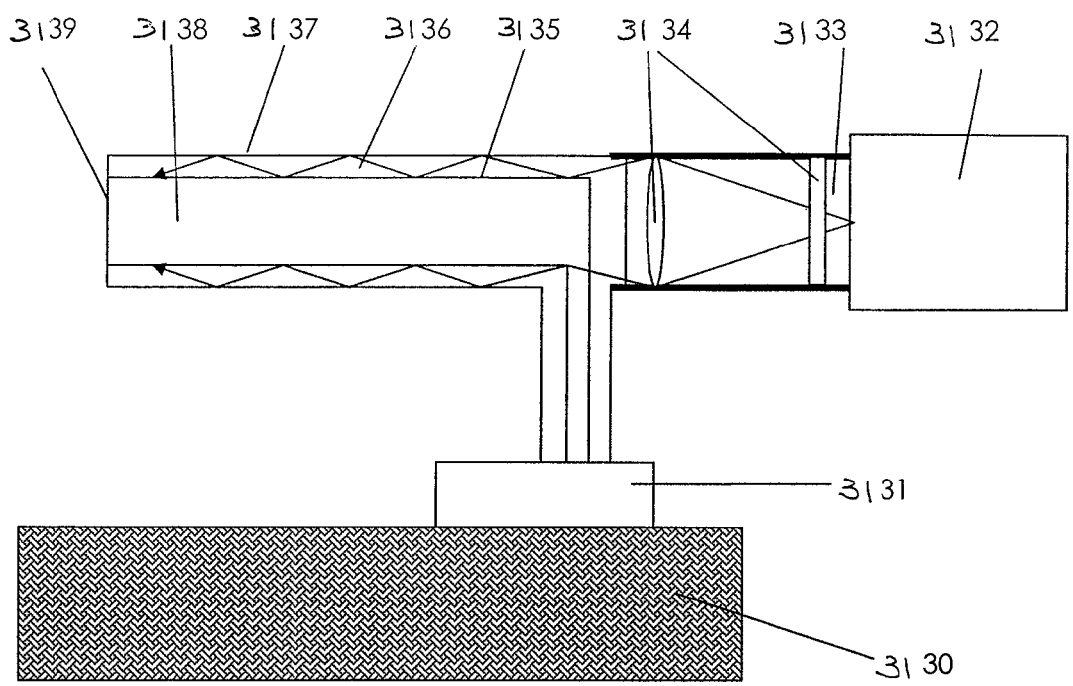
FIG. 31 schematically describes a drug delivery device combined with a radiation source that guides the light through the catheter tube.

Referring to FIG. 31, another waveguide implementation is shown. In the arrangement of FIG. 31, the light 3136 is shown schematically by bouncing line rays in the tube wall. A drug delivery device 3130, a drug delivery tube 3139, a tube connector 3131 and a radiation source 3132 may be similar to the respective components/modules described in relation to FIGS. 29 and 30. The optical shaping coupling element 3134 is mounted in mechanical adapter 3133. Reasonable (possibly optimal) light coupling efficiency can be achieved by structuring the waveguide section as a circular ring having a shape similar to the shape of the tube 3139 in cross-section. To couple the light into the circular ring waveguide, suitable optical elements, such as lenses, aspherical components, diffractive optical elements, fiber illuminators and/or mounted light sources having a circular shape may be used. For example, an optical shaping coupling element 3134, e.g., a lens, can be used to cause light generated at the light source 3132 to be coupled into the circular ring-shaped waveguide. The arrangement shown in FIG. 31 may also be used without the inner coating 3135 and/or outer coating 3137 of the tube because the index of refraction of air (1) is smaller than the index of refraction of the polymer tube wall 3136. In some embodiments, the index of refraction of the drug solution 3138 is also smaller than the tube wall's index of refraction. However, under those circumstances, any object touching the tube, such as, for example, the abdomen of the patient, will induce light leakage.

In some embodiments, the reflecting coating is covered also by a protection layer. The tube wall 3136 may be made of two layers having different indices of refraction such that the outer layer and the drug solution have smaller indices of refraction and serve as the cladding, while the inner layer of the wall functions as the waveguide core to guide the light. The tube wall 3136 may be made of three layers with different indices of refraction such that the outer layer and the inner layer have smaller indices of refraction and thus serve as the cladding, while the middle layer of the wall serves as the core to guide the light.

Figure 32:
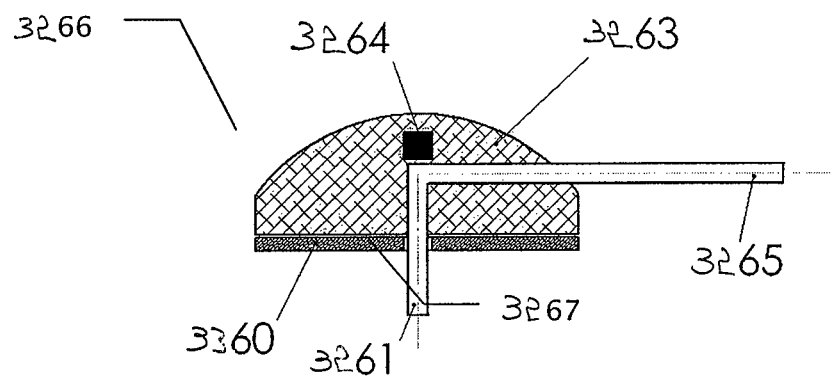
FIG. 32 schematically describes a catheter for drug delivery combined with a radiation source that guides the light through the catheter tube.

Referring to FIG. 32, an exemplary treatment device 3266 in which an electromagnetic radiation element is located within the catheter securing device and radiates the tissue through the catheter is shown. In this arrangement, an infusion catheter 3265 is combined with at least one optical radiation element 3264 that couples the light into a proximal part 3261 of the infusion catheter 3265. A catheter securing device 3266 includes a circular structure 3263 with a hole 3267 in its center through which the catheter tube 3261 enters the subcutaneous tissue. The circular structure 3263 is attached to the tissue with an adhesive layer 3260. The adhesive layer 3260 may be initially provided with a laminate (not shown) that is peeled off by the user before insertion of the catheter and the connection of the optical radiation element 3264. Electromagnetic radiation source(s) can illuminate the drug infused tissue region through the skin. In this arrangement the adhesive layer 3260 can be either around the illuminated skin area or cover the illuminated skin area with an adhesive that is optically transparent in the relevant optical wavelength(s). The other side of the catheter 3265 is connected to a drug delivery device (not shown).

Generally, for catheter insertion, the device may be supplied with a sterile needle (not shown) disposed inside the catheter that is removed after insertion of the catheter. The power source for the optical radiation element 3264 can be disposed in the catheter unit 3266. Alternatively, the power source for the optical radiation element 3264 may be disposed in the drug delivery device and connected with a wire to the optical radiation element 3264. Alternatively, in some embodiments, the power source for optical radiation element 3264 can be disposed in a third unit (not shown) connected with wires to the optical radiation element 3264. In some embodiments, the third unit can be attached externally to the drug delivery device to improve the user comfort.

Figure 33:
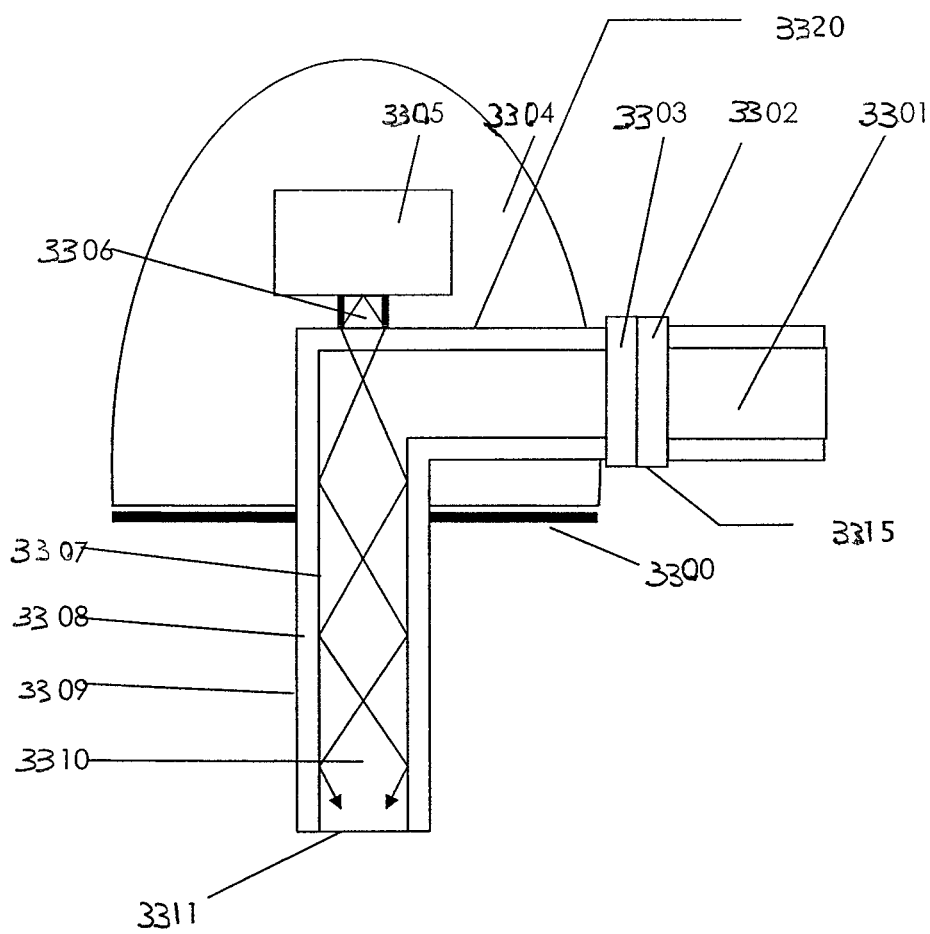
FIG. 33 schematically describes a catheter for drug delivery combined with a radiation source that guides the light through the catheter tube.

Referring to FIG. 33, another exemplary treatment device that includes a waveguide to irradiate radiation at the drug infused tissue area through a catheter end is shown. In the illustrated example of FIG. 33, the electromagnetic radiation is light. However, other types of electromagnetic radiation may be used to irradiate the drug infused tissue area. As shown, light from the at least one light source 3305 is coupled into a catheter 3310. The light source 3305 can be part of the catheter securing device 3304, as shown, or alternatively may be detachable (similar to the arrangement shown, for example, in FIG. 6). To facilitate light coupling into the catheter 3310, the light source 3305 can be aligned on the same longitudinal axis of the catheter tube 3310, while the drug enters catheter tube 3310 at the side of the tube.

In some embodiments, the drug is imparted from the drug delivery device through a tube 3301. The tube 3301 may include a connector 3315 having one section 3302 attached to the tube and a second matched section 3303 attached to the catheter 3310. The light, schematically depicted by the bouncing ray lines is guided through the catheter 3310 until it exits at the catheter end contacting the tissue enters the drug infused area where it is absorbed by the surrounding tissue of the area.

As further shown in FIG. 33, the light is guided inside the catheter tube 3310 by the tube walls 3308. The light is shaped and controlled (e.g., controlling the light's direction) using coupling optical component 3306 which may include a lens or some other type of optical device, or by a waveguide, to provide suitable coupling efficiency of the light into the catheter tube 3310. The light controlled by the coupling optical component 3306 passes through a transparent wall 3320 inside the drug delivery tube 3301. As previously explained, the light generally propagates within the tube 3301 because the difference between the refraction indices of the drug (functioning as the core medium) and the tube wall 3308. Thus, the light guidance characteristics of the waveguide can be improved by choosing a lower index of refraction polymers for the catheter tube 3310 or coating the inner side 3307 of the catheter tube 3310 with a thin layer of light reflecting coating, including coating that include one or more of aluminum, silver or gold. The reflecting coating can be coated by a protection layer of polymer or other biocompatible materials. Under these circumstances, the light will be guided by the coated tube and sustain only small losses. The outer side 3309 of the catheter tube 3310 is generally not coated.

In some embodiments, the light wavelength (or range) is selected so that small absorption of light by water results. For example, a suitable light wavelength range includes wavelengths in the range of 300-1300 nm. Use of light having a wavelength(s) in that range reduces light absorption by a solution containing the drug (which generally has a high concentration of water) thus preventing heating of the solution. These wavelengths may be used in situations in which the drug should not be heated above a maximum temperature, such as for drugs that include proteins for example.

A catheter tip 3311 may be secured to the skin using the catheter securing device 3304 with an adhesive layer 3300 in a manner similar to that described in relation to other figures of the present disclosure. At least one temperature sensor (not shown) may be placed on one or more of the skin, the catheter, or the drug infused tissue region. The at least one temperature sensor is configured to regulate (e.g., stabilize) the tissue temperature. In some embodiments, the temperature of the drug infused tissue region is monitored non-invasively through the catheter 3310, for example, by measuring the tissue IR emittance or other by using other optical non invasive temperature monitoring techniques.

Figure 34:
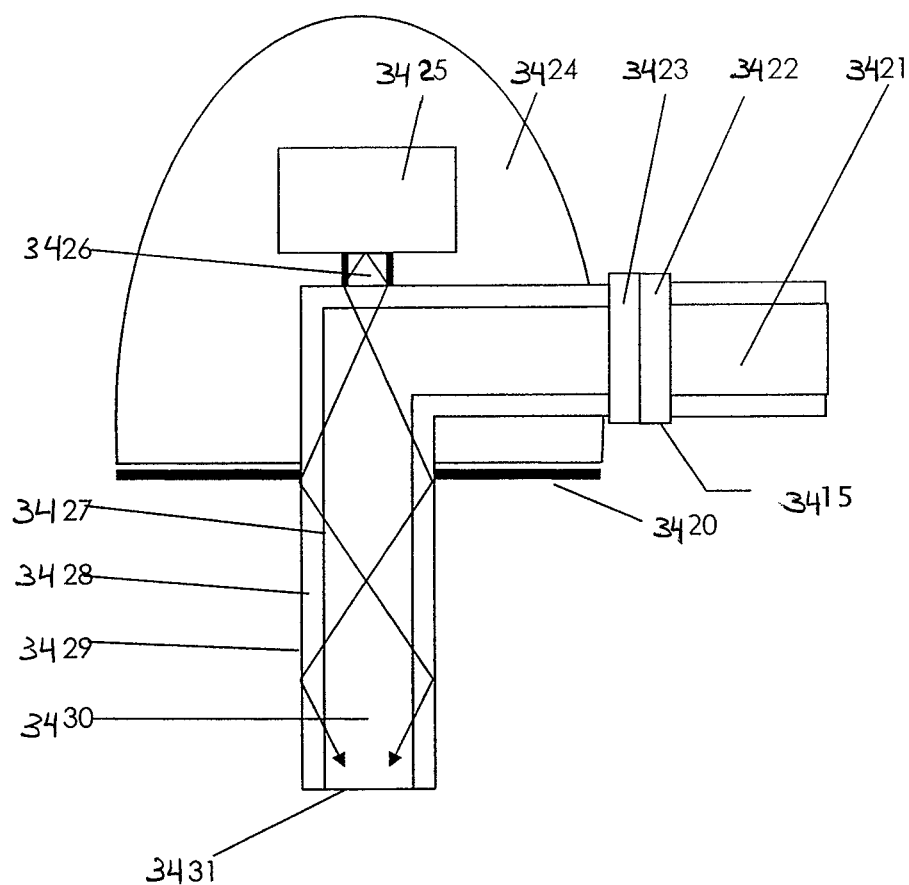
FIG. 34 schematically describes a catheter for drug delivery combined with a radiation source that guides the light through the catheter tube.

Referring to FIG. 34, in some embodiments, an outer side 3428 of the catheter tube can be coated with a reflecting coating 3429. A tube 3421, which delivers the drug from the drug delivery device (not shown) is coupled to a connector 3415 having sections 3422 and 3423. The device further includes a radiation source 3425 similar to the radiation source depicted in FIG. 33. An optical shaping coupling element 3426 used to efficiently couple light into the catheter tube. As shown in the arrangement of FIG. 34, light, depicted schematically by the bouncing ray lines 3430, is guided in both the drug solution and the transparent walls of the catheter tube 3428. The reflecting coating 3429 may be further covered by a protection layer. In the depicted arrangement, a coating may not be provided for inner walls 3427 of the catheter tube 3428.

The waveguide implementation of FIG. 34 can also be used without coating the outer side of the tube 3428 with a reflecting coating because the index of refraction of the air (1) is lower than the index of refraction of the tube 3428 (typically polymer based). However, when the light enters the catheter portion which is inside the tissue, the light will leak out of the waveguide because the tissue index of refraction is higher (see FIG. 36). The catheter portion at which the light should scatter out of the catheter tube may be coated with partially reflecting coating as will be described in greater detail below. In some embodiments, the tube wall 3428 is made of two layers with different indices of refraction such that the outer layer has smaller index of refraction and thus serves as cladding for the optical waveguide (not shown). In some embodiments, a catheter securing device 3424 with adhesive layer 3420 may be provided.

Figure 35:
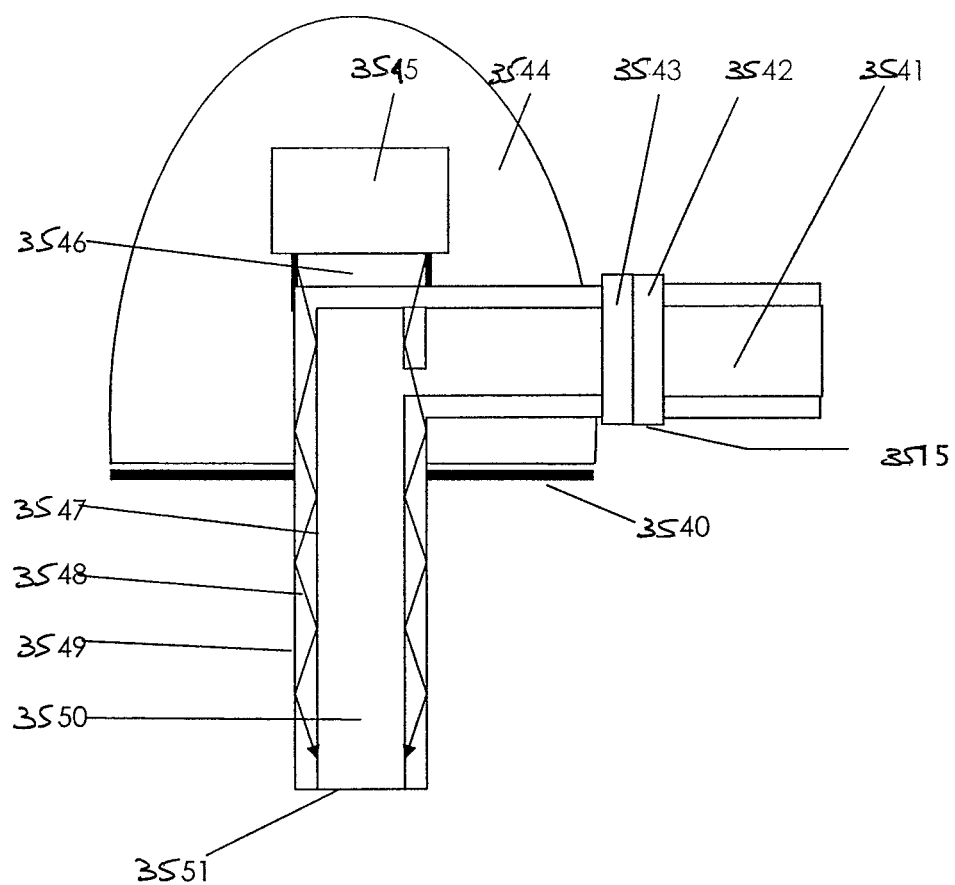
FIG. 35 schematically describes a catheter for drug delivery combined with a radiation source that guides the light through the catheter tube.

Referring to FIG. 35, another guidance device to implement a further guidance scheme is depicted. As shown, the light, represented schematically by the bouncing ray lines, is guided in a tube wall 3548 of a catheter 3551. A tube 3541 from the drug delivery device includes an connector 3515 with having, for example, sections 3542 and 3543 (similar to the configuration of the corresponding connector depicted in FIG. 33). The treatment device also include a radiation source 3545 (similar to that of FIG. 33). Also included is a catheter securing device 3544 with an adhesive layer 3540. An optical coupling element 3546 may be configured to couple radiation from the radiation source 3545 to the circular ring-shaped structure that guides the radiation to its exit point at the end of the catheter tube. Such optical shaping and/or control to properly couple the radiation into the circular ring-shaped guide can be achieved using, for example, one or more optical elements, such as lenses, aspherical components, diffractive optical elements. Additionally, the required optical shaping and/or control can also be implemented by mounting light sources with a circular shape or by using fiber illuminators to couple radiation from the radiation source to the guide. The guidance scheme depicted in the arrangement of FIG. 35 can be used without coating the tube 3551.

Alternatively, the outer wall 3549 of the catheter tube 3551, or the inner wall 3547 of the catheter 3551, or both, may be coated with a reflecting coating. The reflecting coating may be covered by a protection layer. In some embodiments, the catheter portion at which the light is emitted out of the catheter tube is coated with a partially reflecting coating. In some embodiments, the catheter tube wall 3548 is made of two layers with different indices of refraction such that the outer layer and the drug solution 3550 have smaller indices of refraction and thus serve as the claddings, while the inner layer of the wall 3548 serves as the waveguide core and guides the light. The second outer layer may cover only the catheter portion at which the light should be guided and ends at the catheter portion at which the light exits out of the catheter tube. In some embodiments, the tube wall 3548 is made of three layers with different indices of refraction such that the outer layer and the inner layer have smaller indices of refraction and serve as the claddings, while and the middle layer of the wall 3548 serves as the core to guide the light. The third outer layer may coat only the catheter portion at which the light should be guided and ends at the catheter portion at which the light exits out of the catheter tube 3551 (not shown). In some embodiments, the reflection coefficient of at least one of the reflecting layers is gradually decreased at the catheter portion at which the light exits out of the catheter tube to obtain more uniform illumination of the drug infused region (not shown). In some embodiments, the reflection coefficient of at least one of the reflecting layers is reduced in a specified profile at the catheter portion at which the light exits out of the catheter tube 3551 to get a required illumination profile of the drug infused region.

Figure 36:
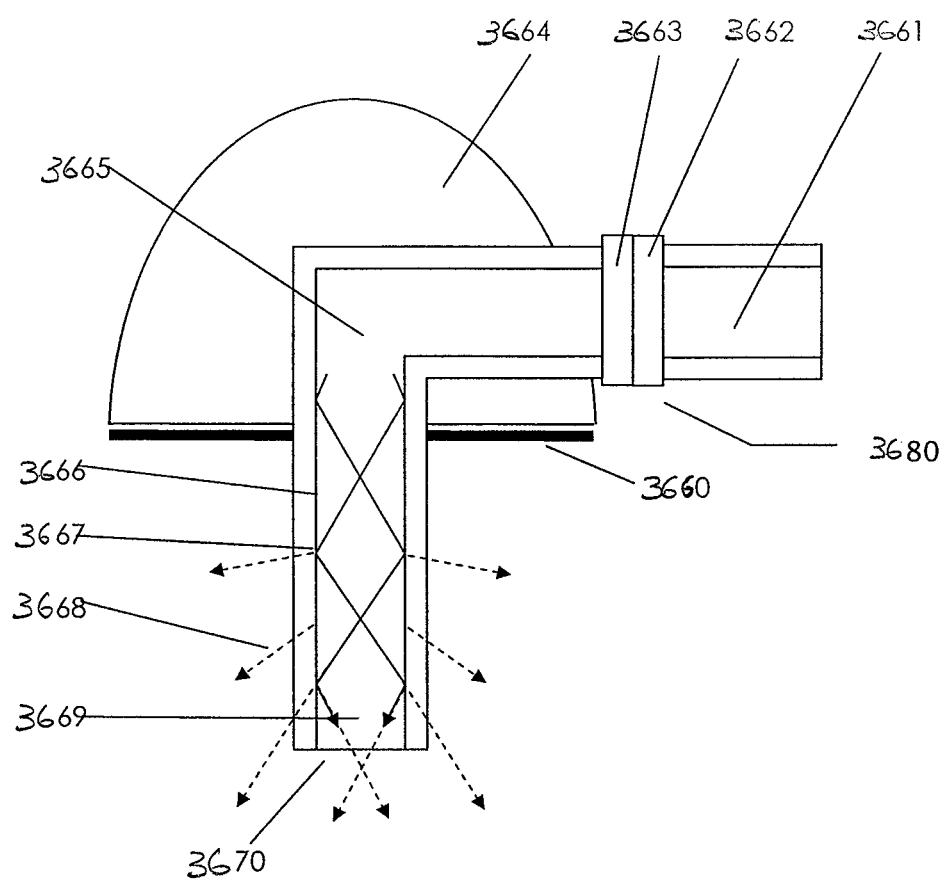
FIG. 36 schematically describes a catheter for drug delivery combined with a radiation source that guides the light through the catheter tube.

Any of the above mentioned configurations for coupling or decoupling (scattering) the light out of the catheter end can be used with all of the various locations of the light source as described in different herein. Referring to FIG. 36, showing another exemplary treatment device, light can be guided in the catheter tube 3670 such that radiation (e.g., light), represented schematically by the bouncing ray lines, propagates in the drug containing fluid 3669 and/or in the tube walls 3667 and/or in special layers or structures or waveguides inside the tube 3670 or the tube wall 3667, or in any combination thereof. The light can be guided until it reaches the catheter end where it is emitted out through the same opening from which the drug is delivered and infused into the body of the patient. As shown, the light is strongly scattered in the tissue and illuminates a region having an approximate spherical shape (not shown), with its center, for example, 0.5-1 mm beneath the catheter tip (not shown). In some embodiments, light is emitted from within catheter 3670, through, for example, a radiation source 3665.

Similarly to some of the other device implementation described herein with respect to the other figures, the device shown in FIG. 36 may include, for example, a catheter securing device 3664 with an adhesive layer 3660. Additionally, drug is delivered through a drug delivery tube 3661 from a drug delivery device (not shown) that an includes a connector 3680 with sections 3662 and 3663 (similar to the sections shown in FIG. 33).

In some embodiments, a larger illuminated area is used, for example, to reduce the light intensity or lumens per unit area, for example, for safety reasons. Therefore, in some embodiments, the light may be emitted through a larger portion of the catheter tube 3670. In some embodiments, the focused guidance of the light in the portion of tube 3670 within the tissue is reduced due, for example, to the contact of the catheter wall 3667 with the tissue or due to the fact that the waveguide layers and/or structures are altered to cause the light to leak out of the waveguide into the adjacent tissue. As previously explained, alteration of structure and/or material of the waveguide layers can be used to control the profile of the illumination of the radiation at the drug infused tissue area.

In addition to changing the properties of the layers and/or structures, additional refractive or diffractive elements can be added to the catheter tube end to better control the spatial and angular distribution of the light emitted from the catheter end. For example, the inner side 3666 of the catheter 3670 and/or the outer side of the catheter surface can be made rough or diffusive to scatter the emitted light 3668. The surface roughness of the catheter tube wall 3667 can be increased by, for example, embossing a pattern into the inner or outer sides. Such pattern embossing may be done during the catheter tube manufacturing process or at the end of the manufacturing process, for example, by pressing a patterned cylindrical mold within or on the tube 3670, with some heating that softens the tube polymer. In some embodiments, the light angular and spatial distribution can be shaped by embossing a diffractive optical element pattern into the inner or outer sides. Diffraction optical element patterns, such as a grating, may be used for coupling light into or out of optical waveguides. All or a portion of the light may be emitted out of the end of catheter tube 3670.

The device may provide illumination to the tissue both from inside the catheter and through the skin by a combination of the techniques, structures and arrangements described herein.

The devices described herein (according to some embodiments) may have short range RF or IR communication with a data management and control unit, such as a Personal Digital Assistant (PDA), a personal computer, a cellular telephone and/or to a dedicated device that supports managing the drug therapy. For example, if the drug is insulin, the data managing device may obtain the glucose readings from a glucose sensor, whether manually or automatically, or by reading glucose sensing strips. The device may also obtain information about consumed carbohydrates and other ingredients of food and/or drinks. The device may also store patient history and relevant parameters, such as weight, BMI, insulin resistance and so forth.

The data managing device may also calculate the optimal required amount of insulin and the optimal tissue radiation profile. This information can be sent wirelessly to the drug delivery pump and/or to the radiation device (for providing electromagnetic radiation), for optimal drug delivery. The radiation device may transmit tissue parameters measured by sensors disposed on it to the data management and control unit as additional information for determining one or more therapeutic parameters and/or for future statistics and data analysis. The data management and control unit may recommend an optimal drug dosage and optimal radiation profile to infused tissue region, which the patient (or other user) then approves before initiation of therapy. The data management and control unit may recommend an optimal drug dosage. In some embodiments, the data management and control unit may form part of the drug delivery pump.

Figure 37:
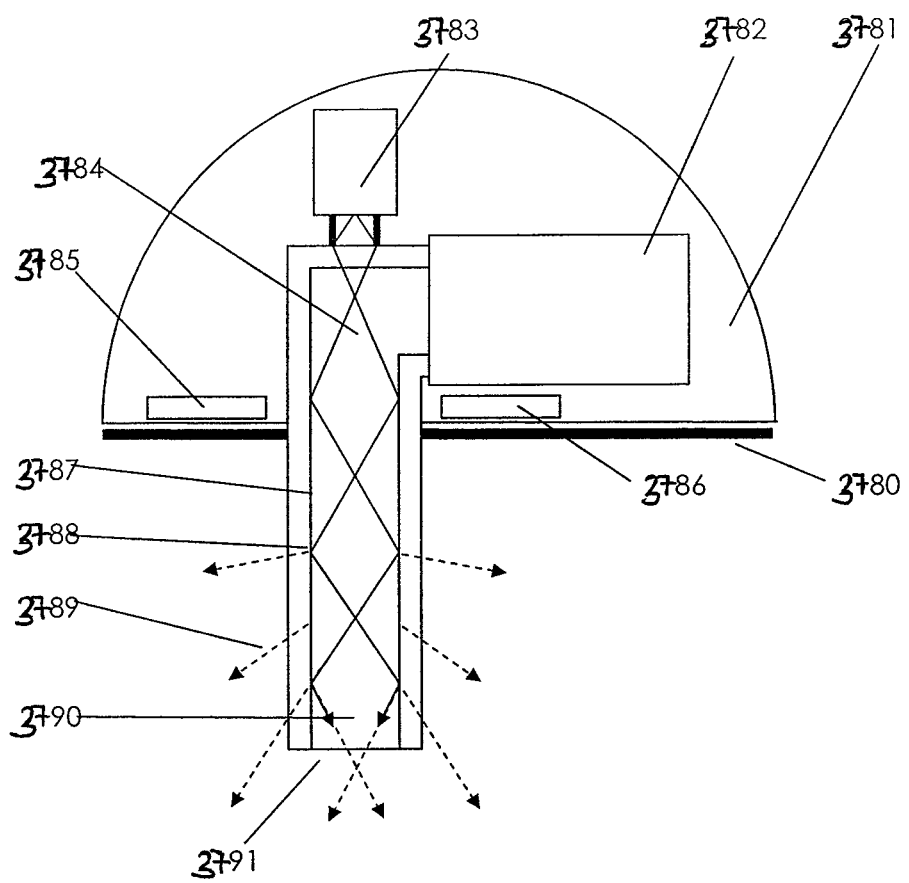
FIG. 37 schematically describes a catheter for drug delivery combined with a radiation source that guides the light through the catheter tube and with an optical sensor.

Referring to FIG. 37, another exemplary treatment device with optical sensors is shown. The treatment device includes, for example, two sensors 3785 and 3786 Fewer or additional sensors of different types may be used. As further shown, the device of FIG. 37 includes a disposable drug delivery pump configuration. In the depicted configuration, the drug delivery pump 3782 and at least one light source 3783 are disposed in a single housing 3781 attached to the skin with adhesive layer 3780.

A light source 3783 generates light to illuminate the tissue. The light is transferred to the tissue through catheter 3790 (the light is shown schematically by the bouncing ray line 3784). The two optical sensors 3785 and 3786 measure the light passing through the catheter 3790. Light is also reflected by a reflective coating for inner side 3787 of tube walls 3788, although some may also scatter to the outside 3789 of tube walls 3788.

The light exits at catheter tip 3791 into the tissue (not shown). The light is then scattered into and off the tissue and reaches the optical sensors 3785 and 3786 through windows in the adhesive layer 3780 or, if the adhesive layer is transparent, through the adhesive layer. Measurements performed by the optical sensors 3785 and 3786 are used to determine the amount of absorbed light (based on the fact that the initial power of the light source is known). If wavelengths strongly absorbed by the hemoglobin such those as in the range of 600-1000 nm are used, the optical sensors 3785 and 3786 can provide information related to the hemoglobin concentration at the adjacent tissue region, which may thus provide information on the local blood perfusion. The blood perfusion information can be used to monitor radiation level, distribution or wavelengths.

The absorbed light level can also be evaluated by measuring the light which is back scattered into the optical waveguide formed by the catheter tube 3790, guided by the waveguide and then coupled out of the waveguide using the same coupling optics previously described, or by using additional coupling optics into an optical sensor used for measuring the back scattered light (not shown).

The above described methods, apparatus and devices for radiating the tissue are not limited to drug-delivery pumps, but can also be used with manual delivery of the drug, such as connecting a syringe instead of a pump to the proximal part of the catheter. Under such circumstances, the catheter proximal part may terminate in a connector or a port that fits the syringe tip. The distal part of the catheter is inserted into the tissue as previously described in relation to the exemplary drug-delivery arrangements.

Although the catheter was drawn with a 90° penetration angle in the above embodiments, any suitable angle for catheter penetration may be selected. Smaller angles of penetration for the catheter may improve the attachment on one hand, but may also be more painful to insert.

It should be noted that whenever the local effect of the radiation or illumination of the tissue is described over the drug infused region, the radiation or illumination effect can also be applied to larger volume of tissue in the vicinity of the drug infused volume or to smaller volume of tissue, depending on the specific treatment.

It should be noted that whenever 'or' is used in this document the choice of the two or more detailed options is also possible. It should be understood that certain features as described herein, which are, for clarity, described in the context of separate embodiments, may also be provided in combination in a single embodiment. Conversely, various features which are, for brevity, described in the context of a single embodiment, may also be provided separately or in any suitable sub-combination.

Stimulated Drug Delivery Systems and Methods

In some embodiments, the present invention relates to devices for improving, modifying and/or stabilizing pharmacokinetic and/or pharmacodynamic profile of a drug infused into the tissue by a catheter and absorbed into the blood or lymphatic system. The devices described in some of the embodiments of the present application apply additional treatment or stimulation to the vicinity of the drug delivery site. The treatment can be one or combination of the tissue treatment treatments modalities described in U.S. Ser. No. 11/812,230, such as: heating, modifying temperature, massaging, mechanical vibration, acoustic vibration, ultrasound, suction, infusion of an additional substance or chemical, applying a low electric field, applying a low magnetic field, light irradiation, radiofrequency ("RF") irradiation, microwave ("MW") irradiation, etc. In some embodiments, the device has a catheter for insertion within the tissue to infuse a substance into the infused tissue region. The infused tissue region (i.e., the infused region) can be one of the skin layers or the subcutaneous tissue or deeper tissue elements within any organ or viscera.

In many instances, the patients require insulin delivery around the clock to keep proper levels of glucose in their blood. Insulin can be delivered at a basal rate or in bolus doses. The basal rate represents insulin that is continuously delivered to the patient yet in practicality is delivered in small intermittent boluses. Such continuous delivery of insulin keeps the patient's blood glucose in the desired range between meals and over night. In many cases the basal insulin is delivered by insulin pumps in short infusion pulses every 1-5 minutes. In some embodiments, tissue or skin treatments or stimulation methods can be used to treat or stimulate a tissue region to which insulin is infused during basal insulin delivery. One possible effect of the tissue treatment, such as regulating the infused tissue region vicinity to a known temperature, is improving the stability of the insulin absorption to the circulatory system, and consequently improving the basal insulin pharmacokinetics pharmacodynamics stability. Another possible effect of such a treatment is improving the efficiency of the absorption of the insulin and consequently reducing the amount of infused insulin needed to achieve the desired metabolic effect.

In addition the diabetic patient needs to infuse insulin bolus doses for matching a the carbohydrates consumed during meals. When a patient consumes food, his or her levels of glucose rise and the insulin bolus dose is supposed to match the rise in the level of glucose and to prevent large glucose excursions. However, many conventional subcutaneous drug delivery systems are incapable of quickly matching or preventing the rise of blood glucose known as post prandial hyperglycemia. The delay in such matching is also true in case of the "rapid-acting" insulin analogs. Some of the reasons for this delay include a lag in the absorption of insulin from the injection site and the time it takes for complex insulin molecules to break down into monomers.

It is well known in the art that there are some adverse effects for infusing large amounts of insulin which beside of regulating the glucose absorption has several additional hormonal effects, such as being growth factor. In some cases, the excess amounts of insulin cause indirectly an undesired weight gain of diabetic patients, specifically those with a tendency for developing hypoglycemia. In some cases the excess amounts of insulin at the infusion sight cause undesired local lipo-hypertrophy.

In some embodiments, tissue or skin treatments or stimulation methods can be used to treat or stimulate a tissue region to which insulin is infused during basal or bolus insulin delivery. One possible effect of the tissue treatment is improving the efficiency of the absorption of the insulin into the blood or lymph systems and consequently reducing the amount of the insulin needed to create the desired metabolic effect. Consequently the undesired adverse effects of the excess insulin levels, such as excess weight gaining can be reduced. Another possible effect of the tissue treatment is improving and reducing the amounts and the durations that the insulin lasts at the tissue infused region, since it is absorbed faster in the blood or lymph systems. Consequently the undesired local adverse effects of the excess insulin levels, such as the lipo-hypertrophy or local irritation can be reduced. Another possible effect of the infused tissue region vicinity treatment is improving the local blood perfusion, which reduces the local inflammation effects of the infusion set or the puncturing or the insulin. Another possible effect of reducing the short and long term local effects of the insulin on the insulin infused tissue region is to lengthen the duration of using an infusion set on the same sight.

In some embodiments, tissue or skin treatment methods can be activated on elective or preprogrammed boluses for brief periods to provide a boost of the insulin absorption. In some embodiments, tissue or skin treatments methods can be a part of all or some of the elements of complex pre programmed boluses such as split wave, square root and other bolus patterns. The stimulation can be activated for the initial phase of a standard bolus, specifically for pre-programmed components of a split bolus or at intervals of interest of the square bolus. In other embodiments—the stimulation can be activated by a pre-programmed duty cycle independent of the bolus type. In other embodiments, the intermittent activation can be synchronized with individual bolus components of the basal rate.

In some embodiments, tissue or skin treatments or stimulation methods can be used to treat or stimulate a tissue region to which a drug is infused by an implanted drug or substance delivery device. In some embodiments, tissue or skin treatments or stimulation methods can be used to treat or stimulate a tissue region to which insulin is infused by an implanted insulin delivery device. In some embodiments, implanted insulin delivery device is an implanted insulin pump. In some embodiments, implanted insulin delivery device are implanted beta cells that can produce insulin. In case of implanted beta cells said tissue treatment can support also the implanted cells, for instance by improving local perfusion and improving the cells oxygen, glucose and other required ingredients supply. By improving the local perfusion also the beta cells or other glucose sensing element can react without unwanted delays to fast glucose variations.

Figure 38:
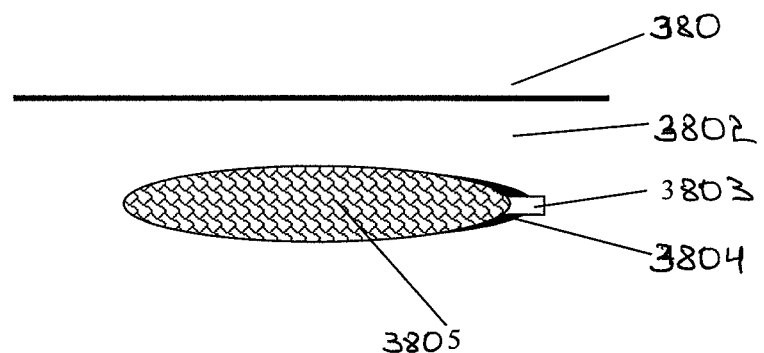
FIG. 38 illustrates an exemplary implanted drug delivery device combined with a heating element, according to some embodiments of the present invention.

In some embodiments, of implanted drug delivery device the tissue treatment can be applied by the implanted device. An example is illustrated in FIG. 38. The implanted drug delivery device 3805 is implanted in a tissue region 3802 underneath the skin 3801. The implanted drug delivery device has a catheter schematically shown by 3803 for infusion of the drug into the tissue. In some embodiments, the drug infusion to the tissue can be done using other modalities instead of a catheter, such as, few catheters, or a large opening with a membrane on the drug delivery device side for infusing the drug into a larger volume of tissue and improving the drug absorption into the circulatory or lymph system. The implanted drug delivery device has a treatment element, schematically shown by 3804 for applying treatment to the drug infused region vicinity. The treatment can be one or combination of the tissue treatment treatments modalities, such as: heating, modifying temperature, massaging, mechanical vibration, acoustic vibration, ultrasound, suction, infusion of an additional substance or chemical, applying a low electric field, applying a low magnetic field, light irradiation, radiofrequency ("RF") irradiation, microwave ("MW") irradiation, etc.

Figure 39:
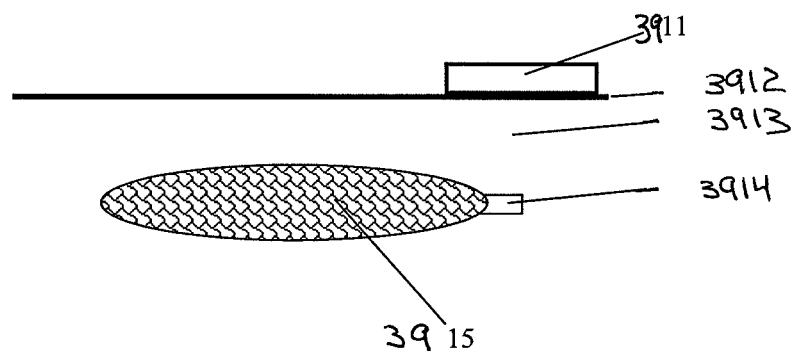
FIG. 39 illustrates an exemplary implanted drug delivery device combined with a heating element attached to the skin above the drug infused region, according to some embodiments of the present invention.

In some embodiments, of implanted drug delivery device the tissue treatment can be applied by a treatment device attached to the skin. An example is illustrated in FIG. 39. The implanted drug delivery device 3915 is implanted in a tissue region 3913 underneath the skin 3912. The implanted drug delivery device has a catheter schematically shown by 3914 for infusion of the drug into the tissue. In some embodiments, the drug infusion to the tissue can be done using other modalities instead of a catheter, such as, few catheters, or a large opening with a membrane on the drug delivery device side for infusing the drug into a larger volume of tissue and improving the drug absorption into the circulatory or lymph system. The treatment device, schematically shown by 3911 is attached to the skin above the drug infused region for applying treatment to the drug infused region vicinity. The treatment can be one or combination of the tissue treatment treatments modalities, such as: heating, modifying temperature, massaging, mechanical vibration, acoustic vibration, ultrasound, suction, infusion of an additional substance or chemical, applying a low electric field, applying a low magnetic field, light irradiation, radiofrequency ("RF") irradiation, microwave ("MW") irradiation, etc. The treatment device 3911, can be attached to the skin in many methods, as described in application U.S. patent application Ser. No. 11/812,230, such as adhesive layer.

In some embodiments, glucose level regulation is obtained by automatically controlling the insulin infusion rate using a continuous glucose sensor and a control algorithm. There are many attempts to compose such an "artificial pancreas" since the development of continuous glucose monitors. In this case, any delay such as the current delays of the insulin absorption and action time, any variability in this delay and any variability in the residual insulin level in the body induces an error for the control algorithm that will result in less tight glucose regulation. Thus, by stimulating or applying a treatment to the vicinity of the infused tissue region combined with input from an implanted or other types of glucose sensor and a control algorithm can provide better accuracy and robustness of a closed loop glucose level control systems.

In some embodiments, the tissue in the vicinity of the glucose sensor is treated or stimulated by the above described treatments to improve the glucose transport form the blood system to the interstitial fluid and into the glucose sensor, as described in U.S. provisional application 60/948,472.

In some embodiments, the above described treatment or treatments combination is applied to the insulin infused tissue region vicinity and the same or a different treatment or treatments combination is applied to the vicinity of the tissue region in which the glucose level is measured by the glucose sensor. Therefore, both the delay of the glucose transport to the ISF and to the sensor and the delay of the insulin pharmacokinetics and pharmacodynamics are reduced, enabling to achieve a more tight glucose regulation by closing the loop between the two devices.

In some embodiments, the same treatment or treatments combination is applied to the insulin infused tissue region vicinity and to the vicinity of the tissue region in which the glucose level is measured by the glucose sensor.

In some embodiments, the tissue region in which the glucose level is measured by the glucose sensor is the in the vicinity of the insulin infused tissue region and the treatment or treatments combination is applied to the vicinity of that tissue region with a single treatment element.

In some embodiments, described above both the insulin delivery device and the glucose sensor are implanted. In others, both are part of the same transcutaneous catheter or part of a device that has more than one catheter (one for infusion and one as a sensor) that are both inserted by one insertion process and are located in the proximity of each other.

In some embodiments, for automatic regulation of the glucose level described above, the processing unit or the algorithm includes an automatic meal detection algorithm that identifies a rapid rise in the glucose level on a continuous glucose level signal. The processing unit infuses insulin bolus using the insulin delivery device and applies the above described treatment or treatments in case of detection of a meal and automatic detection. In others, the indication of food consumption can be given manually by the patient through the infusion pump.

In some embodiments, for semi automatic regulation of the glucose level that involves human approval for insulin bolus, the processing unit or the algorithm includes an automatic meal detection algorithm that identifies a rapid rise in the glucose level on a continuous glucose level signal. The processing unit alerts the patient that infuses an insulin bolus using the insulin delivery device and applies the above described treatment or treatments to shorten the insulin action time and reduce the postprandial glucose excursion.

In some embodiments, the treatment can be programmed to reduce the temperature in order to reduce absorption of previously administered insulin that is still in the subcutaneous space. This feature can be a cautionary and protective element of a closed loop system.

In some embodiments, the treatment can be in the vicinity of the drug infused tissue region and still induce the desired effect to the drug infused tissue region. For instance in the case of heating, W. Magerl et. al. [W. Magerl et. al. Journal of Physiology 497.3 pp 837-848 (1996)] showed that heating the skin can induce vasodilatation in human at a distance of even 30 mm due to activation of nociceptive axon reflex. They also showed that in some cases short period heating can also evoke vasodilatation for a period of few minutes. Therefore In some embodiments, the treatment, such as heating to temperature of 39.5° C. is applied for short periods of 2-60 seconds every few minutes and evokes vasodilatation that improves the drug pharmacokinetics and/or pharmacodynamics in the drug infused tissue region.

In some embodiments, the treatment can be calibrated for each patient to optimize it for its own nociceptive axon reflex activation threshold. For instance, W. Margerl et. al. show that the vasodilatation evoking temperature after 64 seconds of heating can vary between 37-43° C. for different subjects. The calibration can be done also locally for a specific infusion site. An method for calibrating the treatment device is to start applying the tissue treatment gradually in the first initiation of the treatment device and measure the treatment effect on the tissue, such as vasodilatation, using a specific sensor connected to the processor unit that controls the treatment device. Than the processing unit decide what level of tissue treatment to apply, to optimize the treatment effect on one hand without causing any adverse effects on the other hand. For example, in case the tissue treatment is heating and the desired effect is vasodilatation, the treatment device can gradually heat the tissue till the safety upper limit and measure the local tissue vasodilatation. The vasodilatation can be measured by Laser Doppler Flowmetry (LDF). Another close parameter that can be measured is the tissue blood perfusion which can be measured by LDF or by one of the known in the art measurements for the tissue optical absorption in hemoglobin significant absorption lines, such as 700-1000 nm. Afterwards, the processing unit uses that information to decide what the best peak temperature of the temperature heating profile to which the specific sight at the specific subject should be heated should be.

In some embodiments, these calibration process is repeated once a while, such as every 6-12 hours, to compensate for changes that might influence on the temperature threshold of the axon reflex response to local heating.

In some embodiments, these calibration process is repeated every time the treatment device is operated, such as during insulin bolus to compensate for more rapid changes that might influence on the temperature threshold of the axon reflex response to local heating, such as Nitric Oxide, noradrenaline and other substances [Belinda et. al. J. Physiol. 572 3 pp 821-820 (1996)]. In this case when the treatment, such as heating, is started the treatment parameter, such as temperature, is raised gradually while measuring the desired tissue parameter such as vasodilatation, using LDF. When the vasodilatations happens the treatment level, such as temperature, is stabilized to that level or slightly above it.

In some embodiments, these calibration process is repeated also during the treatment. In this case the treatment, such as heating, after it starts as described in the paragraph above is regulated to keep the desired tissue parameter, such as vasodilatation level stabilized to a target level, during the whole treatment. Stabilizing the desired tissue parameter, such as vasodilatation level, stabilizes also the absorption of drug in the blood and improve the repeatability of the drug pharmacokinetics and pharmacodynamics. Controlling the treatment level according to the desired tissue parameter, such as vasodilatation level may reduce also the power consumption of the treatment device. For instance, in case of heating, since short period heating to a certain temperature above the threshold temperature initiates the axon reflex response and vasodilatation, there is no need to keep the temperature high for a long period and by that the power consumption can be reduced.

Systems and Methods for Drug Delivery Using Implanted Neural Stimulation

Figure 40A:
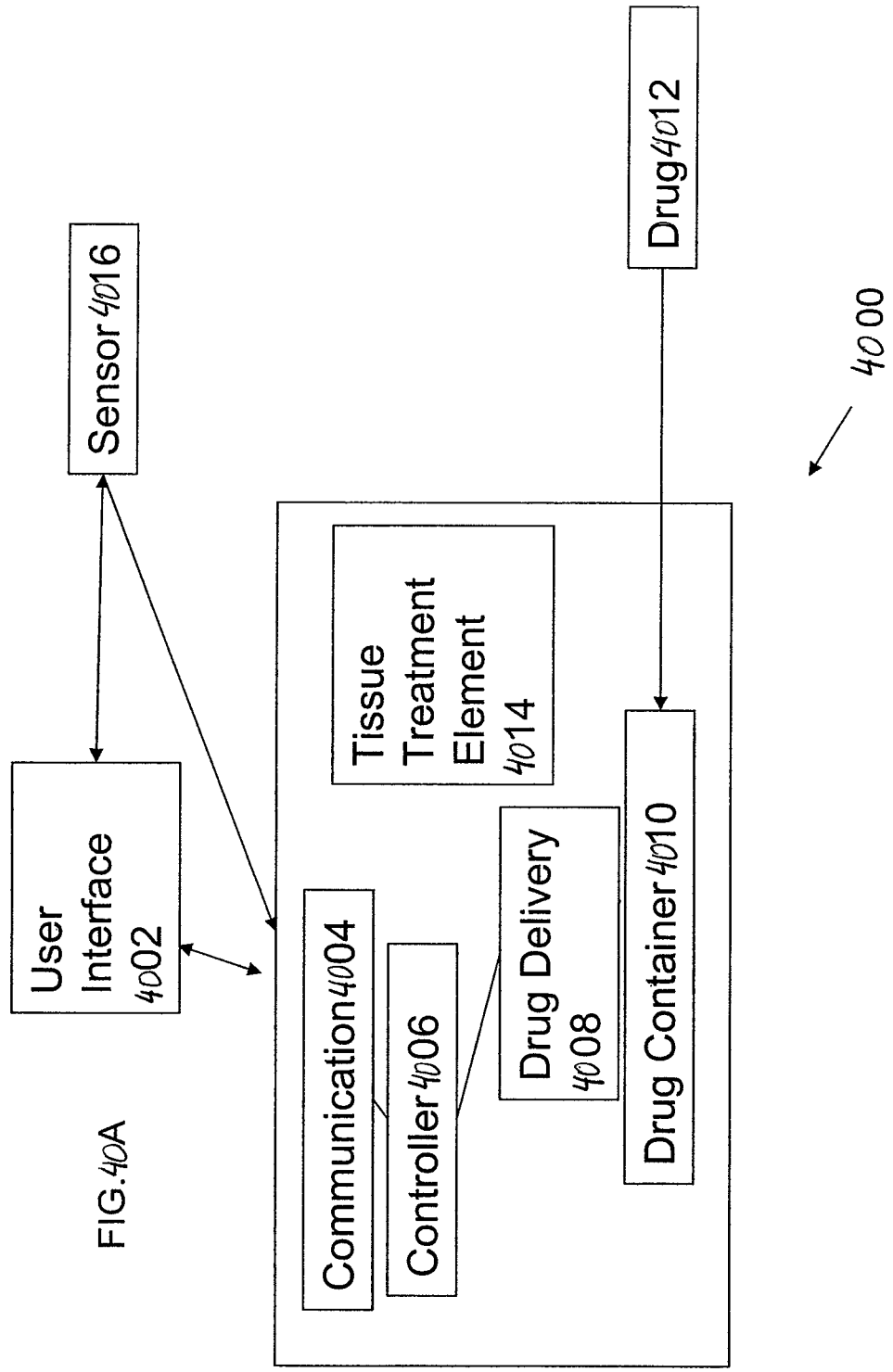
FIGS. 40A-D are schematic block diagrams of embodiments of the implanted drug delivery device according to the present invention.
Figure 40B:
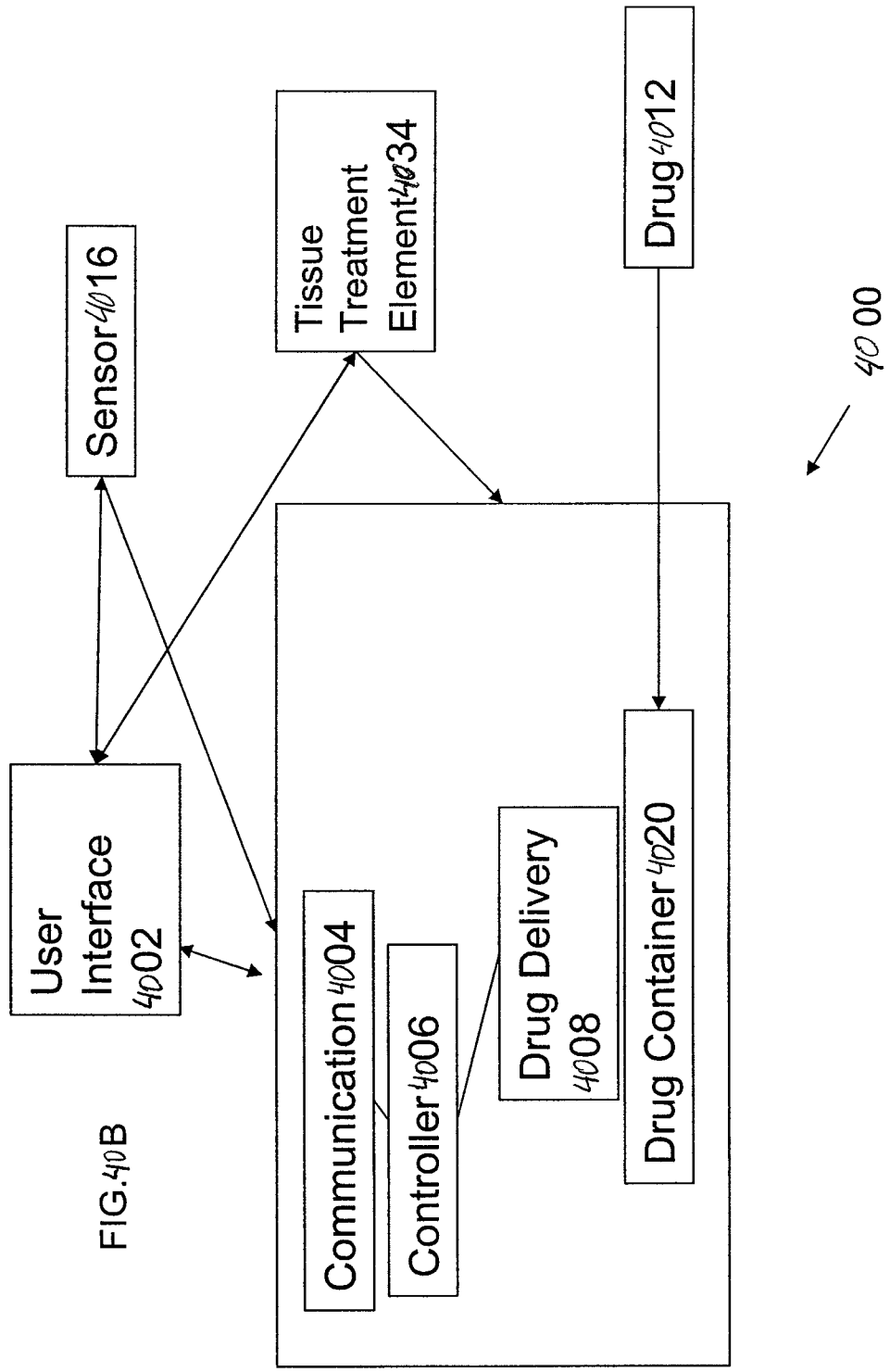
Figure 40C:
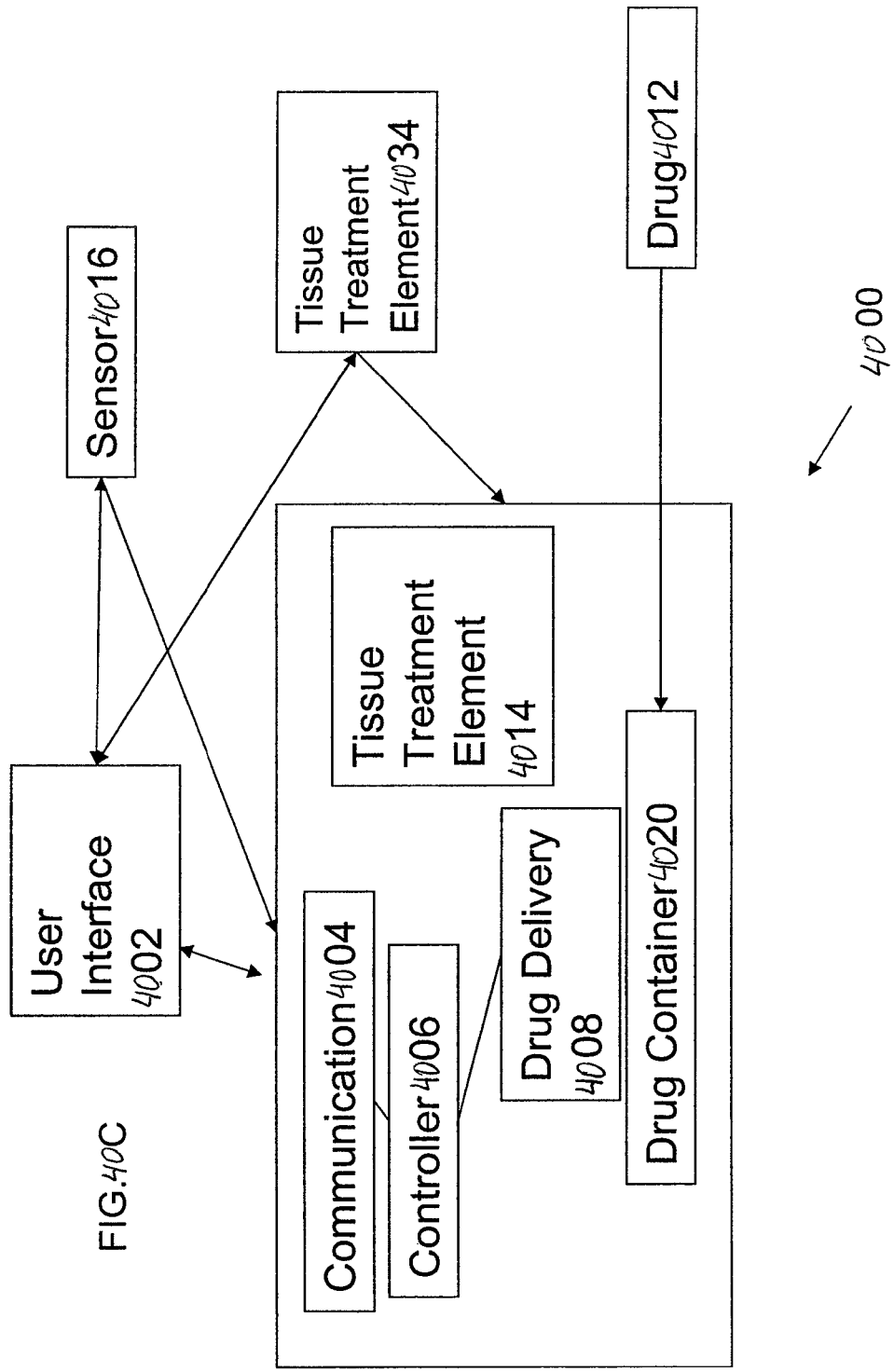

Referring now to the drawings, FIG. 40A-C use similar labels to refer to the same functioning elements. FIG. 40A is a schematic block diagram of an drug delivery device 4000 according to the present invention for controlled drug delivery to a target tissue. Drug delivery device 4000 includes user interface 4002, communication module 4004, controller 4006, drug delivery module 4008, drug compartment 4010, tissue treatment element 4014, external drug supply 4012, and sensor 4016. Device 4000 is implanted within the body and provides an improved controllable drug delivery system. The implantation site may vary and is chosen depending on the target tissue and the drug being delivered. For example, device 4000 may be implanted subcutaneously or near the digestive tract for an insulin drug delivery system. However, if device 4000 includes a drug for the cardiovascular system, device 4000 may, for example, be implanted in a subcutaneous cavity in the vicinity of the cardiovascular system.

Sensor 4016 may not be implanted and is an independent external device, as is known and accepted in the art, that is used to monitor a measurand relative to the drug being delivered, for example including but not limited to a glucose sensor that indicates the glucose levels at the time of the test. At least one or more sensors may be used to measure a plurality of parameters relating to the drug being delivered. The measurements sensed by sensor 4016 are relayed to controller 4006, through user interface 4002 and communication module 4004 (for example). The controller 4006 depicts the action to be taken relative to the sensed results; the action to be taken may be the absence of an action. User interface 4002 may communicate instructions and protocols to controller 4006 using the communication module 4004. Controller 4006 may intrinsically include various treatment protocols, and historical data relative to the different situation sensed by at least one or more sensor 4016. Controller 4006 may employ learning algorithms, for example including but not limited to artificial intelligence means to adjust or adapt the treatment protocols to be more specific or tailored to the drug delivery needs and eating habits of the patient using device 4000.

Controller 4006 controls and overseas the performance of the drug delivery module 4008 and tissue treatment element 4014 with respect to the parameters sensed by at least one or more sensor 4016. Drug delivery module 4008 may include at least one or more catheters that is/are used to deliver the drug to the targeted site. The drug delivery may be undertaken with a selective membrane that allows the drug to be safely delivered to the target tissue over a larger surface area.

Drug delivery to the target tissue is mediated by controller 4006 that uses the drug storage compartment 4010 to delivery the drug via drug delivery module 4008. Drug storage compartment 4010 contains sufficient quantities of the drug to last a prolonged period of time, for example several months. When drug quantities are depleted and need to be replenished, controller 4006 may communicates via communication module 4004 to user interface 4002 regarding the need for replenishment. The drug supply may be replenished from an external source 4012 that is directly linked to the implanted drug storage container 4010. The link between drug storage 4010 and drug source 4012 may, for example, be mediated by a mechanism including but not limited to one or more of a reusable catheter, an injection, or the like.

Tissue treatment element 4014 is used to stimulate or inhibit the tissue targeted site to increase drug absorption, more by increasing vasodilatation, or by employing a mechanism to improve drug uptake that is specific to the drug being delivered and the target site itself. Tissue treatment element 4014 may be used on the drug itself, providing further control where drug properties are changed to increase or decrease its relative activity. Tissue treatment element 4014 may be stimulated by modes including but not limited to one or more of temperature change, optical, IR irradiation, RF irradiation, microwave irradiation, ultrasound, massaging, or the like. Tissue treatment element 4014 may stabilize the tissue targeted site to reduce the variability of the drug absorption into the circulatory system.

Controller 4006 may include a database (not shown) that contains various treatment protocols specific to one or more different metabolic parameters that are sensed by sensor 4016. Changes, updates to the database, and/or treatment protocols within controller 4006, may be introduced from external resources through communication module 4004. Communication module 4004 may be able to both send and receive updates to and from an external user interface 4002 or like source, for example including but not limited to a PDA, computer, server, cellular telephone or the like. Communication with communication module 4004 may be mediated by communication protocols for example including but not limited to cellular, wireless, optical, IR (infrared), RF (radiofrequency), or the like communication protocols; communication protocols used may be encrypted.

FIG. 40B is an embodiment of the drug delivery device according to the present invention that functions similarly to that depicted in FIG. 40A, however, the tissue treatment element 4034 is not implanted but rather is employed at or on the external skin surface. Treatment element 4034 may be adhered to the skin and functions externally.

Tissue treatment element 4034 is used to indirectly stimulate or inhibit the tissue targeted site by applying an appropriate treatment on the external surface. The employed treatment protocol controls drug absorption, more by controlling vasodilatation, or by employing a mechanism to improve drug uptake that is specific to the drug being delivered and the target site itself. Tissue treatment element 4034 may function by different modes including but not limited to one or more of temperature change, optical, IR irradiation, RF irradiation, microwave irradiation, ultrasound, massaging, or the like. Tissue treatment element 4034 may stabilize the tissue targeted site to reduce the variability of the drug absorption into the circulatory system.

FIG. 40C depicts another embodiment of the drug delivery system according to the present invention wherein a plurality of tissue treatment elements are employed, wherein at least one or more elements include one or more implanted tissue treatment elements 4014 and at least one or more elements include one or more external tissue treatment elements 4034. The implanted and nonimplanted treatment elements 4014 and 4034 combination provides further control of the applied treatment directly or indirectly to the target tissue site.

Figure 40D:
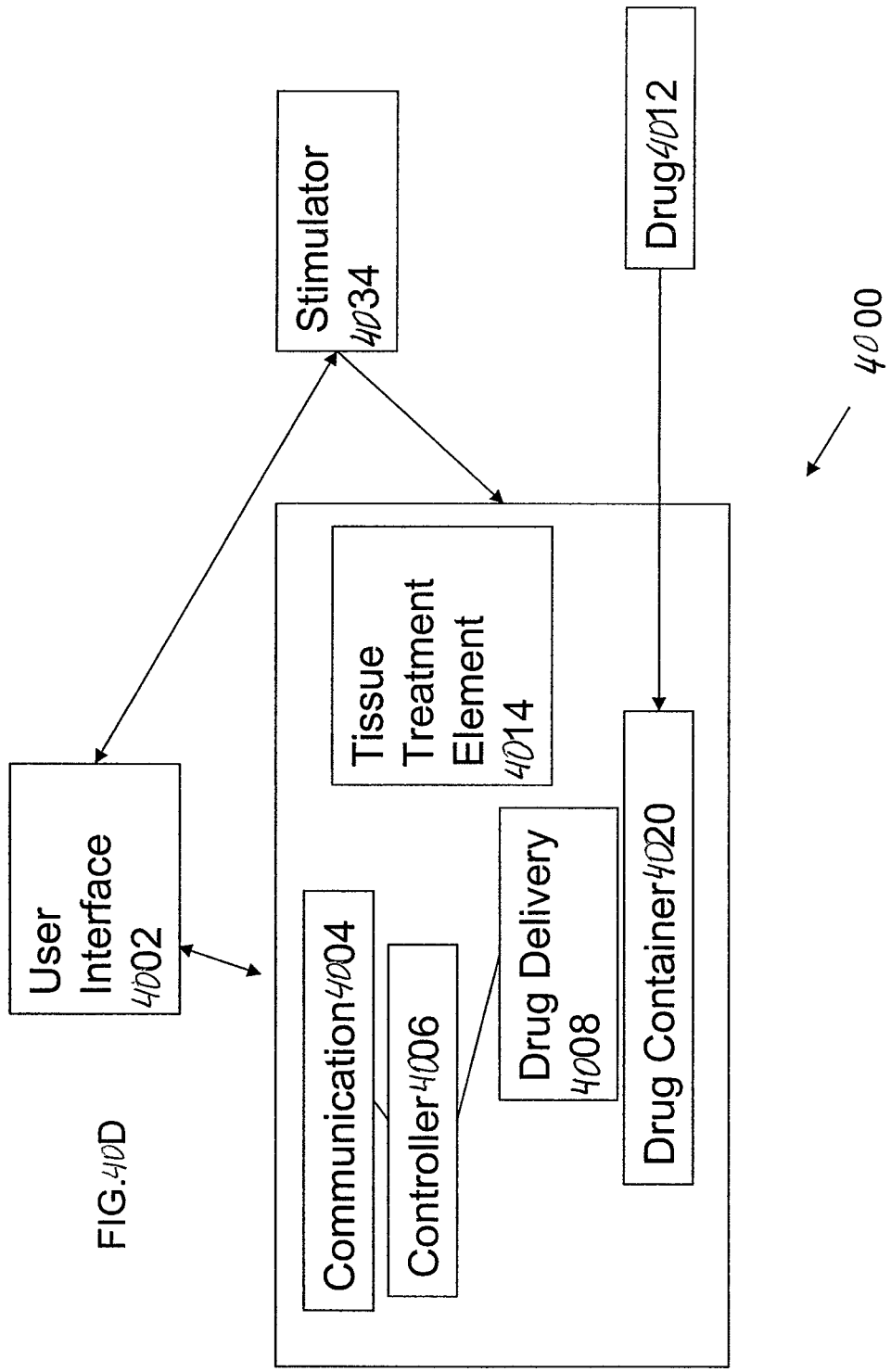

FIG. 40D depicts another embodiment of the drug delivery system according FIG. 40A wherein a sensor is not utilized. Drug delivery system 4000 delivers the appropriate medicament to the tissue target site independent of sensed information; rather, delivery system 4000 functions according to data obtained from user interface 4002 and/or by operation of controller 4006. In this embodiment, drug delivery module 4008 functions based on the schedule or protocols provided by controller 4006 and/or indirectly from user interface 4002, as described in FIGS. 40A-C. Similarly, neither of the implanted tissue treatment element 4014 or external issue treatment element 4034 (shown as stimulator 4034) function based on sensed information; rather both function according to one or more protocols obtained from either user interface 4002 or controller 4006.

FIG. 41A is a depiction of an embodiment of the present invention according to FIG. 40A where the tissue treatment element 4112 is implanted and located internally to skin 4111. Tissue treatment element 4112 is used to treat the tissue layer to improve the pharmacokinetic and/or pharmacodynamic properties of the targeted tissue. In some embodiments, drug storage compartment 4108 provides the drug to be delivered to the delivery module 4106 and thence to delivery member 4120. In some embodiments, for example for tissue treatment that involves direct or indirect heating and temperature sensitive drugs, such as insulin, where some types of insulin are preferred to be stored at less than 37° C., the drug storage compartment 4108 is thermally isolated, to keep the drug at the proper temperature during the tissue treatment. The drug may be delivered to the storage compartment 4108 by direct injection through membrane 4104. Tissue stimulation protocols and drug delivery protocols may be communicated to the controller (not shown) via user interface 4116.

FIG. 41B is a depiction of an embodiment of the present invention according to FIG. 40B where the tissue treatment element 4102 is located externally to skin 4111 and is not implanted. Tissue treatment element 4102 may be attached to the skin via an adhesive layer and/or a strap (not shown). Tissue treatment element 4102 is used to treat the tissue layer to improve the pharmacokinetic and/or pharmacodynamic properties of the targeted tissue. Drug storage compartment

4108 may provide the drug to be delivered to the delivery module 4106 and thence to delivery member 4120. In some embodiments, for example for tissue treatment that involves direct or indirect heating and temperature sensitive drugs, such as insulin as noted above, the drug storage compartment 4108 is thermally isolated, to keep the drug at the proper temperature during the tissue treatment. Drug may be delivered to the storage compartment 4108 by direct injection through membrane 4104.

FIG. 41C is a depiction of an embodiment of the present invention wherein the drug is produced externally and introduced to the implanted portion via drug transfer catheter 4114. Tissue treatment element 4102 may be located externally to skin 4111. Tissue treatment element 4102 may be attached to the skin via an adhesive layer (not shown). Tissue treatment element 4102 is used to stimulate or inhibit the tissue layer to improve the pharmacokinetic and/or pharmacodynamic properties of the targeted tissue. In some embodiments, as noted above for tissue treatment that involves direct or indirect heating and temperature sensitive drugs, such as insulin, the drug storage compartment 4108 is thermally isolated, to keep the drug at the proper temperature during the tissue treatment. Catheter 4114 may be used to fill drug storage compartment 4108 in an implanted layer 4113 once replenishment is needed as determined by the controller (not shown). An indication of drug levels within compartment 4108 may be provided by controller (not shown) to a visual cue 4116 for example including but not limited to a user interface or LED. The drug is delivered through delivery member 4120 as shown.

FIG. 41D is a depiction of an embodiment of the present invention according to FIGS. 40D and 40C where there may be a plurality of tissue treatment elements, an external element 4102 located externally to skin 4111 and an implanted element 4112 located in the implanted layer 4113. Tissue treatment element 4102 may be attached to the skin 4111 via an adhesive layer (not shown). Tissue treatment elements 4102 and 4112 are used to treat the tissue layer to improve the pharmacokinetic and/or pharmacodynamic properties of the targeted tissue. In some embodiments, for example as noted above for tissue treatment that involves direct or indirect heating and temperature sensitive drugs, such as insulin, the drug storage compartment 4108 is thermally isolated, to keep the drug at the proper temperature during the tissue treatment. Drug storage compartment 4108 may provide the drug to be delivered to the delivery module 4106 and thence to delivery member 4120 that may be a membrane able to deliver drug over a larger surface area. The drug may be delivered to the storage compartment 4108 by direct injection through receiving membrane 4104.

Figure 42:
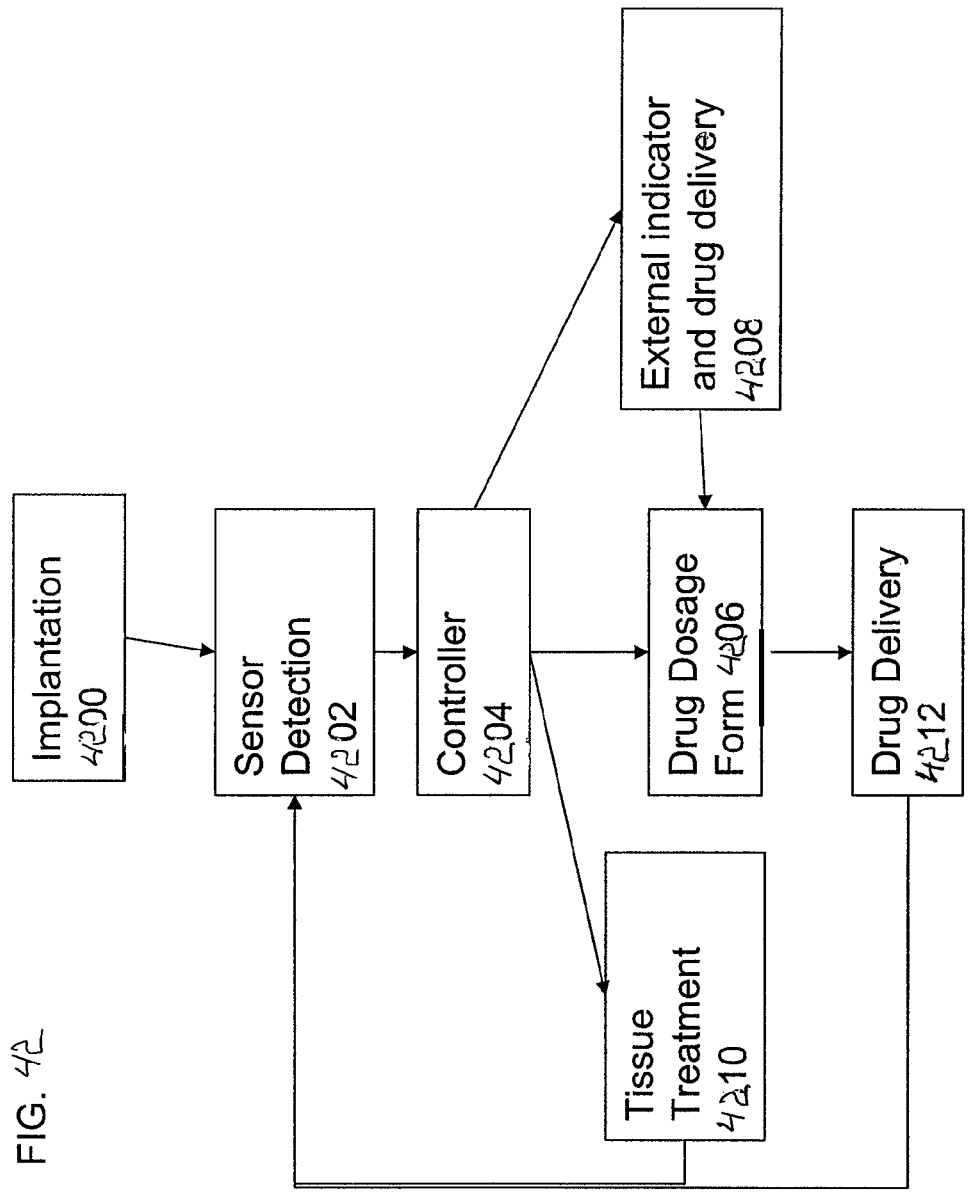
FIG. 42 is a flow chart of another exemplary method according to present invention.

FIG. 42 is a flow chart of the closed loop drug delivery device having and internal drug reservoir. The drug reservoir can be replenished using an external drug source as needed. In stage 4200 the device is implanted in a patient (subject) at a chosen tissue target site. In stage 4202 at least one or more sensors detect cellular and/or biological parameters, for example including but not limited to glucose levels. In stage 4204 the controller determines the action to be taken based on the sensor data obtained in stage 4202. In stage 4210 the controller may activate a tissue treatment element to initiate a stimulation or inhibition procedure using any one of its modes for example including but not limited to heat, cold, temperature change, ultrasound, optical, massage, physical stimulation, vibration, suction, IR, microwave, RF, optical, or the like. This stage may also include the absence of action. In some embodiments, stimulation is and optimized according to the user's own nociceptive axon reflex activation threshold.

In stage 4208 the controller may indicate that the drug supply is depleted and that drug replenishment is required, to an external indicator. The indication may be accomplished via an user interface, LED or the like. In stage 4206, a drug dosage form is determined and defined to be delivered to the tissue target site in stage 4212. Stages 4202, 4210 and 4212 are in a feedback loop that may continuously control the drug delivery process, or at least may be performed with a plurality of repetitions, in order to safeguard that the desired or appropriate drug levels are maintained at the target site.

Figure 43A:
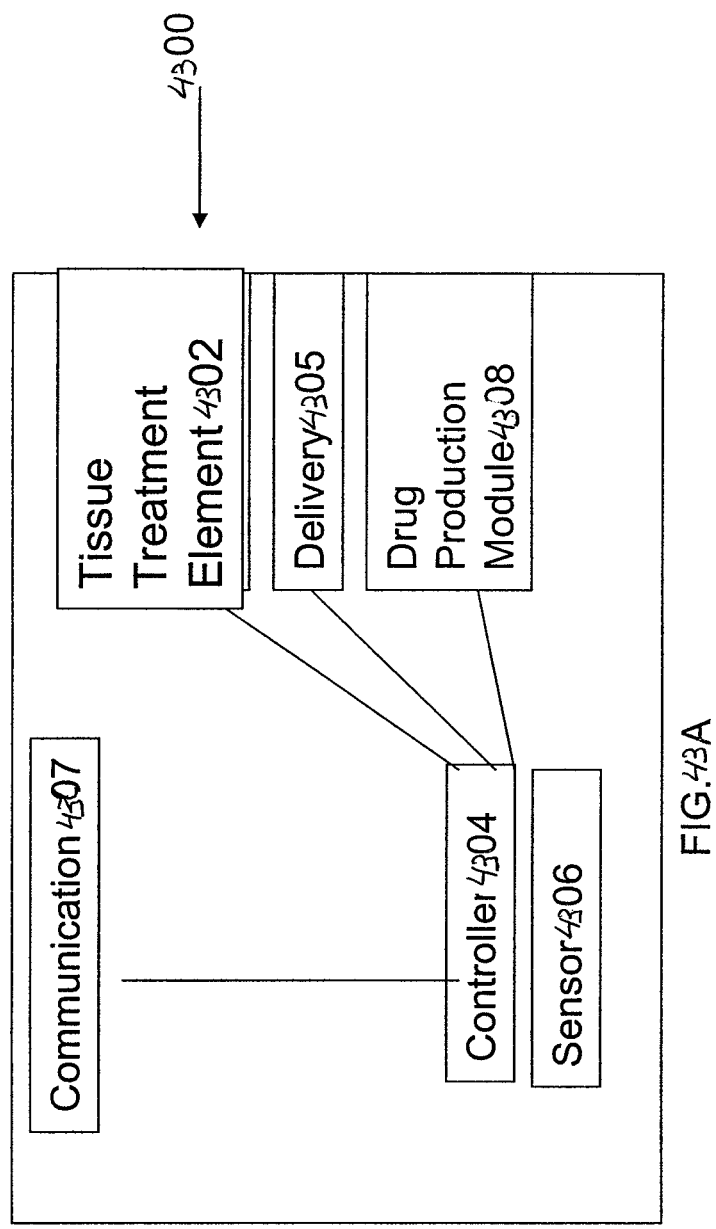
FIG. 43A is a schematic block diagram of an exemplary embodiment of the implanted drug delivery device according to the present invention.

FIG. 43A is a schematic block diagram of a drug delivery device 4300 according to the present invention for controlled drug delivery to a target tissue. Drug delivery device 4300 includes tissue treatment element or tissue treatment element 4302 (shown as stimulator 4302), controller 4304, sensor 4306, drug production module 4308, drug delivery module 4305 and communication module 4307. Device 4300 is implanted within the body and provides a closed loop drug delivery system. The implantation site may vary and is chosen dependent on the target tissue and the drug being delivered. For example, a device 4300 may be implanted subcutaneously or near the digestive tract for an insulin drug delivery system. However, if device 4300 included a drug for the cardiovascular system it may for example be implanted in a subcutaneous cavity in the vicinity of the cardiovascular system.

Sensor 4306 continuously or at least repeatedly and/or periodically monitors a measurand relative to the drug being delivered, for example including but not limited to a continuous glucose sensor that indicates the glucose levels at any given moment. At least one or more sensors may be used in conjunction to measure a plurality of parameters relating to the drug being delivered. The measurements sensed by sensor 4306 are relayed to controller 4304 that depicts the action to be taken relative to the sensed results; the action to be taken may be the absence of an action. Controller 4304 may include various treatment protocols, and historical data relative to the different situation sensed by at least one or more sensors 4306. Controller 4304 may also employ learning algorithms, for example including but not limited to artificial intelligence means to adjust or adapt the treatment protocols to be more specific or tailored to the drug delivery needs and eating habits of the patient using device 4300.

Controller 4304 controls and overseas the performance of the drug production module 4308, drug delivery module 4305 and tissue treatment element 4302 with respect to the metabolic parameters sensed by at least one or more sensors 4306. Drug delivery module 4305 may include at least one or more catheters that is/are used to deliver the drug to the targeted site. The drug delivery may be undertaken with a selective membrane that allows the drug to be safely delivered to the target tissue.

Tissue treatment element 4302 is used to stimulate or inhibit the tissue targeted site to increase drug absorption, more by increasing vasodilatation, or by employing means to improve drug uptake that is specific to the drug being delivered and the target site itself. Tissue treatment element 4302 may be used on the drug itself, providing further control where drug properties are changed to increase or decrease its relative activity. Tissue treatment element 4302 stimulates by modes including but not limited to temperature change, optical, IR irradiation, RF irradiation, microwave irradiation, ultrasound, massaging, or the like. Tissue treatment element or tissue treatment element 4302 stabilizes the tissue targeted site to reduce the variability of the drug absorption into the circulatory system.

Drug production module 4308 includes cells that may produce the drug, for example including but not limited to insulin that is to be delivered to a target site. Drug production module 4308 includes at least one or more beta cells, other cells, tissue culture and/or bacterial culture capable of producing insulin. Drug production by module 4308 is controlled by controller 4304.

Controller 4304 includes a database (not shown) that contains various treatment protocols specific to different metabolic parameters sensed by delivery device 4300. Changes, updates to the database, and/or treatment protocols within controller 4304 may be introduced from external resources through communication module 4307. Communication module 4307 is able to both communicate the status of device 4300 and to receive updates to and from an external source for example including but not limited to a PDA, computer, server, cellular telephone or the like. Communication is mediated by communication protocols for example including but not limited to cellular, wireless, optical, IR, RF, or the like communication protocols; communication protocols used may be encrypted.

For example, when continuous glucose readings from sensor 4306 as processed by controller 4304 indicate that the blood sugar level is rising at an increased rate, controller 4304 then indicates to drug production module 4308 to begin or increase insulin production at a required rate. Similarly, controller 4304 utilizes tissue treatment element 4302 to initiate target tissue stimulation while drug delivery module 4305 is used to delivery the drug to the target site at an appropriate rate so as to maximize tissue absorption in a timely and dose specific manner. Controller 4304 may implement different drug delivery protocols based on new protocols communicated from an external source via communication module 4307. As sensor 4306 continues to monitor the various metabolic parameter(s), changes are implemented in a feedback loop manner that best suits the metabolic needs of the patient.

Figure 43B:
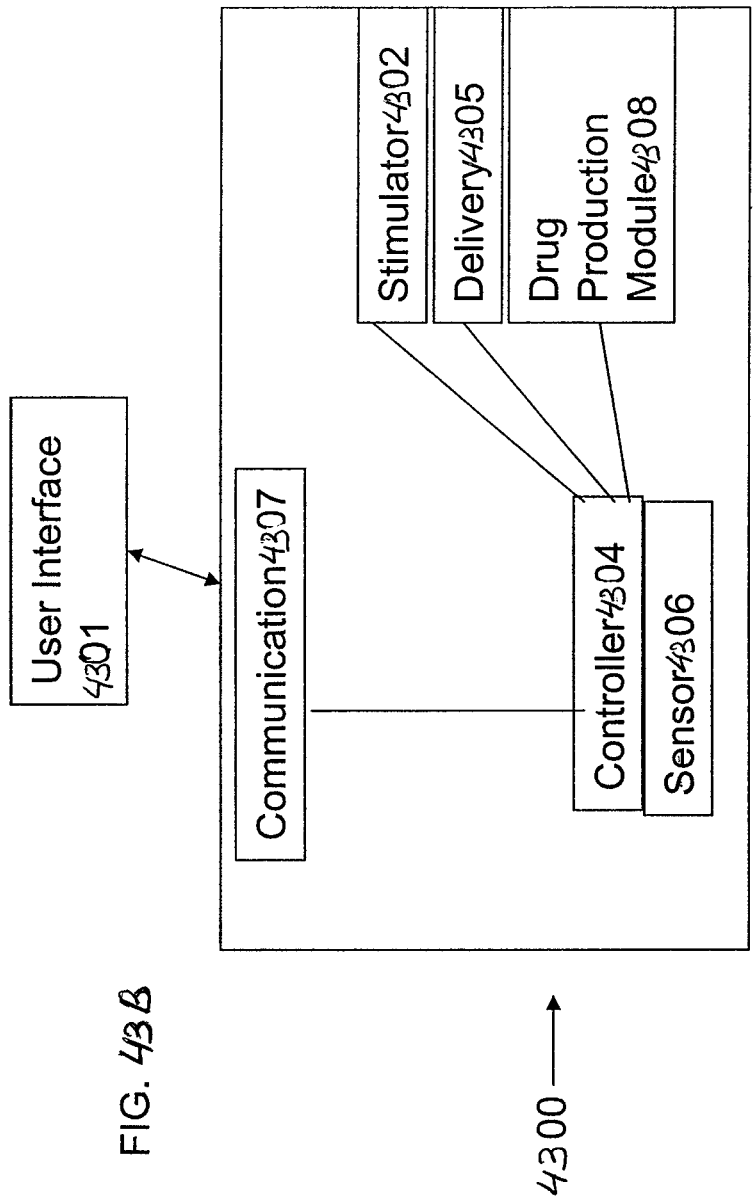
FIG. 43B is a schematic diagram of an exemplary embodiment of the implanted drug delivery device according to the present invention.

FIG. 43B depicts a schematic block diagram of an embodiment of the implanted drug delivery device 4300 according to the present invention as depicted in FIG. 43A and having an external user interface 4301. User interface 4301 communicates to drug delivery device 4300 using a communication protocol for example including but not limited to cellular telephony, wireless, optical, IR, RF or the like communication protocol. User interface 4301 communicates to controller 4304 data relating to any one of device 4300 components. For example, user interface 4301 may trigger insulin production or delivery (or other drug production or delivery) through drug production module 4308 and/or drug delivery module 4305, respectively, by way of communication with controller 4304. Similarly, user interface 4301 may indicate a particular stimulation protocol to be performed by using tissue treatment element 4302.

Figure 44A:
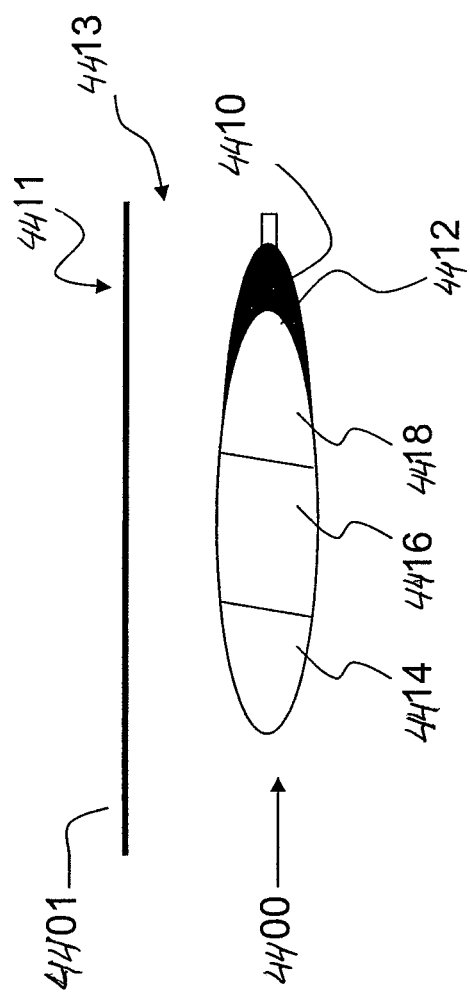
FIGS. 44A-C are various schematic diagrams of exemplary embodiments of the implanted drug delivery device according to the present invention.
Figure 44B:
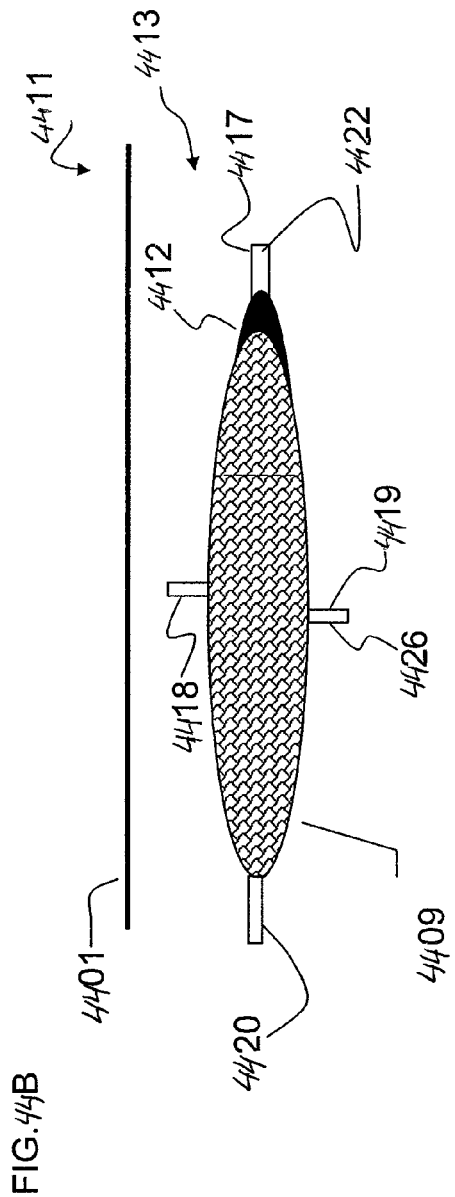
Figure 44C:
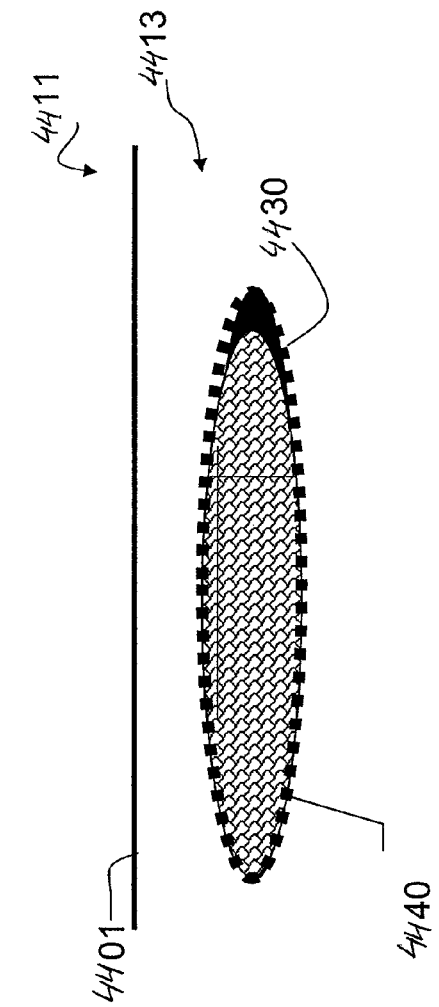

FIGS. 44A-C are embodiments of device 400 depicted in FIGS. 43A-C. FIG. 44A depicts device 4400 that is implanted subcutaneously beneath the skin layer 4401, therefore implanted layer 4413 is below the skin layer 4401 while external layer 4411 is outside skin layer 4401. Implantation may be achieved by subcutaneous injection, keyhole surgery, or surgery performed with local anesthesia or the like. Device 4400 includes a catheter 4410 that delivers the drug to a target site.

Drug delivery and the pharmacokinetic and pharmacodynamic properties are differentially controlled with tissue treatment element 4412 that more stimulates tissue through one or more treatment methods for example including but not limited to heat, temperature control, micro massage or physical or vibrational stimulation, ultrasound, RF, IR, optical irradiation or any combination of them or the like. Tissue treatment element 4412 may stimulate the drug directly, to control its properties; for example, the insulin may be kept at a constant temperature to ensure that it is in active and viable form while the surrounding tissue is stimulated by heat. Controller 4414, sensor 4416, and drug production module 4418 are incorporated into device 4400 and function as depicted in FIGS. 43A and 43B.

The closed loop drug delivery system 4400 uses at least one or more sensors 4416 to determine the metabolic parameters; where controller 4414 utilized the sensor parameters to determine the appropriate action to take. For example, controller 4414 may trigger the drug production process with the drug production module 4418. Once the drug is produced and is ready for delivery controller 4414 activates tissue treatment element 4412 to prepare the target tissue for drug delivery which is accomplished via catheter 4410. Drug delivery catheter 4410 may come in different forms as depicted in FIGS. 44B-44C. As the drug is absorbed by the target site it brings about changes in the metabolic parameters that are sensed by at least one or more sensors 4416, of which one is shown for the purpose of explanation only and without any intention of being limiting. The change in the data is then communicated to the controller 4414 to bring about an adjustment in the treatment protocol and therefore differentially control the different components, for example including drug production module 4418 and/or tissue treatment element 4412.

FIG. 44B depicts an implementation of an implanted delivery module as previously described. Delivery device 4409 includes a plurality of catheters 4417, 4418, 4419 and 4420 that introduce a drug over a larger area within the target site. The plurality of catheters 4417-4420 may further encase at least one or more sensors 4426 or a tissue treatment element 4422 that sense and stimulate the tissue target site.

FIG. 44C depicts an implementation of an implanted delivery module as previously described. The delivery method is achieved with the use of a selectively permeable member 4430 that delivers the drug to the target tissue through a larger surface area, therefore further improving the drug absorption into the blood system.

Neural Stimulation of Tissue During Drug Delivery

Figure 45:
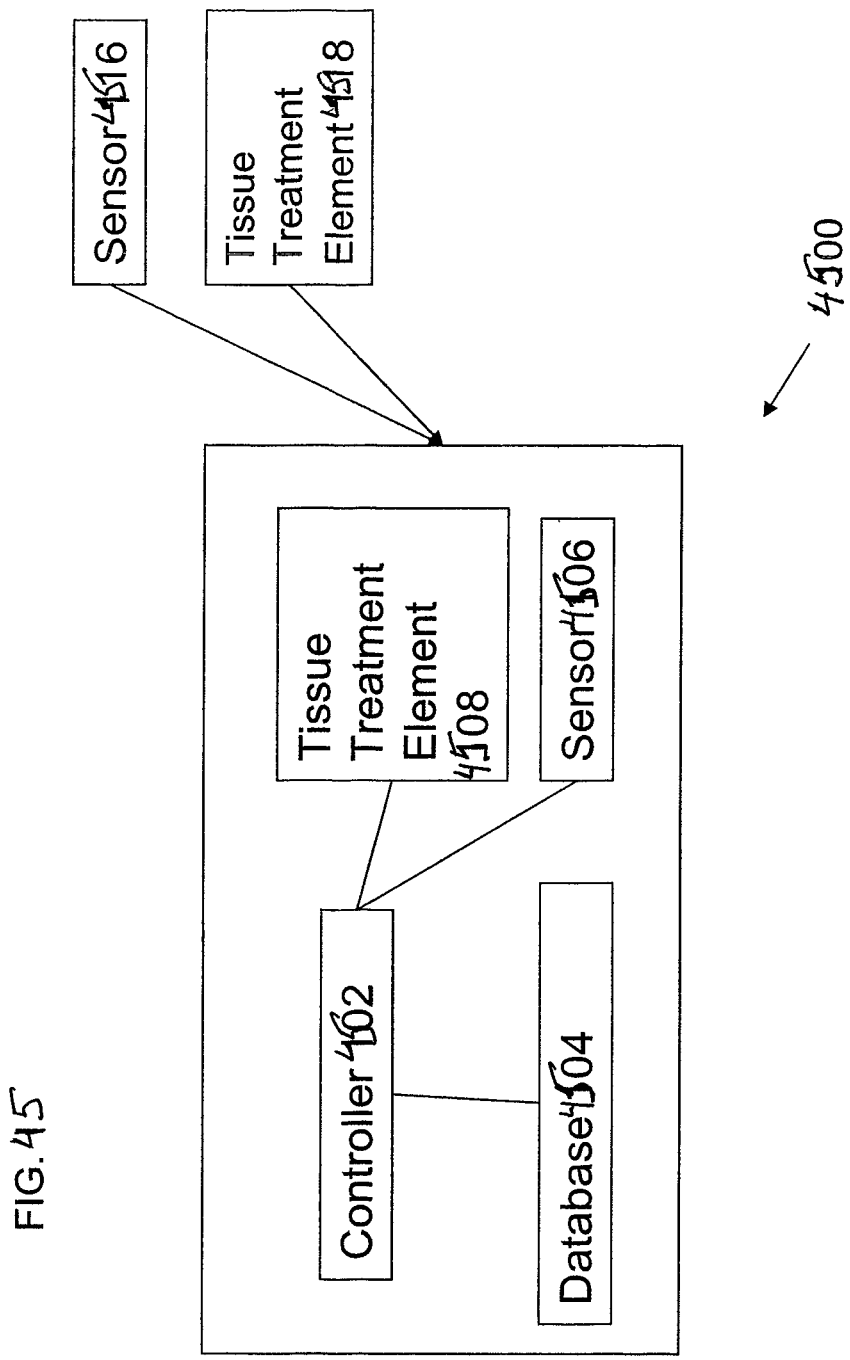
FIG. 45 is a schematic block diagram of a drug delivery device used with the treatment method of the present invention.

Referring now to the drawings, FIG. 45 is a schematic block diagram of an drug delivery device 4500 that may be used with the neural stimulation method according to the present invention for controlled drug delivery to a target tissue having controllable tissue neural stimulation. Drug delivery device 4500 includes controller 4502, database 4504, tissue treatment element 4508 and sensors 4506. A plurality of other components, such as tissue treatment element 4518 and sensor 4516, may not associated with the drug delivery device 4500. Drug delivery device 4500 may be placed in different locations, including but not limited to transcutaneously, subcutaneously, implanted or externally. The placement of drug delivery device 4500 is dependent on the treatment and drug to be delivered.

In some embodiments, neural stimulation treatment protocol is stored in database 4504 and is accessible by controller 4502 to determine the neural stimulation treatment protocol to be used. Controller 4502 is used to activate tissue treatment element 4508 to initiate treatment at the tissue delivery site. Sensor 4506, which may for example be implemented for Laser Doppler Flowmetry (LDF), is used to measure the efficacy of the treatment evoked by tissue treatment element 4508. Sensor 4506, tissue treatment element 4508 and controller 4502 are functionally integrated to bring about a desired effect, more based on the neural stimulation treatment protocol stored in database 4504.

Additional sensors 4516 and tissue treatment element 4518 may be placed at locations at a distance from device 4500. Incorporating sensor 4516 and treatment element 4518 provides for additional control of the treatment protocol in some embodiments. Further, sensor 4516 and treatment element 4518 may be placed at different tissue site(s) from sensor 4506 and element 4508, thereby allowing device 4500 and controller 4502 to measure and control and calibrate the neural stimulation based on data obtained over a larger area.

Additional treatment element 4518 may be a different type of element than that of element 4508, thereby allowing for a plurality of different types of treatment elements to be used with device 4500. For example, element 4508 may be used to introduce an electric current while element 4518 may be used to introduce heat. As another non-limiting example, element 4508 may be used to introduce heat while element 4518 may be used to introduce cold. Optimally the use of a plurality treatment elements (such as the non-limiting example of two elements 4508 and 4518) may allow for increased individualization of the axon reflex treatment protocol over a larger area.

Sensors 4516 and 4506 may be used to measure different measurands to provide more control of device 4500. For example, sensor 4516 may be a Laser Doppler Flowmetry (LDF) measuring vasodilatation while sensor 4506 may be heat sensor measuring tissue temperature.

Figure 46:
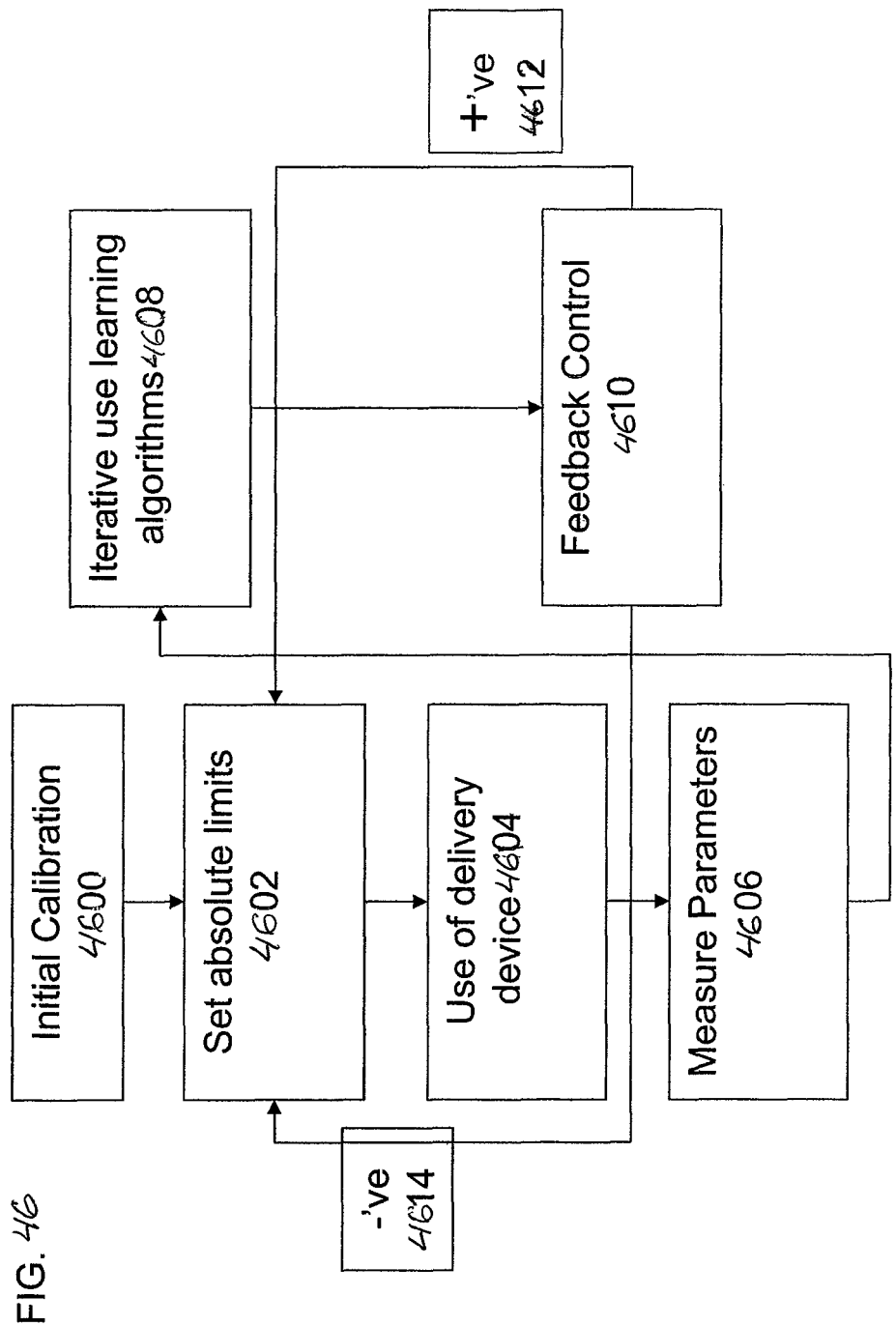
FIG. 46 is a flow chart of the treatment calibration process according to the present invention.

FIG. 46 is a flowchart that depicts the calibration processes according to some embodiments or methods of the present invention. In stage 4600 the device is calibrated to the user where tissue treatment site, type of drug and indicated to the delivery device to evoke the correct treatment protocol. Furthermore, personal data such as comfort level may be set by the user. The limits and parameters defined in stage 4600 are set in stage 4602 and incorporated into the delivery device. In stage 4604 the initial treatment is implemented by the controller 102 of FIG. 45 and at least one or more sensors, which may, for example, be implemented with Laser Doppler Flowmetry (LDF), is used to monitor the advancement of the treatment process as the treatment protocol advances. In stage 4606 the parameters for example including but not limited to, burst timing, timing and length of resting period, heat levels, temperature or current type, and the like, are measured and may be altered to bring about the effects relative to the elapsed time and where treatment effects such as vasodilatation levels or threshold levels are relative to expected levels.

In stage 4608 the treatment may be altered according to a learning algorithm (for example) known in the art, for example including but not limited to a PID (proportional-integral-derivative) controller, artificial intelligence mechanism, or the like to adjust or adapt the treatment protocols to be more specific or tailored to the drug delivery needs of the user.

In stage 4610 the altered treatment according to the learning algorithm is tested using feedback control that may be repeated with earlier stage 4602, which may include positive feedback 4612 for certain parameters or negative feedback 4614 for other parameters. Positive and negative controls are used to reset and alter old protocols, and may be used to adjust new parameters or treatment protocols for future use in stage 4602. Different treatment protocols may stored by the database 104 of FIG. 45, for different situations.

The calibration protocol depicted above may be implemented one time for a specific user only using stages 4600-4604, while all of the stages may be used when treatment is implemented once a day, at every drug delivery event, or in a dynamic process as necessary.

Figure 47:
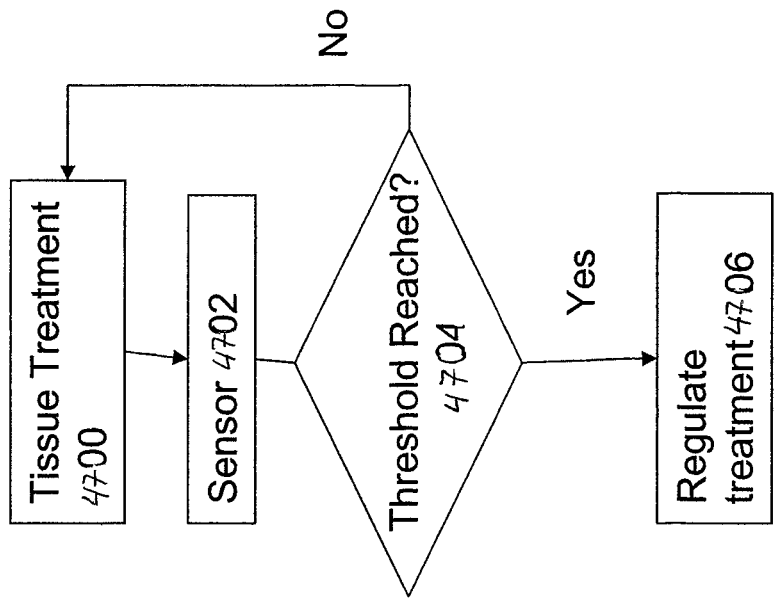
FIG. 47 is a flow chart of the treatment calibration process according to the present invention.

FIG. 47 presents a flow chart depicting the neural stimulation treatment protocol and the interaction of the sensor and treatment element to control the various parameters, and may include (but not limited to) one or more of burst timing, timing and length of resting period, heat levels, temperature or current type, heating power, time for temperature to increase or decrease, that may be controllably changed to personalize the treatment protocol relative to the user. Controller 4502 of FIG. 45 initiates activity of at least one treatment element of FIG. 45, for initiating treatment in stage 4700.

The tissue treatment implemented is the axon reflex according to known protocols, may be stored in database 4504 described in FIG. 45. Tissue temperature is gradually increased to an upper limit more based on the user's comfort level and may be, according to one or more tissue dependent temperature limits, for example 43° C. for skin, according to safety standards that are known in the art. The temperature rise occurs over a predetermined period of time, for example 64 seconds, to cause a temperature increase from 37° C. to 43° C. Alternatively, an oscillating heat burst may be implemented to bring about the overall neural stimulation temperature increase; treatment may be performed according to a 2-5 ratio, featuring 2 seconds of temperature increase and a 5 second resting period, or as known and accepted in the art. The treatment protocol to bring about the axon reflex by heat induction may be further dependent on the location of the treatment element, which may be implanted or external, and also on the tissue being stimulated.

In some embodiments, as heat and other treatments are introduced in stage 4700, a sensor records the changes in the temperature, and monitors vasodilatation, and may include the rate of change of temperature and/or dilation, in stage 4702. As the sensor records the change in vasodilatation, and temperature, controller 4502 of FIG. 45, and more continuously, may determine whether the vasodilatation threshold has been reached in stage 4704.

In stage 4706, if a threshold has been reached, then the controller performs any function(s) required to limit or reduce the treatment element activity to regulate treatment. If the threshold has not been reached and vasodilatation has not reached required levels to bring about an improvement in drug pharmacokinetic and pharmacodynamic properties, then controller 4502 of FIG. 45 may increase the activity of treatment elements in stage 4700 within the limits known and accepted in the art to bring about the required level of heat and vasodilatation.

Figure 50:
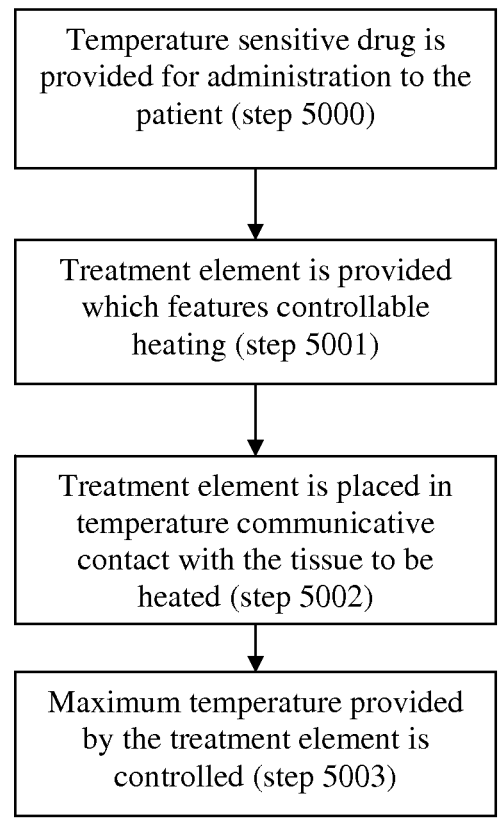
FIG. 50 is a flow chart illustrating an exemplary method for controlling temperature of heating that is provided by a treatment element in order to prevent degradation of a temperature sensitive drug.

FIG. 50 presents a flow chart depicting a method for controlling the temperature of heating provided by a treatment element in order to prevent degradation of a temperature sensitive drug, according to some embodiments of the present invention. As shown in step 5000, a drug is provided for administration to the patient, which is sensitive to degradation above a limiting temperature. In step 5001, a treatment element is provided which features controllable heating through a controllable heating element. In step 5002, the treatment element is placed in temperature communicative contact with the tissue to be heated, such that heat from the treatment element is transferred to the tissue to be heated.

In step 5003, the maximum temperature provided by the treatment element is controlled, such that the temperature experienced by the drug (that is, in the environment of the drug) does not exceed the limiting temperature sustainable by the drug before degradation occurs. The maximum temperature can be calibrated for each drug and/or class of drugs. For example, for some types of insulin, the limiting temperature is about 37° C.

Such control can be provided through a microprocessor or other processor for controlling the temperature output by a heating element. A sensor may also be provided in order to measure the temperature at the tissue being heated, in order to determine the temperature experienced by the drug.

In some embodiments, the treatment element includes one or more materials capable of generating an exothermic reaction, in which the amount of such materials and/or ratio is calculated in order for the temperature of the reaction to not exceed the maximum temperature set for the treatment element according to the desired limiting temperature of the drug. The exothermic reaction can be a heat-generating oxidation reaction, for example, using a mixture of iron powder, activated carbon, salt and water. As can be understood by one skilled in the art, other mixtures and/or materials can be used.

While the invention has been described with respect to a limited number of embodiments, it will be appreciated that many variations, modifications and other applications of the invention may be made. Any and all patents, patent applications, articles and other published and non-published documents referred to anywhere in the present disclosure is herein incorporated by reference in their entirety. It should be noted that whenever the local effect of the treatment is described over the drug infused region, the treatment effect can be also on larger volume in the vicinity of the drug infused volume or on a smaller volume, depending on the specific treatment.

Although particular embodiments have been disclosed herein in detail, this has been done by way of example and for purposes of illustration only, and is not intended to be limiting. In particular, it is contemplated by the inventors that various substitutions, alterations, and modifications may be made without departing from the spirit and scope of the disclosed embodiments. Other aspects, advantages, and modifications are considered to be within the scope of the disclosed and claimed embodiments, as well as other inventions disclosed herein. The claims presented hereafter are merely representative of some of the embodiments of the inventions disclosed herein. Other, presently unclaimed embodiments and inventions are also contemplated. The inventors reserve the right to pursue such embodiments and inventions in later claims and/or later applications claiming common priority.

What is claimed is:

1. A device for delivering a therapeutic substance into the body of a patient, comprising:
    an infusion catheter configured to be inserted into a bodily tissue disposed at an insertion site located on the body of the patient and further configured to deliver the therapeutic substance into the body of the patient to an infused region, wherein the infused region includes a volume of the bodily tissue surrounding the insertion site;
    a catheter securing element configured to be adhered to the skin of the patient and further configured to secure the infusion catheter to the skin of the patient;
    a housing including
        a substance delivery device for infusing the therapeutic substance into the infusion catheter for delivery of the therapeutic substance into the infused region;
        a sensor built into the housing and configured to detect infusion of the therapeutic substance;
        a treatment element configured to apply a treatment in a vicinity of the infused region to modify a pharmacokinetic and/or pharmacodynamic profile of the therapeutic substance; and
    a controller unit in communication with the treatment element and configured to initiate application of the treatment by the treatment element upon detecting beginning of the infusion of the therapeutic substance.

2. The device according to claim 1, wherein the treatment is applied at a time selected from a group consisting of: before the therapeutic substance is delivered to the body of the patient, during delivery of the therapeutic substance to the body of the patient, and after the therapeutic substance has been delivered to the body of the patient.

3. The device according to claim 1, wherein the substance delivery device is a delivery pump.

4. The device according to claim 1, wherein the treatment element is configured to apply treatment in order to perform at least one of the functions selected from a group consisting of: enabling a faster onset of action of the therapeutic substance infused into the infused region, enabling a faster peak of action of the therapeutic substance infused into the infused region, enabling a faster clearance of the therapeutic substance from the infused region and into a circulatory system of the patient, improving the repeatability of the pharmacokinetic and/or pharmacodynamic profile in response to the infusion of the therapeutic substance, reducing a variability of absorption of the therapeutic substance into the blood system and/or lymphatic system of the patent, reducing a variability of onset of action of the therapeutic substance, reducing a variability of time to peak of action of the therapeutic substance, and reducing a variability of the clearance of the therapeutic substance from the infused region and into the circulatory system of the patient.

5. The device according to claim 1, wherein the substance is configured to be injected subcutaneously and further configured to have a systemic effect.

6. The device according to claim 3, wherein the therapeutic substance is selected from a group consisting of: insulin, insulin analogues, and insulin mimetics.

7. The device according to claim 1, wherein the treatment element is further configured to modify blood perfusion in the vicinity of the infused region.

8. The device according to claim 6, wherein the treatment element is a heater configured to modify a temperature of the bodily tissue in the vicinity of the infused region;
    wherein the heater does not heat the therapeutic substance above a limiting temperature.

9. The device according to claim 6, wherein the treatment element is configured to heat the skin of the patient in the vicinity of the infused region to a temperature in a range of 37-39° C. for a predetermined period of time after bolus infusion initiation.

10. The device according to claim 9, wherein the insulin is a rapid acting insulin.

11. The device according to claim 10, wherein insulin is infused into the patient using long period bolus mode, such as square or split bolus mode, to adjust the insulin pharmacokinetics and/or pharmacodynamics.

12. The device according to claim 10, wherein insulin is infused into the patient using fast bolus mode.

13. The device according to claim 9, wherein insulin is a regular insulin.

14. The device according to claim 6, wherein the sensor is configured to detect an infusion of an insulin bolus.

15. The device according to claim 14, wherein the sensor includes an electromagnetic sensing element for measuring an electromagnetic emission of the delivery pump.

16. The device according to claim 3, wherein the controller unit is disposed inside the delivery pump.

17. The device according to claim 8, wherein the housing further includes a reservoir containing the therapeutic substance and an infusion tube, and is configured to enclose the treatment element along with the substance delivery device and the reservoir;

wherein the treatment element is configured to apply heat in the vicinity of the infused region without heating the reservoir and the infusion tube above the limiting temperature.

18. The device according to claim 1, wherein the substance delivery device is disposable.

19. The device according to claim 1, wherein the treatment element is disposed in the catheter securing element.

20. The device according to claim 1, wherein the treatment element includes a heater and is configured to regulate heating of the infused region to stabilize its temperature at a pre-determined temperature in order to stabilize pharmacokinetics of the infused therapeutic substance.

21. The device according to claim 1, wherein the applied treatment is selected from a group consisting of: heating, cooling, intermittent temperature change, optical radiation, micro-wave, radio frequency, electromagnetic radiation, vibration device, physical stimulation, massage the infused region, suction, vacuum, electric field, magnetic field, acoustic signal, ultrasound, and application of one more additional substances to modify the infused substance pharmacokinetics, and/or a combination of at least two of the above treatments.

22. A method for delivering a therapeutic substance into the body of a patient, the method comprising the steps of:

providing a device for delivering the therapeutic substance into the body of the patient having an infusion catheter;
a catheter securing element;
a housing including
    a substance delivery device;
    a sensor built into the housing and configured to detect infusion of the therapeutic substance;
a treatment element; and
a controller unit in communication with the treatment element;

adhering the catheter securing element to the skin of the patient and securing the infusion catheter to the skin of the patient;

inserting the infusion catheter into a bodily tissue disposed at an insertion site located on the body of the patient;

using the substance delivery device, infusing the therapeutic substance into the infusion catheter;

using the infusion catheter, delivering the therapeutic substance into the body of the patient to an infused region, wherein the infused region includes a volume of the bodily tissue surrounding the insertion site;

using the controller unit, initiating application of the treatment by the treatment element upon detecting beginning of the infusion of the therapeutic substance;

using the treatment element, applying the treatment in a vicinity of the infused region; and modifying a pharmacokinetic and/or pharmacodynamic profile of the infused therapeutic substance.

* * * * *

UNITED STATES PATENT AND TRADEMARK OFFICE
CERTIFICATE OF CORRECTION

| | | |
|---|---|---|
| PATENT NO. | : 8,622,991 B2 | Page 1 of 1 |
| APPLICATION NO. | : 12/450246 | |
| DATED | : January 7, 2014 | |
| INVENTOR(S) | : Pesach et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 887 days.

Signed and Sealed this
Eighteenth Day of August, 2015

Michelle K. Lee
*Director of the United States Patent and Trademark Office*